United States Patent
Do et al.

(10) Patent No.: US 12,246,062 B2
(45) Date of Patent: Mar. 11, 2025

(54) RECOMBINANT HUMAN ACID ALPHA-GLUCOSIDASE

(71) Applicant: Amicus Therapeutics, Inc., Cranbury, NJ (US)

(72) Inventors: Hung Do, New Hope, PA (US); Russell Gotschall, Doylestown, PA (US); Richie Khanna, Somerset, NJ (US); Yi Lun, Plainsboro, NJ (US); Hing Char, East Brunswick, NJ (US); Sergey Tesler, Monroe, NJ (US); Wendy Sunderland, Doylestown, PA (US); Enrique Diloné, Basking Ridge, NJ (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 124 days.

(21) Appl. No.: 16/613,919

(22) PCT Filed: May 15, 2018

(86) PCT No.: PCT/US2018/032815
§ 371 (c)(1),
(2) Date: Nov. 15, 2019

(87) PCT Pub. No.: WO2018/213340
PCT Pub. Date: Nov. 22, 2018

(65) Prior Publication Data
US 2021/0393747 A1 Dec. 23, 2021

Related U.S. Application Data

(60) Provisional application No. 62/660,758, filed on Apr. 20, 2018, provisional application No. 62/624,638, filed on Jan. 31, 2018, provisional application No. 62/618,021, filed on Jan. 16, 2018, provisional application No. 62/567,334, filed on Oct. 3, 2017, provisional application No. 62/564,083, filed on Sep. 27, 2017, provisional application No. 62/529,300, filed on Jul. 6, 2017, provisional application No. 62/506,561, filed on May 15, 2017, provisional application No. 62/506,569, filed on May 15, 2017, provisional application No. 62/506,574, filed on May 15, 2017.

(51) Int. Cl.
*A61K 38/47* (2006.01)
*A61P 21/00* (2006.01)

(52) U.S. Cl.
CPC .............. *A61K 38/47* (2013.01); *A61P 21/00* (2018.01); *C12Y 302/0102* (2013.01)

(58) Field of Classification Search
CPC . C12N 9/26; A61P 21/00; A61P 25/00; A61K 38/47
See application file for complete search history.

(56) References Cited

U.S. PATENT DOCUMENTS

| | | |
|---|---|---|
| 4,837,237 A | 6/1989 | Rohrschneider et al. |
| 4,985,445 A | 1/1991 | Tsuruoka et al. |
| 5,011,829 A | 4/1991 | Hirsch et al. |
| 5,103,008 A | 4/1992 | Scudder et al. |
| 5,236,838 A | 8/1993 | Rasmussen et al. |
| 5,399,567 A | 3/1995 | Platt et al. |
| 5,472,969 A | 12/1995 | Platt et al. |
| 5,580,757 A | 12/1996 | Desnick et al. |
| 5,786,369 A | 7/1998 | Platt et al. |
| 5,801,185 A | 9/1998 | Platt et al. |
| 5,879,680 A | 3/1999 | Ginns et al. |
| 6,083,725 A | 7/2000 | Selden et al. |
| 6,118,045 A | 9/2000 | Reuser et al. |
| 6,210,666 B1 | 4/2001 | Miyamura |
| 6,225,325 B1 | 5/2001 | Jacob |
| 6,274,597 B1 | 8/2001 | Fan et al. |
| 6,395,884 B1 | 5/2002 | Selden et al. |

(Continued)

FOREIGN PATENT DOCUMENTS

| | | |
|---|---|---|
| CN | 104164412 A | 11/2014 |
| CN | 104379162 A | 2/2015 |

(Continued)

OTHER PUBLICATIONS

Khanna et al. 2012; The pharmacological chaperone AT2220 increases recombinant human acid-alpha-glucosidase uptake and glycogen reduction in a mouse model of Pompe disease. PLoS ONE 7(7): e70776, pp. 1-12.*

Van Hove et al. 1996; High level production of recombinant human lysosomal acid alpha-glucosidase in Chinese hamster ovary cells which targets to heart muscle and corrects glycogen accumulation in fibroblasts from patients with Pompe disease. Pro. Natl. Acad. Sci. 93: 65-70.*

Schoser et al. 2019; A systemic review of the health economics of Pompe Disease. Pharmaco Economics. 3: 479-493.*

(Continued)

*Primary Examiner* — Paul J Holland
(74) *Attorney, Agent, or Firm* — Servilla Whitney LLC

(57) ABSTRACT

Provided are a recombinant acid α-glucosidase and pharmaceutical composition comprising a recombinant acid α-glucosidase, wherein the recombinant acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa. Also provided herein are methods of producing, purifying, and formulating the recombinant acid α-glucosidase or pharmaceutical composition for administration to a subject and methods of treating a disease or disorder such as Pompe disease using the recombinant acid α-glucosidase or pharmaceutical composition.

19 Claims, 57 Drawing Sheets
Specification includes a Sequence Listing.

(56) References Cited

U.S. PATENT DOCUMENTS

| | | |
|---|---|---|
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,465,488 B1 | 10/2002 | Butters et al. |
| 6,534,300 B1 | 3/2003 | Canfield |
| 6,537,785 B1 | 3/2003 | Canfield |
| 6,545,021 B1 | 4/2003 | Mueller et al. |
| 6,583,158 B1 | 6/2003 | Fan et al. |
| 6,589,964 B2 | 7/2003 | Fan et al. |
| 6,599,919 B2 | 7/2003 | Fan et al. |
| 6,696,059 B2 | 2/2004 | Jacob et al. |
| 6,916,829 B2 | 7/2005 | Fan et al. |
| 7,141,582 B2 | 11/2006 | Fan et al. |
| 7,351,410 B2 | 4/2008 | van Bree et al. |
| 7,371,366 B2 | 5/2008 | Canfield |
| 7,396,811 B2 | 7/2008 | LeBowitz et al. |
| 7,560,424 B2 | 7/2009 | LeBowitz et al. |
| 7,655,226 B2 | 2/2010 | Van Bree et al. |
| 7,658,916 B2 | 2/2010 | Zhu et al. |
| 7,723,296 B2 | 5/2010 | Zhu |
| 7,785,856 B2 | 8/2010 | LeBowitz et al. |
| 7,858,576 B2 | 12/2010 | LeBowitz et al. |
| 7,910,545 B2 | 3/2011 | Meeker et al. |
| 7,981,864 B2 | 7/2011 | LeBowitz |
| 8,759,501 B2 | 6/2014 | Zhu et al. |
| 8,785,168 B2 | 7/2014 | LeBowitz et al. |
| 8,900,552 B2 | 12/2014 | Chen |
| 8,940,766 B2 | 1/2015 | Boyd et al. |
| 9,056,101 B2 | 6/2015 | Lockhart et al. |
| 9,181,184 B2 | 11/2015 | Mugrage et al. |
| 9,186,420 B2 | 11/2015 | Koeberl |
| 9,303,249 B2 | 6/2016 | Valenzano et al. |
| 9,404,100 B2 | 8/2016 | Valenzano et al. |
| 9,598,682 B2 | 3/2017 | Callewaert et al. |
| 10,046,033 B2 | 8/2018 | Valenzano et al. |
| 10,208,299 B2 | 2/2019 | Gotshall et al. |
| 10,227,577 B2 | 3/2019 | Do et al. |
| 10,464,962 B2 | 11/2019 | Avila et al. |
| 10,512,676 B2 | 12/2019 | Char et al. |
| 10,512,677 B2 | 12/2019 | Valenzano et al. |
| 10,857,212 B2* | 12/2020 | Do .................. A61P 21/00 |
| 10,961,522 B2* | 3/2021 | Gotschall ............ C12N 9/2465 |
| 11,278,601 B2* | 3/2022 | Do .................. C12Y 302/0102 |
| 2002/0049233 A1 | 4/2002 | Kararli et al. |
| 2002/0073438 A1 | 6/2002 | Reuser et al. |
| 2002/0095135 A1 | 7/2002 | Meeker et al. |
| 2002/0137125 A1 | 9/2002 | Zhu |
| 2002/0157123 A1 | 10/2002 | Reuser et al. |
| 2004/0180419 A1 | 9/2004 | Fan |
| 2004/0204379 A1 | 10/2004 | Cheng et al. |
| 2005/0058634 A1 | 3/2005 | Zhu |
| 2005/0244400 A1 | 11/2005 | LeBowitz et al. |
| 2006/0121018 A1 | 6/2006 | LeBowitz |
| 2006/0264467 A1 | 11/2006 | Mugrage et al. |
| 2007/0178081 A1 | 8/2007 | Fan |
| 2009/0117091 A1 | 5/2009 | LeBowitz et al. |
| 2009/0191178 A1 | 7/2009 | Zankel et al. |
| 2009/0203575 A1 | 8/2009 | LeBowitz et al. |
| 2010/0119502 A1 | 5/2010 | Do et al. |
| 2010/0260740 A1 | 10/2010 | Boyd et al. |
| 2010/0266571 A1 | 10/2010 | Lockhart et al. |
| 2011/0136151 A1 | 6/2011 | Wustman et al. |
| 2011/0189710 A1 | 8/2011 | Wustman et al. |
| 2011/0223147 A1 | 9/2011 | Lebowitz et al. |
| 2011/0268721 A1 | 11/2011 | Do et al. |
| 2011/0300120 A1 | 12/2011 | Avila et al. |
| 2012/0064545 A1 | 3/2012 | Khanna et al. |
| 2012/0148556 A1 | 6/2012 | Lebowitz et al. |
| 2013/0158239 A1 | 6/2013 | Callewaert et al. |
| 2014/0186326 A1 | 7/2014 | Canfield et al. |
| 2014/0193390 A1 | 7/2014 | Valenzano et al. |
| 2014/0249054 A1 | 9/2014 | Gelb et al. |
| 2015/0044194 A1 | 2/2015 | Valenzano et al. |
| 2015/0086530 A1 | 3/2015 | Greene et al. |
| 2015/0147309 A1 | 5/2015 | Parenti et al. |
| 2015/0258081 A1 | 9/2015 | Lukas et al. |
| 2015/0352042 A1* | 12/2015 | Char .................. A61K 9/0019 514/315 |
| 2016/0051528 A1 | 2/2016 | Mugrage et al. |
| 2016/0184410 A1 | 6/2016 | Chen |
| 2016/0243203 A1 | 8/2016 | van Bree et al. |
| 2017/0049161 A1 | 3/2017 | Do et al. |
| 2017/0056483 A1 | 3/2017 | Valenzano et al. |
| 2017/0298335 A1 | 10/2017 | Gotschall et al. |
| 2017/0335301 A1 | 11/2017 | Do et al. |
| 2018/0221357 A1 | 8/2018 | Mugrage et al. |
| 2018/0360928 A1 | 12/2018 | Valenzano et al. |
| 2019/0382742 A1 | 12/2019 | Do et al. |

FOREIGN PATENT DOCUMENTS

| | | |
|---|---|---|
| CN | 107075468 A | 8/2017 |
| EP | 1820862 A2 | 8/2007 |
| EP | 1137762 B1 | 10/2008 |
| EP | 2020438 A1 | 2/2009 |
| FR | 2861991 A1 | 5/2005 |
| JP | 2005-523882 A | 8/2005 |
| JP | 2007-523648 A | 8/2007 |
| JP | 2008-525457 A | 7/2008 |
| JP | 2008545657 A | 12/2008 |
| JP | 2010525084 A | 7/2010 |
| JP | 2011512876 A | 4/2011 |
| WO | WO 2000/034451 A1 | 6/2000 |
| WO | WO 2001/019955 A2 | 3/2001 |
| WO | WO 2001/97829 A2 | 12/2001 |
| WO | WO 2003/032907 A2 | 4/2003 |
| WO | WO 2004/069190 A2 | 8/2004 |
| WO | WO 2005/077093 A2 | 8/2005 |
| WO | WO 2006/071613 A2 | 7/2006 |
| WO | WO 2006/125141 A2 | 11/2006 |
| WO | WO 2008/112525 A2 | 9/2008 |
| WO | WO 2008/134628 A2 | 11/2008 |
| WO | WO 2009/066069 A1 | 5/2009 |
| WO | 2009102895 A2 | 8/2009 |
| WO | WO 2009/114679 A2 | 9/2009 |
| WO | WO 2010/015816 A2 | 2/2010 |
| WO | WO 2010075010 A2 | 7/2010 |
| WO | WO 2010/148253 A2 | 12/2010 |
| WO | 2011039634 A2 | 4/2011 |
| WO | WO 2011/109600 A1 | 9/2011 |
| WO | 2012042386 A2 | 4/2012 |
| WO | WO 2012/145644 A1 | 10/2012 |
| WO | WO 2013/013017 A2 | 1/2013 |
| WO | WO 2013/091897 A1 | 6/2013 |
| WO | 2013136189 A2 | 9/2013 |
| WO | WO 2013/166249 A1 | 11/2013 |
| WO | WO 2015/097088 A1 | 7/2015 |
| WO | WO-2016054231 A1 * | 4/2016 ........... C12N 9/2465 |
| WO | WO-2017049161 A1 | 3/2017 |
| WO | WO-2017117407 A1 | 7/2017 |
| WO | WO-2017173059 A1 | 10/2017 |

OTHER PUBLICATIONS

Amicus Therapeutics. 2021.Amicus' AT-GAA Shows Clinically Meaningful & Significant Improvements in Both Musculoskeletal and Respiratory Measures in Late-Onset Pompe Disease Compared to Standard of Care in Pivotal Phase 3 PROPEL Study on the web at:.*
: con't: ir.amicusrx.com/news-releases/news-release-details/amicus-gaa-shows-clinically-meaningful-significant-improvements. pp. 1-5.*
Amalfitano et al., "Recombinant human acid α-glucosidase enzyme therapy for infantile glycogen storage disease type II: Results of a phase I/II clinical trial," Genetics in Medicine 3(2): 132-138 (2001).
Andro et al. (Ask Dr, Andro: What Are Human Equivalent Doses (HED) and How Do I Calculate Them? 2011 pp. 1-4).
Asano et al., Nitrogen-in-the-ring pyranoses and furanoses: structural basis of inhibition of mammalian glycosidases. J. Med. Chem. 1994; 37:3701-06.
Banati, M. et al. (2011) "Enzyme replacement therapy induces T-cell responses in late-onset Pompe disease" Muscle Nerve, 44(5):720-726.

(56) References Cited

OTHER PUBLICATIONS

Barton, N.W. et al. (1991) "Replacement Therapy for Inherited Enzyme Deficiency-Macrophage-Targeted Glucocerebrosidase for Gaucher's Disease" N Eng J Med, 324:1464-1470.

Beck, M. (Sep. 2009) "Alglucosidase alfa: Long term use in the treatment of patients with Pompe disease" Therapeutics and Clinical Risk Management, 5:767-772.

Berge, Stephen M., Lyle D. Bighley, and Donald C. Monkhouse. "Pharmaceutical salts." Journal of pharmaceutical sciences 66.1 (1977): 1-19.

Butters et al., "Imino Sugar Inhibitors for Treating the lysosomal Gl+A156ycosphingolipidoses," Glycobiology 15(10):43R-52R (2005).

Courageot et al., α-Glucosidase inhibitors reduce dengue virus production by affecting the initial steps of virion morphogenesis in the endoplasmic reticulum, Journal of Virology, 2000, 74:564-572.

Cox et al., Novel oral treatment of Gaucher's disease with N-butyldeoxynojilimycin (OGT 918) to decrease substrate biosynthesis, The Lancet, 2000; 355:1481-1485.

Dale, M.P. et al. (1985) "Reversible inhibitors of β-glucosidase" Biochemistry, 24:3530-3539.

Database Score. Seq ID No. 1 sequence in WO 2012145644 A1. Retrieved from: http://score.uspto.gov/ScoreAccessWeb/viewSeqIdResult.htm, pp. 1-3; accessed Jan. 22, 2018, 3 pages.

Do, H. (Feb. 13, 2014) "Chemical Conjugation of Targeting Peptide to ERTs Improve Receptor Binding and Substrate Clearance in Mouse Models of Disease" Amicus Technologies: Presentation from the 10th Lysosomal Disease Network WORLD Symposium, San Diego, CA, Feb. 10-13, 2014; 14 pages.

Do, H. et al. (Feb. 13, 2014) "Chemical Conjugation of Targeting Peptide to ERTs Improve Receptor Binding and Substrate Clearance in Mouse Models of Disease" Amicus Technologies: Poster from the 10th Annual Lysosomal Disease Network WORLD Symposium, San Diego, CA, Feb. 10-13, 2014, Abstract #277; 1 page.

Do, H. et l. (2017) "ATB200/AT2221 Cleared Accumulated Glycogen and Reversed Cellular Dysfunction to Increase Functional Muscle Strength in Mouse Model of Pompe Disease" Amicus Technologies: Poster from the 13th Annual Lysosomal Disease Network WORLD Symposium, San Diego, CA, Feb. 13-17, 2017; Poster #74, Abstract A-348, 1 page.

Do et al "Stabilized next generation recombinant human acid alphaglucosidase ATB200 clears accumulated glycogen and reverses cellular dysfunction to increase functional muscle strength in a mouse model of Pompe disease", Molecular Genetics and Metabolism 120(12); p. S42 (2017).

Duke University, *Duke Obtains FDA Designation for Pompe Disease Therapy*, press release dated Sep. 2, 1997, 2 pages.

EMEA (2006), Scientific Discussion. pp. 1-25.

FDA, "Guidance for Industry—Estimating the Maximum Safe Starting Dose in Initial Clinical Trials for Therapeutics in Adult Healthy Volunteers," Jul. 1, 2005 (Jul. 1, 2005), pp. 1-27, Retrieved from the Internet: URL:https://www.fda.gov/media/72309/download [retrieved on Jun. 9, 2020].

Fryar, C.D. et al. (Oct. 2012) "Anthropometric Reference Data for Children and Adults: United States 2007-2010" National Center for Health Statistics. Vital Health Stat, Series 11, No. 252, 48 pages.

Genzyme Corporation (2010) Myozyme®. Highlights of Prescribing Information. Cambridge, MA: Genzyme Corporation, Jun. 2010, 3 pages.

Gotschall, R. (2015) "Novel rhGAA with Optimal Glycosylation is Significantly Better than Alglucosidase Alfa for Glycogen Clearance in Skeletal Muscles of Gaa KO Mice" Amicus Technologies: Poster from the ACMG Annual Clinical Genetics Meeting, Mar. 25-27, 2015, Salt Lake City, Utah; Abstract #739, 1 page.

Gotschall, R. (2015) "Novel rhGAA with Optimal Glycosylation is Significantly Better than Alglucosidase Alfa for Glycogen Clearance in Skeletal Muscles of Gaa KO Mice" Amicus Technologies: Presentation from the 11th Lysosomal Disease Network World Symposium, Feb. 9-13, 2015, Orlando, Florida; 12 pages.

Gotschall, R. et al. (2015) "Novel rhGAA with Optimal Glycosylation is Significantly Better than Alglucosidase Alfa for Glycogen Clearance in Skeletal Muscles of Gaa KO Mice" Amicus Technologies: Abstract from the 11th Lysosomal Disease Network WORLD Symposium, Feb. 9-13, 2015, Orlando, Florida. Abstract 94, 1 page.

Gotschall, R. et al. (2017) "AT00/AT2221 Reverses Cellular Dysfunction and Increases Muscle Strength in a Pompe Disease Mouse Model" Amicus Therapeutics: Poster from the 4th International Glycogen Storage Disease (GSD) Conference, Jun. 15-17, 2017, University Medical Center, Groningen, The Netherlands; Abstract 48, 1 page.

Hermans et al. (1993) "Human lysosomal α-glucosidase: functional characterization of the glycosylation sites," Biochem J. 289:681-686 (1993).

Extended European Search Report issued by the European Patent Office for Application No. 18802722, dated Jan. 20, 2021, 7 pages.

Jeyakumar et al. Delayed symptom onset and increased life expectancy in Sandhoff disease mice treated with N-butyldeoxynojirimycin, Proc. Acad. Sci. USA. 1999; 96:6388-6393.

Johnson, F.K. et al. (2017) "First-in-Human Preliminary Pharmacokinetic and Safety Data on a Novel Recombinant Acid α-Glucosidase, AT00, Co-administered With the Pharmacological Chaperone AT2221 in ERT-Experienced Patients With Pompe Disease" Amicus Technologies: Poster from the 13th Annual Lysosomal Disease Network WORLD Symposium, San Diego, CA, Feb. 13-17, 2017; Poster #LB-26, 1 page.

Khanna, R. et al. (2014) "The pharmacological chaperone AT2220 increases the specific activity and lysosomal delivery of mutant acid alpha-glucosidase, and promotes glycogen reduction in a transgenic mouse model of Pompe disease" PLoS One, 9(7):e102092, 16 pages.

Khanna, R. et al. (2016) "Co-Administration of the Pharmacological Chaperone AT2221 with a Proprietary Recombinant Human Acid α-Glucosidase Leads to Greater Plasma Exposure and Substrate Reduction Compared to Alglucosidase Alfa" Amicus Therapeutics: Poster from the 12th Annual Lysosomal Disease Network WORLD Symposium Meeting, Feb. 29-Mar. 4, 2016, San Diego, California; 3 pages.

Kishnani et al., Duvolustat HCI Increases Systemic and Tissue Exposure of Active Acid α-Glucosidase in Pompe Patients Co-administered with Alglucosidase α. Molecular Therapy, 2017, 25(5): 1199-1208.

Klinge et al., Enzyme replacement therapy in classical infantile Pompe disease: results of a ten-month follow-up study. Neuropediatrics. 2005; 36(1):6-11.

Kuperus et al., "Long-term benefit of enzyme replacement therapy in Pompe disease A 5-year prospective study," Neurology 89:2365-2373 (2017).

Legler et al., Synthesis of 5-amino-5-deoxy-D-galactopyranose and 1,5-dideoxy-1,5-imino-D-galactitol, and their inhibition of alpha- and beta-D-galactosidases. Carbohydrate Res. 1986: 155:119-29.

Lembcke, B. et al. (1991) "Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II)" Res Exp Med, 191(6): 389-404.

Liu et al., "The Impact of Sialic Acids on the Pharmacokinetics of a PEGylated Erythropoietin," Journal of Pharmaceutical Sciences 101(12): 4414-4418 (2012).

Lun, Y. et al. (2015) "Histological examination of the effect of a highly phosphorylated proprietary recombinant human acid alpha-glucosidase on glycogen reduction in disease-relevant muscles of Pompe mice" Amicus Technologies: Poster from the Lysosomal Disease Network 11th WORLD Symposium, Feb. 9-13, 2015, Orlando, Florida; 1 page.

Lun, Y. et al. (2017) "A Novel Recombinant Human Acid Alpha-Glucosidase, ATB200, Leads to Greater Substrate Reduction and Improvement in Pompe Disease-Relevant Markers Compared to Alglucosidase Alfa in Gaa KO Mice" Amicus Technologies: Poster from the 13th Annual Lysosomal Disease Network WORLD Symposium, San Diego, CA, Feb. 13-17, 2017; 1 page.

Lun, Y. et al. (2017) "Stabilized Next-Generation Recombinant Human Acid Alpha-Glucosidase AT00 Clears Accumulated Glycogen and Reverses Cellular Dysfunction to Increase Muscle Strength in A Mouse Model of Pompe Disease" Amicus Therapeutics: Poster

(56) References Cited

OTHER PUBLICATIONS from the 2017 Muscular Dystrophy Association Scientific Conference, Mar. 19-11, 2017, Arlington, Virginia; 1 page.
Martiniuk et al., "Correction of Glycogen Storage Disease Type II by Enzyme Replacement with a Recombinant Human Acid Maltase Produced by Over-Expression in a CHO-HDFRneg Cell Line," Biochemical and Biophysical Research Communications, 276(3):917-923 (2000).
McVie-Wylie et al., "Biochemical and pharmacological characterization of different recombinant acid alpha-glucosidase preparations evaluated for the treatment of Pompe disease" Mol Genet Metab, 94(4):448-455 (2008).
Mellor et al., Cellular effects of deoxynojirimycin analogues; uptake, retention and inhibition of glycosphingolipid biosynthesis, Biochem J. 2004; 381:861-866.
Moreland et al, Lysosomal Acid alpha-Glucosidase Consists of Four Different Peptides Processed from a Single Chain Precursor, The Journal of Biological Chemistry, 2005, 280, pp. 6780-6791.
Nair et al., "A simple practice guide for dose conversion between animals and human," Journal of Basic and Clinical Pharmacy 7(2), 5 pages (2016).
National Institutes of Health Clinical Center. Patient Education: Giving a subcutaneous injection. Bethesda, MD: NIH Clinical Center, 2002., 3 pages.
Nilsson MI et al., Lysosomal alpha-glucosidase preproprotein [*Homo sapiens*], Accession No. NP_000143.2, dated Jun. 26, 2021, 4 pages.
Okumiya et al., "Chemical chaperones improve transport and enhance stability of mutant α-glucosidases in glycogen storage disease type II," Mol Genet Metab, 90(1):49-57 (2006).
Overkleeft et al., "Generation of Specific Deoxynojirimycin-type Inhibitors of the Non-lysosomal Glucosylceramidase," The Journal of Biological Chemistry, 273(41):26522-26527 (1998).
Parenti et al., "Lysosomal storage diseases: from pathophysiology to therapy. Annual review of medicine," 66:471-486 (2015).
Parenti et al., A Chaperone Enhances Blood α-Glucosidase Activity in Pompe Disease Patients Treated with Enzyme Replacement Therapy. Mol. Ther. 22(11):2004-2012 (2014).
Parenti, G., et al., Alpha-Glucosidase Enhancement in Fibroblasts from Patients with Pompe Disease, J. Inherit. Metab. Dis. 2005: 28(Suppl. 1):193, Abstract 383-P (2005), 1 page.
Platt, et al. Prevention of Lysosomal Storage in Tay-Sachs Mice Treated with N-butyldeoxynojirimycin, Science, 1997: 276:428-431.
Platt, et al., "N-Butyldeoxygalactonojirimycin Inhibits Glycolipid Biosynthesis but Does Not *Affect* N-Linked Oligosaccharide Processing," The Journal of Biological Chemistry, 269(43):27108-27114 (1994).
"Pompe Phase 1/2 Study (ATB200-02) Preliminary Data," Amicus Therapeutics, Dec. 8, 2016, pp. 1-13.
Porto et al., "The Pharmacological Chaperone N-butyldeoxynojirimycin Enhances Enzyme Replacement Therapy in Pompe Disease Fibroblasts," Mol Ther. 17(6):964-971 (2009).
Raben et al., Replacing acid alpha-glucosidase in Pompe disease: recombinant and transgenic enzymes are equipotent, but neither completely clears glycogen from type II muscle fibers. Mol Ther. 11(1):48-56 (2005).
Raben et al., "Deconstructing Pompe Disease by Analyzing Single Muscle Fibers," (2007) Autophagy 3:6, 546-552.
Roberts M et al., "First-in-Human Study of ATB200/AT2221 in Patients with Pompe Disease: Interim Results from the ATB200-02 Trial," The 22nd International Congress of the World Muscle Society, Oct. 3-7, 2017, St. Malo, France, 7 pages.
Ruvinov et al., Monovalent Cations Partially Repair a Conformational Defect in a Mutant Tryptophan Synthase α2β2 Complex (β-E109A). J. Biol. Chem., 1995; 270:17333-17338.
Sathe, S. et al. (2017) "Preliminary Safety, Pharmacokinetic, Pharmacodynamic, and Efficacy Data in Patients with Pompe Disease Receiving ATB200/AT2221 in First-in-Human Study" Amicus Therapeutics: Poster from the 4th International Glycogen Storage Disease (GSD) Conference, Jun. 15-17, 2017, University Medical Center, Groningen, The Netherlands; 1 page.
Sathe, S. et al. (2017) "Preliminary Pharmacokinetic and Safety Data in Patients with Pompe Disease in First-in-Human Study Receiving ATB200/AT2221" Amicus Therapeutics: Poster from the 2017 Muscular Dystrophy Association Scientific Conference, Mar. 19-11, 2017, Arlington, Virginia; 1 page.
Sola et al., "Glycosylation of Therapeutic Proteins: An Effective Strategy to Optimize Efficacy," BioDrugs., 2010, 24(1):9-21.
Stanley et al., "Essentials of Glycobiology," 2nd edition, Cold Spring Harbor (NY): Cold Spring Harbor Laboratory Press, Chapter 8, NCBI Bookshelf, 12 pages (2009).
Tajima, et al., "Structural and biochemical studies on Pompe disease and a "pseudodeficiency of acid α-glucosidase"". Journal of Human Genetics, 52(11), pp. 898-906 (2007).
Tarnopolsky et al.: "Pompe Disease: Diagnosis and Management. Evidence Based Guidelines from a Canadian Expert Panel", Canadian Journal of Neurological Sciences 43(4):472-485 (2016).
Valenzano, K.J. et al. (Jun. 2011) "Identification and characterization of pharmacological chaperones to correct enzyme deficiencies in lysosomal storage disorders" Assay and Drug Development Technologies, 9(3):213-235.
Van Der Ploeg et al., "Receptor-Mediated Uptake of Acid α-Glucosidase Corrects Lysosomal Glycogen Storage in Cultured Skeletal Muscle" Pediatric Research, 24(1):90-94 (1988).
Van Hove et al., Purification of recombinant human precursor acid α-glucosidase. Biochem. Mol. Biol. Int. 1997: 43(3):613-623.
Wilson, B.A. et al. (2003) Prentice Hall Nurse's Drug Guide 2003 Companion Website. [online]. Retrieved from: http://wps.prenhall.com/chet_wilson_drugguides_1 /6/1576/403472.cw/index.html; accessed Sep. 30, 2014, 1 page.
Winkel et al., "Enzyme Replacement Therapy in Late-Onset Pompe's Disease: A Three-Year Follow-up," Annual Neurol. 55(4):495_502_ 2004.
Xu et al., "Improved efficacy of a next-generation ERT in murine Pompe disease," JCI Insight, 2019, 4(5):e125358, 20 pages.
Zhou et al., "The Mechanistic Impact of N-Glycosylation on Stability, Pharmacokinetics, and Immunogenicity of Therapeutic Proteins," Journal of Pharmaceutical Sciences, 2019, 108:1366-1377.
"Amicus Therapeutics Announces Additional Positive Data in Pompe Disease Phase 1/2 Study at World Muscle Society," Amicus Therapeutics, Oct. 4, 2017, 4 pages.
Zhou, S., et al., "LC-MS/MS Analysis of Permethylated N-Glycans Facilitating Characterization," Anal Bioanal Chem, vol. 409(2), Oct. 28, 2016, pp. 453-466.
Khanna, Richie, et al., "The Pharmacological Chaperone AT2220 Increases the Specific Activity and Lysosomal Delivery of Mutant Acid Alpha-Glucosidase, and Promotes Glycogen Reduction in a Transgenic Mouse Model of Pompe Disease", PLoS ONE 9(7): e102092. doi:10.1371/journal.pone.0102092 (2014).
Parenti, Giancarlo, et al., "A Chaperone Enhances Blood α-Glucosidase Activity in Pompe Disease Patients Treated With Enzyme Replacement Therapy", Molecular Therapy vol. 22 No. 11 Nov. 2014, pp. 2004-2012.
"Opfolda US Label", 21 pgs, Sep. 2023.
"Opfolda—SmPC", 25 pgs Jun. 2023.
"POMBILITI—SmPC", 37 pgs. Mar. 2023.
"Pombiliti US Label", 24 pgs, Sep. 2023.
"World Symposium Investor Dinner Slides", Perspectives on Pompe: Progress, Persistence and Passion, Feb. 12, 2020, 41 pages.
Kalia, Jeet, et al., "Hydrolytic Stability of Hydrazones and Oximes", Angew Chem Int Ed Engl. 2008 ; 47(39): 7523-7526.
Kalia, Jeet, et al., "Hydrolytic Stability of Hydrazones and Oximes", Supporting Information, Anal. Chem. 1968, 40, 700-706.
Zhu, Yunxiang, et al., "Glycoengineered Acid α-Glucosidase With Improved Efficacy at Correcting the Metabolic Aberrations and Motor Function Deficits in a Mouse Model of Pompe Disease", The American Society of Gene Therapy, Molecular Therapy, vol. 17 No. 6, 954-963 Jun. 2009.
European Application No. 15845664.0, filed Apr. 6, 2017, by Amicus Therapeutics, Inc.: Supplementary European Search Report, mailed Feb. 12, 2018, 13 pages.

(56) References Cited

OTHER PUBLICATIONS

Nippon Rinsho, vol. 68, Suppl 8, pp. 665-669.
PCT International Search Report and Written Opinion mailed Jan. 6, 2016, in PCT/US2015/053252, 9 pages.
PCT International Search Report and Written Opinion mailed Mar. 7, 2017, in PCT/US2016/069243, 10 pages.
PCT International Search Report and Written Opinion mailed May 8, 2013, in PCT/US2013/029660, 8 pages.
PCT International Search Report and Written Opinion mailed Oct. 1, 2013, in PCT/US2013/039215, 9 pages.
"Center For Disease Control and Prevention (Data Table of Weight-for-age Charts. 2001, pp. 1-15).".
"Extended European Search Report for Application No. 20207542.0, mailed on Jul. 29, 2021, 11 pages.".
"Final Office Action in U.S. Appl. No. 11/440,473, dated Jan. 5, 2015, 8 pages.".
"Final Office Action in U.S. Appl. No. 11/440,473, dated May 15, 2009, 8 pages.".
"Final Office Action in U.S. Appl. No. 11/440,473, dated May 19, 2010, 7 pages".
"Final Office Action in U.S. Appl. No. 11/440,473, dated May 9, 2011, 8 pages.".
"International Search Report and Written Opinion issued in International Application No. PCT/US2017/024981, dated Aug. 3, 2017, 27 pages".
"Non-Final Office Action in U.S. Appl. No. 11/440,473, dated Dec. 5, 2008, 8 pages.".
"Non-Final Office Action in U.S. Appl. No. 11/440,473, dated Mar. 28, 2014, 9 pages".
"Non-Final Office Action in U.S. Appl. No. 11/440,473, dated May 7, 2008, 8 pages.".
"Non-Final Office Action in U.S. Appl. No. 11/440,473, dated Sep. 14, 2009, 6 pages.".
"Non-Final Office Action in U.S. Appl. No. 11/440,473, dated Sep. 30, 2010 , 8 pages".
"Non-Final Office Action in U.S. Appl. No. 17/665,179, dated Jul. 11, 2022, 15 pages.".
"Non-Final Office Action in U.S. Appl. No. 14/379,131, dated Sep. 15, 2015, 9 pages.".
"The extended European search report dated Jan. 27, 2021, issued in European Application No. 20177473.4, 11 pages.".
Chavez, et al., "Domain 5 of the Cation-Independent Man nose 6-Phosphate Receptor Preferentially Binds Phosphodiesters (Man nose 6-Phosphate N-Acetylglucosamine Ester).", Biochemistry (2007), 46: 12604-12617.
Chien , et al., "Pompe Disease: Early Diagnosis and Early Treatment Make a Difference", Pediatrics and Neonatology, 2013, 54, pp. 219-227.
Hoja-Lukowicz, Dorota , et al., "Characterization of the oligosaccharide component of microsomal [beta]-glucuronidase from rat liver", Biochimie, FR, (20040601), vol. 86, No. 6, pp. 363-372.
Jongen, S P, et al., (2007) "N-glycans of recombinant human acid [alpha]-glucosidase expressed in the milk of transgenic rabbits", Database Embase Accession No. EMB-2007342042, Elsevier Science Publishers, (Glycobiology 17(6):600-619).
Khanna, R. , et al., "Molecular Genetics and Metabolism", vol. 117, Issue 2, Feb. 2016, pp. S66-S67. doi:10.1016/j.ymgme.2015.12.318).
Nagase, T., et al., "Synthetic construct DNA, clone: pF1KB4173, Homo sapiens GAA gene for lysosomal alpha-glucosidase precursor, complete cds, without stop codon, in Flexi system", Accession: AB384912.1.
Shin-Buehring, Y.S. , et al., "Separation of acid and neutral a-glucosidase isoenzymes from fetal and adult tissues, cultivated fibroblasts and amniotic fluid cells by DEAE-cellulose and Sephadex G-100 column chromatography", Clinica Chimica Acta 89(3):393-404, 12 pages (1978).
Sugawara, Kanako , et al., "Structural modeling of mutant rt-glucosidases resulting in a processing/transport defect in Pompe disease", Journal of Human Genetics (2009) 54, 624-330.
Toonkool, P, et al., (2006) "Expression and purification of dalcochinase, a beta-glucosidase from Dalbergia cochinchinensis Pierre, in yeast and bacterial hosts", Protein Expression and Purification, 48(2): 195-204.
Block, et al., "Immobilized-metal affinity chromatography (IMAC): a review", Methods Enzymol. 2009; 463: 439-73.

\* cited by examiner

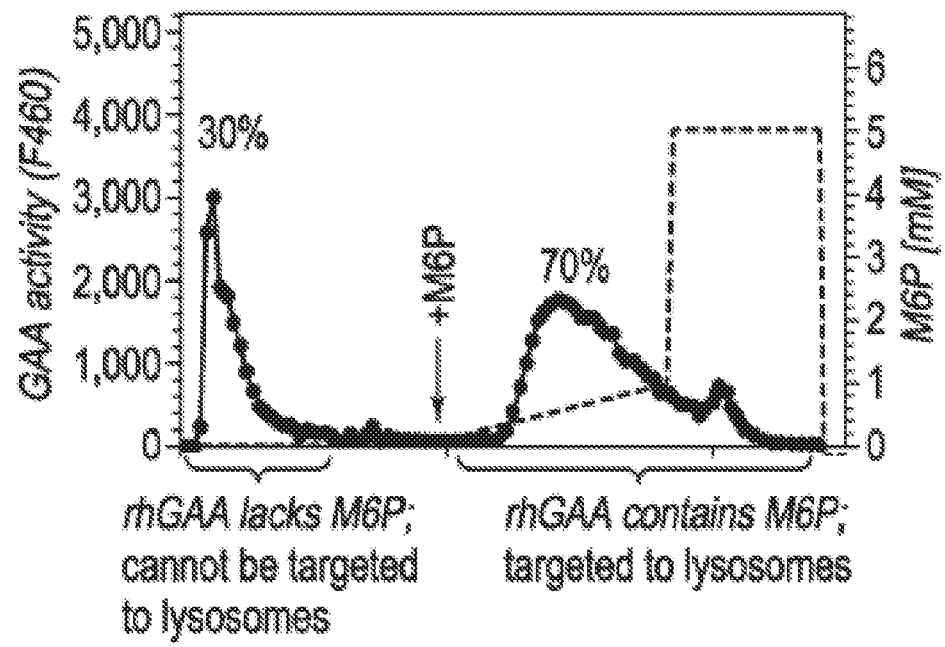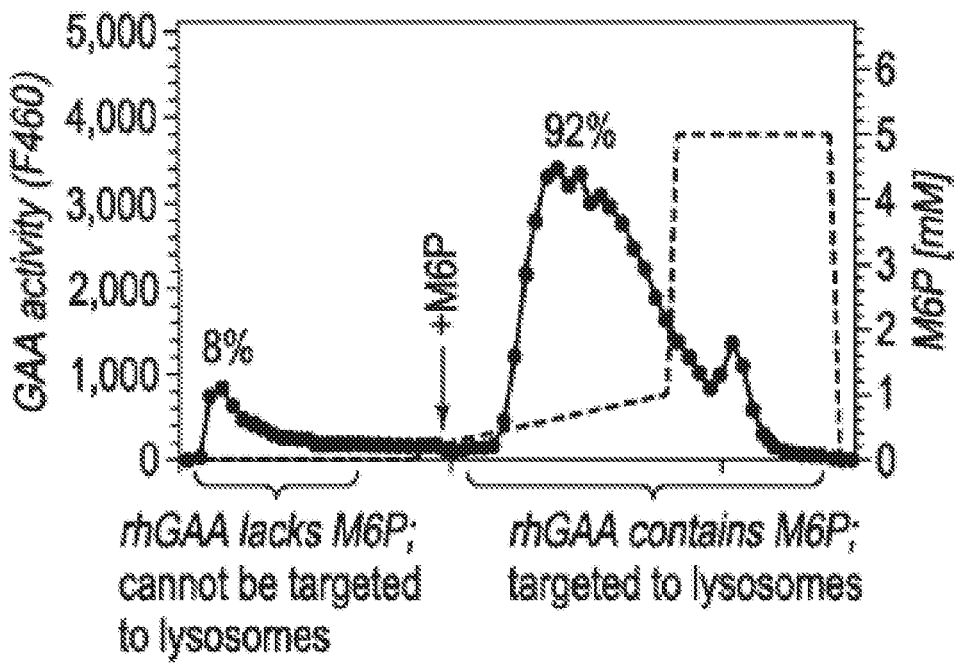
Fig. 5

Distribution of N-Glycans on rhGAA Preparations

| | Lumizyme | BP-rhGAA* | ATB200 1 | ATB200 2 |
|---|---|---|---|---|
| Complex Type N-Glycans | 70.7% | 48.9% | 51.0% | 47.5% |
| Hybrid Type N-Glycans | 6.7% | 9.7% | 4.4% | 3.7% |
| High Mannose Type N-Glycans: | | | | |
| Non-phosphorylated | 15.8% | 23.7% | 14.0% | 9.9% |
| Mono-M6P | 5.2% | 10.4% | 13.4% | 14.2% |
| Bis-M6P | 1.8% | 6.6% | 17.2% | 24.7% |

Fig. 8

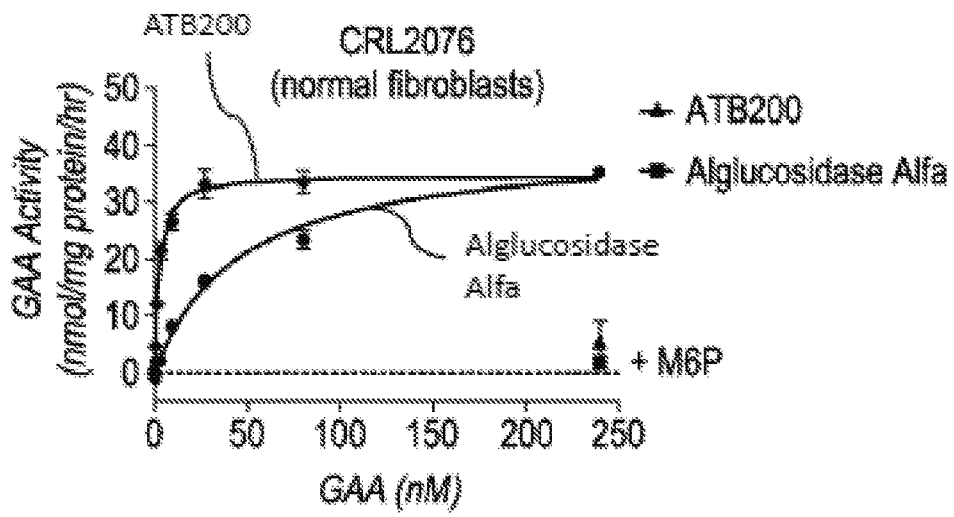
Fig. 11A
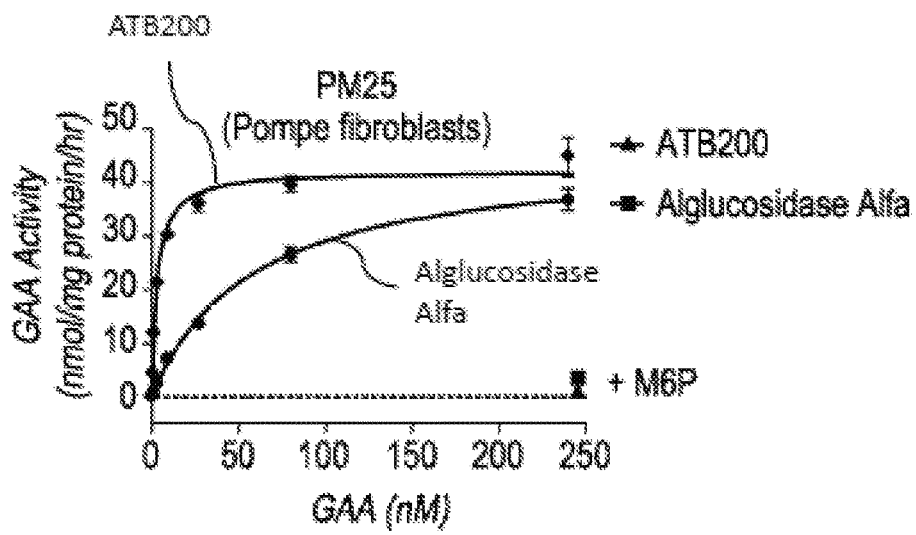
Fig. 11B
| Cell Line | $K_{uptake}$ (nM) | |
|---|---|---|
| | AT200 | Lumizyme |
| normal | 2 | 56 |
| Pompe | 3 | 57 |
Fig. 11C

Baseline Characteristics (N=20)

| | Cohort 1 ERT-Naïve Ambulatory (N=11) | Cohort 2 ERT-Experienced Non-ambulatory (N=4) | Cohort 3 ERT-Naïve (N=5) |
|---|---|---|---|
| Age, years, mean (min, max) | 49.4 (28, 66) | 36.0 (18, 56) | 49.4 (24, 65) |
| Sex, M:F | 9:2 | 3:1 | 1:4 |
| Time on alglucosidase alfa, years, mean (SD) | 4.8 (1.42)a | 8.9 (3.8) | NA |
| 6MWT, meters, mean (SD) | 392.0 (93.4) | NA | 399.5 (83.5) |
| FVC Upright, % predicted, mean (SD) | 52.3 (13.2) | NA | 53.4 (20.3) |

NA=not applicable; SD=standard deviation.
a Cohort 1 patients were required to have been on alglucosidase alfa for 2+ years at baseline.

Fig. 19C

AT2221 Pharmacokinetics Summary

| Treatment | $C_{max}$ (ng/mL)[a] | $t_{max}$ (h)[b] | $AUC_{\tau}$ (ng·h/mL)[a] | $AUC_{\infty}$ (ng·h/mL)[a] | $t_{1/2}$ (h)[a] | CL/F (L/h)[a] | $V_z/F$ (L)[a] |
|---|---|---|---|---|---|---|---|
| Low Dose MD (N=11) | 1504 (23.9) | 3.0 (1.5-4.0) | 11,968 (24.5) | 12,913 (25.6) | 6.5 (29.3) | 10.3 (21.3) | 97.3 (39.8) |
| High Dose MD (N=16) | 3086 (29.4) | 3.0 (1.0-4.0) | 24,095 (25.9) | 25,506 (25.9) | 5.9 (18.3) | 10.5 (22.9) | 90.5 (34.1) |

CL/F=plasma clearance adjusted for AT2221 oral bioavailability; $V_z/F$ =apparent terminal phase volume of distribution adjusted for AT2221 oral bioavailability.
[a]Geometric mean (CV%). [b]Median (min-max). [c]Arithmetic mean (CV%).

Fig. 20

Total GAA Protein by Signature Peptide T09

| Cohort | Treatment | $C_{max}$ (ng/mL)[a] | $T_{max}$ (hr)[b] | $AUC_{0-last}$ (ng·hr/mL)[a] | $AUC_{\infty}$ (ng·hr/mL)[a] | $F_{rel}$[c] | $\alpha\, t_{1/2}$ (hr) | $CL_t$ (L/hr) |
|---|---|---|---|---|---|---|---|---|
| 1 | ATB200 5 mg/kg alone[d] | 58.4 (19.1) | 4.0 (3.0-4.0) | 108 (25.1) | 211 (17.2) | — | 1.1 (19.2) | 2.2 (16.9) |
| 1 | ATB200 10 mg/kg alone[d] | 135 (18.3) | 4.0 (3.5-4.0) | 287 (25.6) | 538 (24.4) | 2.6 (9.4) | 1.3 (10.6) | 1.7 (22.4) |
| 1 | ATB200 20 mg/kg alone[d] | 325 (13.5) | 4.0 (3.5-4.0) | 844 (20.8) | 1418 (16.9) | 6.9 (7.4) | 1.5 (8.5) | 1.3 (18.4) |
| 1 | ATB200 20 mg/kg + AT2221 low dose MD[e] | 335 (15.4) | 4.0 (3.5-5.0) | 1062 (23.8) | 1662 (20.5) | 1.17 (7.7) | 1.8 (21.8) | 1.1 (20.5) |
| 1 | ATB200 20 mg/kg + AT2221 high dose MD[e] | 345 (18.5) | 4.0 (3.5-4.0) | 1203 (24.2) | 1831 (21.5) | 1.28 (9.4) | 2.1 (16.1) | 1.0 (22.7) |
| 3 | ATB200 20 mg/kg + AT2221 high dose MD[e] | 322 (14.3) | 4.0 (4.0-4.5) | 1147 (20.9) | 1775 (19.3) | N/A | 2.2 (9.9) | 0.8 (28.4) |

AUC=area under the curve; $CL_t$=total body clearance; $C_{max}$=maximum drug concentration; CV=coefficient of variability; MD=multiple doses; $t_{1/2}$=half-life; $T_{max}$=time to maximum drug concentration; $F_{rel}$=AUC Ratio of 20 mg/kg and 10 mg/kg vs 5 mg/kg, and 20 mg/kg + low dose or high dose AT2221 vs 20 mg/kg alone.
[a]Geometric mean (CV%). [b]Median (min-max). [c]Arithmetic mean (CV%). [d]n=11. [e]n=5.

Fig. 21

ANOVA for Total GAA Protein by Signature Peptide T09

| Reference | Test | AUC Ratio % Ref | 90% Lower bound CI | 90% Upper bound CI |
|---|---|---|---|---|
| Cohort 1 SD | Cohort 1 MD | 98.0 | 94.9 | 101.2 |
| Cohort 1 SD | Cohort 3 SD | 100.1 | 82.3 | 121.8 |
| Cohort 1 MD | Cohort 3 MD | 97.5 | 80.2 | 118.6 |

AUC=area under the curve; CI=confidence interval.

Fig. 23

6-Minute Walk Test

| | 6-Minute Walk Test (m); mean (SD) | | | |
|---|---|---|---|---|
| Cohort 1 ERT-switch Ambulatory | Baseline (n=10) | CFBL M6 (n=10) | CFBL M9 (n=10) | CFBL M12 (n=8) |
| | 397.2 (96.8) | +23.9 (52.2) | +24.5 (40.8) | +57.4 (34.4) |
| Cohort 3 ERT-Naïve | Baseline (n=5) | CFBL M6 (n=5) | CFBL M9 (n=5) | CFBL M12 (n=2) |
| | 399.5 (83.5) | +41.8 (29.4) | +63.5 (23.1) | +86.8 (11.1) |

> 6MWT increased in 7/10, 8/10, and 8/8 ERT-switch patients at Months 6, 9 and 12 respectively
> 6MWT increased in 5/5, 5/5, and 2/2 ERT-naïve patients at Months 6, 9 and 12 respectively

Fig. 24A

| Patient | Baseline | Change From Baseline | | |
|---|---|---|---|---|
| | | Month 6 | Month 9 | Month 12 |
| Cohort 1 Ambulatory ERT-Switch | | | | |
| 1 | 544 | +51 | +56 | +112 |
| 2 | 379 | +125 | +110 | +103 |
| 3 | 339 | +21 | +45 | +73 |
| 4 | 332 | +8 | +26 | +45 |
| 5 | 456 | -5 | +8 | +41 |
| 6 | 500 | +65 | +20 | +33 |
| 7 | 220 | +29 | +21 | +30 |
| 8 | 410 | +38 | +11 | +22 |
| 9 | 464 | -4 | -9 | — |
| 10 | 328 | -78 | -43 | — |
| Mean (SD) | 397.2 (96.8) | +23.9 (52.2) | +24.5 (40.8) | +57.4 (34.4) |
| Cohort 3 ERT-Naïve | | | | |
| 1 | 480 | +41 | +72 | +95 |
| 2 | 384 | +62 | +78 | +79 |
| 3 | 460 | +79 | +89 | — |
| 4 | 406 | +14 | +44 | — |
| 5 | 267 | +13 | +35 | — |
| Mean (SD) | 399.5 (83.5) | +41.8 (29.4) | +63.5 (23.1) | +86.8 (11.1) |

Fig. 24B

Other Motor Function Tests

| | Assessment, sec | Baseline, Mean (SD) | Change From Baseline to Month 6, Mean (SD) | Change From Baseline to Month 9, Mean (SD) | Change From Baseline to Month 12, Mean (SD) |
|---|---|---|---|---|---|
| Cohort 1 ERT-Switch | | n=10 | n=10 | n=10 | n=8 |
| | Timed Up and Go | 10.5 (6.6) | -1.8 (3.5) | -1.2 (3.3) | -1.0 (2.2) |
| | 4-Stair Climb | 4.1 (2.7) | -0.6 (1.6) | -0.4 (1.6) | -1.0 (1.5) |
| | 10M Walk | 7.4 (3.0) | +0.1 (1.9) | -0.1 (1.6) | -0.5 (1.7) |
| | Gowers[a] | 7.9 (2.9) | -1.1 (3.8) | 4.5[b] (13.4) | -2.6 (1.9) |
| | GSGC Score | 12.6 (4.8) | +0.1 (3.9) | +0.5 (4.6) | -1.9 (2.2) |
| Cohort 3 ERT-Naïve | | n=5 | n=5 | n=5 | n=2 |
| | Timed Up and Go | 9.4 (2.9) | -1.0 (1.1) | -0.6 (1.4) | -1.8 (0.5) |
| | 4-Stair Climb | 4.2 (1.5) | -0.6 (0.3) | 0.0 (1.5) | -0.4 (0.4) |
| | 10M Walk | 7.9 (3.0) | -0.7 (1.1) | -1.3 (1.0) | -0.6 (0.0) |
| | Gowers | 13.9 (11.0) | 7.9[c] (20.9) | -1.6 (3.9) | -2.1 (1.3) |
| | GSGC Score | 12.2 (3.6) | -1.8 (3.8) | -2.4 (3.4) | 0.0 (1.4) |

GSGC=Gait, Stairs, Gowers, Chair.
GSGC is an observer-rated combined score of 4 motor function assessments: Gait (10m walk), 4-Stair Climb, Gowers (stand from floor), and Rising From Chair. Each test is scored from 1 (normal) to 7 (cannot perform, max score of 6 for Rising From Chair). Total scores range from 4 to 27.
[a] N=9, missing values not obtained due to patient refusal to perform test.
[b] Median change from baseline was -1.5, and 7/9 patients had a decrease.
[c] Median change from baseline was -0.8, and 4/5 patients had a decrease.

Fig. 24C

Muscle Strength Testing (QMT) in Cohort 2 Patients

| Muscle Group Tested | Baseline Mean (SD) n=1 | Change from Baseline to Month 6 Mean (SD) n=1 | Change from Baseline to Month 9 Mean (SD) n=1 |
|---|---|---|---|
| Quantitative Muscle Testing Dominant Side | | | |
| Shoulder Adduction* | 5.7 (8.8) | +8.1 (12.8) | +9.6 (12.3) |
| Shoulder Abduction | 16.7 (18.1) | +1.0 (6.6) | +6.5 (9.3) |
| Elbow Flexion | 12.7 (13.7) | +2.4 (15.9) | +6.0 (19.3) |
| Elbow Extension | 12.3 (13.9) | +5.3 (4.7) | +7.5 (8.2) |
| Manual Muscle Testing Medical side | | | |
| Shoulder Adduction* | 5.7 (8.8) | +8.1 (12.8) | +9.6 (12.3) |
| Shoulder Abduction | 16.7 (18.1) | +1.0 (6.6) | +6.5 (9.3) |
| Elbow Flexion | 12.7 (13.7) | +2.4 (15.9) | +6.0 (19.3) |
| Elbow Extension | 12.3 (13.9) | +5.3 (4.7) | +7.5 (8.2) |

Measure is in pounds of force for right and left sides combined.
*Shoulder adduction not evaluated for 1 patient.
Scoring: (1) Visible muscle movement, but no movement at the joint; (2) Movement at the joint, but not against gravity; (3) Movement against gravity, but not against added resistance; (4) Movement against resistance, but less than normal; (5) Normal strength.

Fig. 25

Manual Muscle Test Score in Cohort 1: ERT-Switch Ambulatory Patients

Increases were observed in manual muscle strength in ERT-switch patients at Months 6, 9, and 12

| | Body Area | Baseline | | Change From Baseline | | | | | |
|---|---|---|---|---|---|---|---|---|---|
| | | | | Month 6 | | Month 9 | | Month 12 | |
| | | mean (SD) | n | mean (SD) | n | mean (SD) | n | mean (SD) | n |
| Cohort 1 ERT-Switch Ambulatory | Upper Body Max score 40 | 35.4 (5.7) | 10 | +1.2 (2.4) | 10 | +1.7 (2.8) | 10 | +2.8 (3.9) | 8 |
| | Lower Body Max score 40 | 31.0 (3.0) | 10 | +0.9 (1.8) | 9 | +2.2 (2.4) | 10 | +2.3 (2.9) | 8 |
| | Total Body Max score 80 | 66.4 (8.1) | 10 | +2.8 (3.4) | 10 | +4.0 (3.1) | 10 | +4.5 (2.8) | 8 |

Fig. 26A

Manual Muscle Test Score in Cohort 2: ERT-Switch Nonambulatory Patients

Increases were observed in manual muscle strength in ERT-switch nonambulatory patients at Months 6 and 9

| | Body Area | Baseline | | Change From Baseline | | | |
|---|---|---|---|---|---|---|---|
| | | | | Month 6 | | Month 9 | |
| | | mean (SD) | n | mean (SD) | n | mean (SD) | n |
| Cohort 2 ERT-Switch Nonambulatory | Upper Body Max score 40 | 13.3 (12.2) | 3 | +5.7 (2.1) | 3 | +2.3 (5.5) | 3 |

Fig. 26B

Manual Muscle Test Score in Cohort 3: ERT-Naive Patients

Increases were observed in manual muscle strength in ERT-naive patients at Months 6, 9, and 12

| | Body Area | Baseline | | Change From Baseline | | | | | |
|---|---|---|---|---|---|---|---|---|---|
| | | | | Month 6 | | Month 9 | | Month 12 | |
| | | mean (SD) | n | mean (SD) | n | mean (SD) | n | mean (SD) | n |
| Cohort 3 ERT-Naive | Upper Body Max score 40 | 36.8 (3.4) | 5 | −0.2 (1.3) | 5 | +0.8 (1.9) | 5 | −0.5 (0.7) | 2 |
| | Lower Body Max score 40 | 29.0 (2.0) | 4 | +0.5 (1.9) | 4 | +1.3 (3.6) | 4 | +4.5 (0.7) | 2 |
| | Total Body Max score 80 | 66.9 (3.7) | 5 | −0.7 (3.2) | 5 | +1.3 (3.1) | 5 | +4.0 (1.4) | 2 |

Fig. 26C

Pulmonary Function Tests: FVC, MIP, MEP

| Assessment | Baseline Mean (SD) | Change from Baseline to Month 4, Mean (SD) | Change from Baseline to Month 9, Mean (SD) | Change from Baseline to Month 12, Mean (SD) |
|---|---|---|---|---|
| Cohort 1 Expansion | | | | |
| FVC, % predicted* | 32.6 (14.7) | -1.3 (4.1) | -1.7 (3.9) | -3.1 (4.8) |
| MIP | 35.7 (11.0) | +0.3 (4.6) | -0.6 (3.0) | +0.3 (0.6) |
| MEP | 72.6 (32.6) | +16.1 (42.1) | +23.7 (38.1) | +36.3 (45.7) |
| Cohort 2 Expansion | | | | |
| FVC, % predicted* | 53.4 (20.3) | +4.2 (5.6) | +6.2 (5.3) | +6.0 (7.1) |
| MIP | 32.6 (18.5) | +11.0 (5.0) | +12.0 (10.3) | -0.5 (9.2) |
| MEP | 50.6 (8.3) | -0.4 (12.4) | +2.2 (15.3) | -2.0 (9.9) |

SD=standard deviation; MIP=maximal inspiratory pressure; MEP=maximal expiratory pressure.
*FVC not available for 1 patient.
MIP and MEP were measured in centimeters of water.

Fig. 27

Mean Percentage Change From Baseline in Markers of Muscle Damage in Cohort 1 Patients Mean Percentage Change From Baseline in Markers of
(A) Muscle Damage (Creatine Kinase) and
(B) Glycogen Accumulation (Urine Hexose Tetrasaccharide)
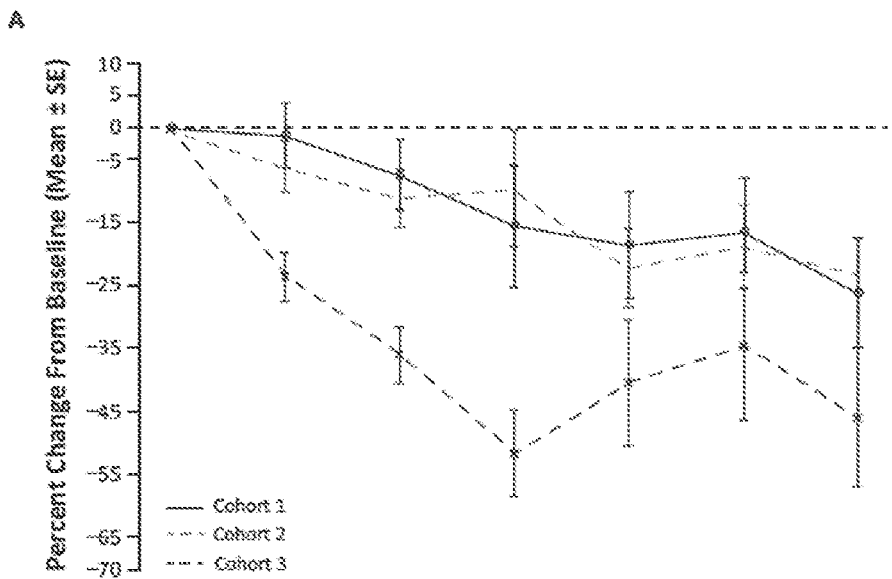
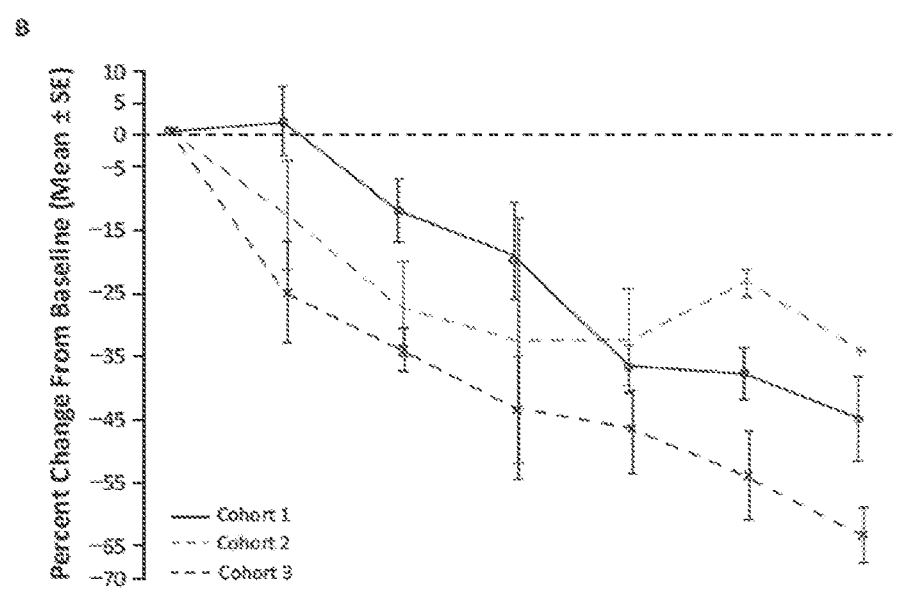
Fig. 29D

Safety Summary (N=20)[a]

Safety profile of AT-GAA/ATB200/AT2221 through the interim data cut is generally mild and transient with no discontinuations of AT-GAA treatment due to infusion-associated reactions

- AEs were generally mild and transient
  - The most common treatment-emergent AEs were abdominal pain[b] (8/20), diarrhea (8/20), nasopharyngitis (6/20), nausea (5/20), headache (5/20), and upper respiratory tract infection (5/20)
- 3 incidents of IARs in 550+ infusions, which were controlled by standard premedication
  - 1 IAR event in a nonambulatory ERT-switch patient (skin discoloration)
  - 2 IAR events in a ERT-naïve patient (localized pruritus; erythema and burning sensation)
- Longest duration of treatment is 20+ months AE, adverse events; IAR, infusion-associated reaction.
[a]Reported through interim data analysis (maximum 20+ months).
[b]Includes upper and lower abdominal pain.

Fig. 30

Conclusions

- Muscle function
  - 6MWT distance continued to improve in ERT-switch ambulatory and ERT-naïve patients out to Month 12
  - Other motor function tests were consistent with 6MWT results in both cohorts
  - Increases were observed in manual muscle strength in all cohorts
  - Increases in elbow and shoulder muscle strength in nonambulatory ERT-switch patients at Months 6 and 9
- Pulmonary function
  - FVC, MIP, and MEP were generally stable in ERT-switch patients
  - FVC, MIP, and MEP generally increased in ERT-naïve patients
- Fatigue Severity Scale
  - Improvement in fatigue score observed in all cohorts
- Biomarkers and safety
  - CK and Hex4 levels decreased in all cohorts
  - ATB200/AT2221 was generally well tolerated

Fig. 31

Site Specific Glycan Summary

| | N84 | | N177 | | N334 | | N414 | | N596 | | N826 | | N869 | |
|---|---|---|---|---|---|---|---|---|---|---|---|---|---|---|
| | Average | Stdev | Average | Stdev | Average | Stdev | Average | Stdev | Average | Stdev | Average | Stdev | Average | Stdev |
| Phosphorylated Glycans | 83.2% | 5.4% | 48.9% | 3.0% | ND | | 87.4% | 3.1% | ND | | 2.1% | 0.1% | ND | |
| Mono-Phohosphorylated | 25.6% | 2.8% | 48.0% | 2.9% | ND | | 35.3% | 1.6% | ND | | 2.1% | 0.1% | ND | |
| Bis-phosphorylated | 57.6% | 2.6% | 1.0% | 0.1% | ND | | 52.0% | 1.5% | ND | | ND | | ND | |
| Sialylated Glycans | 25.0% | 3.3% | 6.2% | 0.6% | 54.6% | 4.9% | 11.2% | 1.2% | 70.4% | | 85.4% | 10.5% | 86.7% | 10.8% |
| Fully Sialylated | 13.7% | 2.0% | 6.2% | 0.6% | 19.3% | 2.3% | 8.6% | 1.0% | 26.0% | | 26.6% | 4.0% | 7.6% | 1.4% |
| High Mannose | 64.9% | 3.1% | 88.9% | 4.1% | 14.4% | 1.4% | 84.7% | 2.8% | 0.1% | 0.0% | 2.1% | 0.1% | ND | |
| Hybrid | 18.7% | 2.3% | 10.9% | 1.4% | ND | | 5.2% | 0.6% | ND | | ND | | ND | |
| Complex | 16.4% | 2.4% | 0.2% | 0.0% | 85.6% | 9.0% | 10.1% | 1.2% | 99.9% | 11.8% | 97.9% | 13.9% | 100.0% | 14.3% |
| Number of Glycans | 24 | | 17 | | 39 | | 22 | | 25 | | 39 | | 46 | |
| M6P (mol/mol Site) | 1.36 | | 0.50 | | | | 1.38 | | | | 0.02 | | | |
| mono Glycan (mol/mol site) | 0.25 | | 0.48 | | | | 0.35 | | | | 0.02 | | | |
| bis Glycan (mol/mol site) | 0.56 | | 0.01 | | | | 0.52 | | | | | | | |
| Sialic Acid (mol/mol Site) | 0.32 | 0.04 | 0.06 | 0.01 | 0.97 | 0.06 | 0.074 | 0.004 | 0.86 | 0.07 | 4.2 | 0.1 | 0.86 | 0.07 |
| Site Occupancy | 96.5% | 0.2% | 99.9% | 0.0% | 100.0% | 0.0% | 99.3% | 0.7% | 84.9% | 1.1% | 98.6% | 0.1% | 41.0% | 0.8% |

ND = Not Detected

Fig. 33B

RECOMBINANT HUMAN ACID ALPHA-GLUCOSIDASE

CROSS-REFERENCE TO RELATED APPLICATIONS

This application is the United States national stage entry under 35 U.S.C. § 371 of International Application No. PCT/US2018/032815, filed May 15, 2018 and published as WO 2018/213340 A1, which claims the benefit of U.S. Provisional Application Ser. No. 62/506,561 filed May 15, 2017, U.S. Provisional Application Ser. No. 62/506,569 filed May 15, 2017, U.S. Provisional Application Ser. No. 62/506,574 filed May 15, 2017, U.S. Provisional Application Ser. No. 62/529,300 filed Jul. 6, 2017, U.S. Provisional Application Ser. No. 62/564,083 filed Sep. 27, 2017, U.S. Provisional Application Ser. No. 62/567,334 filed Oct. 3, 2017, U.S. Provisional Application Ser. No. 62/618,021 filed Jan. 16, 2018, U.S. Provisional Application Ser. No. 62/624,638 filed Jan. 31, 2018, and U.S. Provisional Application Ser. No. 62/660,758 filed Apr. 20, 2018, to each of which priority is claimed and each of which is incorporated by reference in its entirety.

FIELD OF INVENTION

The present invention involves the fields of medicine, genetics and recombinant glycoprotein biochemistry, and, specifically, relates to recombinant human α-glucosidase (rhGAA) compositions that have a higher total content of mannose-6-phosphate-bearing N-glycans that efficiently target CIMPR on cells and subsequently deliver rhGAA to the lysosomes where it can break down abnormally high levels of accumulated glycogen. The rhGAA of the invention exhibits superior uptake into muscle cells and subsequent delivery to lysosomes compared to conventional rhGAA products and exhibits other pharmacokinetic properties that make it particularly effective for enzyme replacement therapy of subjects having Pompe disease.

The present invention also provides a method for treating Pompe disease comprising administering to an individual a combination of an rhGAA and a pharmacological chaperone. For example, in some embodiments, the present invention provides a method for treating Pompe disease comprising administering to an individual a combination of rhGAA and miglustat. The rhGAA of the invention exhibits surprising efficacy in treating and reversing disease progression in subjects suffering from Pompe disease.

BACKGROUND

Pompe disease is an inherited lysosomal storage disease that results from a deficiency in acid α-glucosidase (GAA) activity. A person having Pompe Disease lacks or has reduced levels of acid α-glucosidase (GAA), the enzyme which breaks down glycogen to glucose, a main energy source for muscles. This enzyme deficiency causes excess glycogen accumulation in the lysosomes, which are intracellular organelles containing enzymes that ordinarily break down glycogen and other cellular debris or waste products. Glycogen accumulation in certain tissues of a subject having Pompe Disease, especially muscles, impairs the ability of cells to function normally. In Pompe Disease, glycogen is not properly metabolized and progressively accumulates in the lysosomes, especially in skeletal muscle cells and, in the infant onset form of the disease, in cardiac muscle cells. The accumulation of glycogen damages the muscle and nerve cells as well as those in other affected tissues.

Traditionally, depending on the age of onset, Pompe disease is clinically recognized as either an early infantile form or as a late onset form. The age of onset tends to parallel the severity of the genetic mutation causing Pompe Disease. The most severe genetic mutations cause complete loss of GAA activity and manifest as early onset disease during infancy. Genetic mutations that diminish GAA activity but do not completely eliminate it are associated with forms of Pompe disease having delayed onset and progression. Infantile onset Pompe disease manifests shortly after birth and is characterized by muscular weakness, respiratory insufficiency and cardiac failure. Untreated, it is usually fatal within two years. Juvenile and adult onset Pompe disease manifest later in life and usually progress more slowly than infantile onset disease. This form of the disease, while it generally does not affect the heart, may also result in death, due to weakening of skeletal muscles and those involved in respiration.

Current non-palliative treatment of Pompe disease involves enzyme replacement therapy (ERT) using recombinant human GAA (rhGAA) known as Lumizyme®, Myozyme®, or alglucosidase alfa. This conventional enzyme replacement therapy seeks to treat Pompe Disease by replacing the missing GAA in lysosomes by administering rhGAA thus restoring the ability of cells to break down lysosomal glycogen. "Lumizyme®" and "Myozyme®" are conventional forms of rhGAA produced or marketed as biologics by Genzyme and approved by the U.S. Food and Drug Administration, and are described by reference to the Physician's Desk Reference (2014) (which is hereby incorporated by reference). Alglucosidase alfa is identified as chemical name [199-arginine, 223-histidine]prepro-α-glucosidase (human); molecular formula, $C_{4758}H_{7262}N_{1274}O_{1369}S_{35}$; CAS number 420794-05-0. These products are administered to subjects with Pompe Disease, also known as glycogen storage disease type II (GSD-II) or acid maltase deficiency disease.

The cellular uptake of a rhGAA molecule is facilitated by the specialized carbohydrate, mannose-6-phosphate (M6P), which binds to the cation-independent mannose-6-phosphate receptor (CIMPR) present on target cells such as muscle cells. Upon binding, rhGAA molecule is taken up by target cells and subsequently transported into the lysosomes within the cells. Most of the conventional rhGAA products, however, lack a high total content of mono-M6P- and bis-M6P-bearing N-glycans (i.e., N-glycans bearing one M6P residue or N-glycans bearing two M6P residues, respectively), which limits their cellular uptake via CIMPR and lysosomal delivery, thus making conventional enzyme replacement therapy insufficiently effective. For example, while conventional rhGAA products at 20 mg/kg or higher doses do ameliorate some aspects of Pompe disease, they are not able to adequately, among other things, (i) treat the underlying cellular dysfunction, (ii) restore muscle structure, or (iii) reduce accumulated glycogen in many target tissues, such as skeletal muscles, to reverse disease progression. Further, higher doses may impose additional burdens on the subject as well as medical professionals treating the subject, such as lengthening the infusion time needed to administer rhGAA intravenously. There remains a need for further improvements to enzyme replacement therapy for treatment of Pompe disease, such as rhGAA with improved tissue uptake, improved enzymatic activity, improved stability, or reduced immunogenicity.

The glycosylation of GAA or rhGAA can be enzymatically modified in vitro by the phosphotransferase and uncovering enzymes described by Canfield, et al., U.S. Pat. No. 6,534,300, to generate M6P groups. Enzymatic glycosylation cannot be adequately controlled and can produce rhGAA having undesirable immunological and pharmacological properties. Enzymatically modified rhGAA may contain only high-mannose oligosaccharide which all could be potentially enzymatically phosphorylated in vitro with a phosphotransferase or uncovering enzyme and may contain on average 5-6 M6P groups per GAA. The glycosylation patterns produced by in vitro enzymatic treatment of GAA are problematic because the additional terminal mannose residues, particularly non-phosphorylated terminal mannose residues, negatively affect the pharmacokinetics of the modified rhGAA. When such an enzymatically modified product is administered in vivo, these mannose groups increase non-productive clearance of the GAA, increase the uptake of the enzymatically-modified GAA by immune cells, and reduce rhGAA therapeutic efficacy due to less of the GAA reaching targeted tissues, such as skeletal muscle myocytes. For example, terminal non-phosphorylated mannose residues are known ligands for mannose receptors in the liver and spleen which leads to rapid clearance of the enzymatically-modified rhGAA and reduced targeting of rhGAA to target tissue. Moreover, the glycosylation pattern of enzymatically-modified GAA having high mannose N-glycans with terminal non-phosphorylated mannose residues resembles that on glycoproteins produced in yeasts and molds, and increases the risk of triggering immune or allergic responses, such as life-threatening severe allergic (anaphylactic) or hypersensitivity reactions, to the enzymatically modified rhGAA.

In view of these deficiencies of conventional rhGAA products and in vitro methods to phosphorylate rhGAA, the inventors diligently sought and identified ways to produce rhGAA with an optimized N-glycan profile for enhanced biodistribution and lysosomal uptake and thereby to minimize non-productive clearance of rhGAA once administered. The present invention provides stable or declining Pompe patients an effective therapy that reverse disease progression at the cellular level. The inventors also report that the rhGAA of the present invention reverses the disease progression—including clearing lysosomal glycogen more efficiently than the current standard of care—and that patients treated with the rhGAA of the present invention exhibit surprising and significant health improvements, including improvements in muscle strength, motor function, and/or pulmonary function, and/or including a reversal in disease progression, as demonstrated in various efficacy results (e.g., Examples 10 and 11) from the clinical studies.

SUMMARY

The present invention relates to a method of treating a disease or disorder such as Pompe disease in a subject, comprising administering a population of recombinant human acid α-glucosidase (rhGAA) molecules.

The rhGAA molecules described herein may be expressed in Chinese hamster ovary (CHO) cells and comprise seven potential N-glycosylation sites. In some embodiments, the N-glycosylation profile of a population of rhGAA molecules as described herein is determined using liquid chromatography-tandem mass spectrometry (LC-MS/MS). In some embodiments, the rhGAA molecules on average comprise 3-4 mannose-6-phosphate (M6P) residues. In some embodiments, the rhGAA molecules on average comprise about at least 0.5 mol bis-phosphorylated N-glycan groups (bis-M6P) per mol of rhGAA at the first potential N-glycosylation site. In some embodiments, the rhGAA comprises an amino acid sequence at least 95% identical to SEQ ID NO: 1 or SEQ ID NO: 5. In some embodiments, the rhGAA comprises an amino acid sequence identical to SEQ ID NO: 1 or SEQ ID NO: 5. In embodiments, at least 30% of molecules of the rhGAA molecules comprise one or mote N-glycan units bearing one or two M6P residues. In some embodiments, the rhGAA molecules comprise on average from about 0.5 mol to about 7.0 mol of N-glycan units bearing one or two M6P residues per mol of rhGAA. In some embodiments, the rhGAA molecules comprises on average at least 2.5 moles of M6P residues per mol of rhGAA and at least 4 mol of sialic acid residues per mol of rhGAA. In some embodiments, the rhGAA molecules comprising an average of 3-4 M6P residues per molecule and an average of about at least 0.5 mol bis-M6P per mol rhGAA at the first potential N-glycosylation site further comprise an average of about 0.4 to about 0.6 mol mono-phosphorylated N-glycans (mono-M6P) per mol rhGAA at the second potential N-glycosylation site, about 0.4 to about 0.6 mol bis-M6P per mol rhGAA at the fourth potential N-glycosylation site, and about 0.3 to about 0.4 mol mono-M6P per mol rhGAA at the fourth potential N-glycosylation site. In some embodiments, the rhGAA molecules further comprise on average about 4 mol to about 7.3 mol of sialic acid residues per mol of rhGAA, including about 0.9 to about 1.2 mol sialic acid per mol rhGAA at the third potential N-glycosylation site, about 0.8 to about 0.9 mol sialic acid per mol rhGAA at the fifth potential N-glycosylation site, and about 1.5 to about 4.2 mol sialic acid per mol rhGAA at the sixth potential N-glycosylation site. In some embodiments, the population of rhGAA molecules is formulated in a pharmaceutical composition. In some embodiments, the pharmaceutical composition comprising a population of rhGAA molecules further comprises at least one buffer selected from the group consisting of a citrate, a phosphate, and a combination thereof, and at least one excipient selected from the group consisting of mannitol, polysorbate 80, and a combination thereof. In some embodiments, the pH of the pharmaceutical composition is about 5.0 to about 7.0, about 5.0 to about 6.0, or about 6.0. In some embodiments, the pharmaceutical composition further comprises water, an acidifying agent, an alkalizing agent, or a combination thereof. In some embodiments, the pharmaceutical composition has a pH of 6.0 and comprises about 5-50 mg/mL of the population of rhGAA molecules, about 10-100 mM of a sodium citrate buffer, about 10-50 mg/mL mannitol, about 0.1-1 mg/mL polysorbate 80, and water, and optionally comprises an acidifying agent and/or alkalizing agent. In some embodiments, the pharmaceutical composition has a pH of 6.0 and comprises about 15 mg/mL of the population of rhGAA molecules, about 25 mM of a sodium citrate buffer, about 20 mg/mL mannitol, about 0.5 mg/mL polysorbate 80, and water, and optionally comprises an acidifying agent and/or alkalizing agent.

In some embodiments, the population of rhGAA molecules is administered at a dose of about 1 mg/kg to about 100 mg/kg. In some embodiments, the population of rhGAA molecules is administered at a dose of about 20 mg/kg. In some embodiments, the population of rhGAA molecules is administered bimonthly, monthly, bi-weekly, weekly, twice weekly, or daily, for example, bi-weekly. In some embodiments, the population of rhGAA molecules is administered intravenously.

In some embodiments, the population of rhGAA molecules is administered concurrently or sequentially with a pharmacological chaperone such as miglustat (also referred to as AT2221) or a pharmaceutically acceptable salt thereof. In some embodiments, the miglustat or pharmaceutically acceptable salt thereof is administered orally, for example at a dose of about 200 mg to about 600 mg, and optionally about 260 mg. In some embodiments, the population of rhGAA molecules is administered intravenously at a dose of about 5 mg/kg to about 20 mg/kg and the miglustat or pharmaceutically acceptable salt thereof is administered orally at a dose of about 233 mg to about 500 mg. In some embodiments, the the population of rhGAA molecules is administered intravenously at a dose of about 5 mg/kg to about 20 mg/kg and the miglustat or pharmaceutically acceptable salt thereof is administered orally at a dose of about 50 mg to about 200 mg. In one embodiment, the population of rhGAA molecules is administered intravenously at a dose of about 20 mg/kg and the miglustat or pharmaceutically acceptable salt thereof is administered orally at a dose of about 260 mg. In some embodiments, the miglustat or pharmaceutically acceptable salt thereof is administered prior to (for example, about one hour prior to administration of the population of rhGAA molecules. In at least one embodiment, the subject fasts for at least two hours before and at least two hours after the administration of miglustat or a pharmaceutically acceptable salt thereof.

Embodiments of the invention demonstrate the efficacy of the rhGAA described herein to treat and reverse disease progression in a subject with Pompe disease.

In some embodiments, the population of rhGAA molecules is administered at a dosage capable of reversing disease progression a subject. For example, after treatment, a muscle or muscle fiber in the subject exhibits reduced lysosomal size and/or a resolution of autophagic buildup. In some embodiments, after treatment fewer than 65% of muscle fibers analyzed in the subject have autophagic buildup. In some embodiments, after treatment at least 36% of muscle fibers analyzed in the subject have normal or near-normal appearance. In some embodiments, the subject experiencing a reversal in disease progression after treatment is an ERT-switch patient, for example an ERT-switch patient who had previously been treated with alglucosidase alfa for at least two years.

In some embodiments, the population of rhGAA molecules is administered at a dosage capable of reducing glycogen content in a muscle of the subject faster than the same dosage of alglucosidase alfa. The rhGAA may reduce glycogen content at least about 1.25, 1.5, 1.75, 2.0, or 3.0 times faster than the same dosage of alglucosidase alfa. In some embodiments, the population of rhGAA molecules is administered at a dosage further capable of reducing glycogen content in a muscle of the subject more effectively than alglucosidase alfa administered at the same dosage when assessed after one, two, three, four, five, or six administrations. In some embodiments, the population of rhGAA molecules reduces glycogen content at least about 10%, 20%, 30%, 50%, 75%, or 90% more effectively than does alglucosidase alfa administered at the same dosage. In some embodiments, after treatment the subject exhibits lower levels of the glycogen accumulation biomarker urine hexose tetrasaccharide (Hex4). In at least one embodiment, Hex4 levels in the subject are reduced at least 30% six months after treatment relative to baseline. For example, an ambulatory or nonambulatory subject previously treated with enzyme replacement therapy (an ERT-switch patient) may exhibit a reduction in Hex4 levels of at least 35% at six months after treatment relative to baseline. In another instance, an ambulatory subject who has not previously received enzyme replacement therapy (an ERT-naïve patient) may exhibit a reduction in Hex4 levels of at least 45% at six months after treatment relative to baseline.

In some embodiments, the population of rhGAA molecules is administered at a dosage capable of improving motor function in the subject. Improvement in motor function may be measured by a motor function test such as a six-minute walk test (6MWT), a timed up and go test, a four-stair climb test, a ten-meter walk test, a gowers test, a gait-stair-gower-chair (GSGC) test, or a combination thereof. In some embodiments, the subject six months after treatment (when compared to baseline) shows a 6MWT distance increase of at least 20 meters, a timed up and go test time decrease of at least 1 second, a four-stair climb test time decrease of at least 0.6 seconds, a ten-meter walk test time decrease of at least 0.7 seconds, a gowers test time decrease of at least 1 second, and/or a GCSC score decrease of at least 1. For example, an ambulatory ERT-switch patient, six months after treatment (compared to baseline), may exhibit a 6MWT increase of at least 20 meters, a timed up and go test time decrease of at least 1.5 seconds, a four-stair climb test time decrease of at least 0.6 seconds, and/or a gowers test time decrease of at least 1 second. In another instance, an ambulatory ERT-naïve patient, six months after treatment (compared to baseline), may exhibit a 6MWT distance increase of at least 40 meters, a timed up and go test time decrease of at least 1 second, a four-stair climb test time decrease of at least 0.6 seconds, a ten-meter walk test time decrease of at least 0.7 seconds, and/or a GSGC score decrease of at least 1. In some embodiments, an ERT-switch patient exhibits an improvement in at least one motor function test after treatment relative to the patient's motor function test result after a previous ERT with alglucosidase alfa.

In some embodiments, the population of rhGAA molecules is administered at a dosage capable of improving upper body strength in the subject. In some embodiments, the population of rhGAA molecules is administered to an ambulatory subject and is further capable of improving lower body strength and/or total body strength in the subject.

In some embodiments, the improvement in upper body strength is measuring using a manual muscle strength score. A subject's manual muscle strength score may improve by at least 1 (for an ambulatory ERT-switch patient) or at least 5.5 (for a nonambulatory ERT-switch patient) at six months after treatment relative to baseline. In some embodiments, an ERT-switch patient exhibits an improvement in upper body strength after treatment relative to the patient's upper body strength after a previous ERT with alglucosidase alfa.

In some embodiments, the population of rhGAA molecules is administered at a dosage capable of improving upper extremity strength as measure by quantitative muscle testing or manual muscle testing of shoulder adduction, should abduction, elbow flexion, and/or elbow-extension. For example, at six months after treatment relative to baseline, a nonambulatory ERT-switch patient may exhibit an improvement in shoulder adduction of at least 8 pounds of force, an improvement in shoulder abduction of at least 1 pound of force, an improvement in elbow flexion of at least 2 pounds of force, and/or an improvement in elbow extension of at least 5 pounds of force.

In some embodiments, the population of rhGAA molecules is administered at a dosage capable of improving pulmonary function in the subject. Improvement in motor function may be measured by a pulmonary function test such as an upright (sitting) forced vital capacity test, a a maximal expiratory pressure (MEP) test, a maximal inspiratory pressure (MIP) test, or a combination thereof. In some embodiments, the subject six months after treatment (when compared to baseline) shows an improvement in FVC of at least 4%, an improvement in MEP of at least 16 cmH$_2$O, and/or an improvement in MIP of at least 0.3 cmH$_2$O. For example, an ambulatory ERT-switch patient, six months after treatment (compared to baseline), may exhibit an improvement in MEP of at least 16 cmH$_2$O. In another instance, an ambulatory ERT-naïve patient, six months after treatment (compared to baseline), may exhibit an improvement in FVC of at least 4% and/or an improvement in MIP of at least 11 cmH$_2$O. In some embodiments, an ERT-switch patient exhibits an improvement in at least one pulmonary function test after treatment relative to the patient's pulmonary function test result after a previous ERT with alglucosidase alfa.

In some embodiments, the population of rhGAA molecules is administered at a dosage capable of reducing fatigue in the subject, as measured according to a fatigue severity scale (FSS) score. For example, the subject may be a nonambulatory ERT-switch patient and exhibit an FSS score decrease of at least 3.5 at six months after treatment relative to baseline. In another example, the subject may be an ambulatory ERT-switch patient and exhibit an FSS score decrease of at least 8 at six months after treatment relative to baseline. In yet another example, the subject may be an ambulatory ERT-naïve patient and exhibit an FSS score decrease of at least 5 at six months after treatment relative to baseline. In some embodiments, an ERT-switch patient exhibits a lower FSS score after treatment relative to the patient's FSS score after a previous ERT with alglucosidase alfa.

In some embodiments, the population of rhGAA molecules is administered at a dosage capable of reducing the levels of at least one biomarker of muscle injury, for example creatine kinase (CK), alanine aminotransferase (ALT), aspartate aminotransferase (AST), or a combination thereof. In some embodiments, the subject's CK levels at six months after treatment are reduced at least 15% relative to baseline, the subject's ALT levels at six months after treatment are reduced at least 5% relative to baseline, and/or the subject's AST levels at six months after treatment are reduced at least 5% relative to baseline. For example, the subject may be an ambulatory ERT-switch patient and exhibit a reduction in CK levels of at least 15%, a reduction in ALT levels of at least 15%, and/or a reduction in AST levels of at least 10% at six months after treatment relative to baseline. In another example, the subject may be a nonambulatory ERT-switch patient and exhibit a reduction in CK levels of at least 20%, a reduction in ALT levels of at least 5%, and/or a reduction in AST levels of at least 5% at six months after treatment relative to baseline. In yet another example, the subject may be an ambulatory ERT-naïve patient and exhibit a reduction in CK levels of at least 35%, a reduction in ALT levels of at least 35%, and/or a reduction in AST levels of at least 30% at six months after treatment relative to baseline.

BRIEF DESCRIPTION OF THE DRAWINGS

FIG. 5 is a graph showing the results of CIMPR affinity chromatography of ATB200 rhGAA with (Embodiment 2) and without (Embodiment 1) capture on an anion exchange (AEX) column.

FIG. 6A shows the site occupancy of the seven potential N-glycosylation sites for ATB200. FIG. 6B shows two analyses of the N-glycosylation profile of the first potential N-glycosylation site for ATB200. FIG. 6C shows two analyses of the N-glycosylation profile of the second potential N-glycosylation site for ATB200. FIG. 6D shows two analyses of the N-glycosylation profile of the third potential N-glycosylation site for ATB200. FIG. 6E shows two analyses of the N-glycosylation profile of the fourth potential N-glycosylation site for ATB200. FIG. 6F shows two analyses of the N-glycosylation profile of the fifth potential N-glycosylation site for ATB200. FIG. 6G shows two analyses of the N-glycosylation profile of the sixth potential N-glycosylation site for ATB200. FIG. 6H summarizes the relative percent monophosphorylated and bis-phosphorylated species for the first, second, third, fourth, fifth, and sixth potential N-glycosylation sites.

FIG. 8 is a table showing a summary of N-glycan structures of Lumizyme® compared to three different preparations of ATB200 rhGAA, identified as BP-rhGAA, ATB200-1 and ATB200-2.

FIG. 11A is a graph comparing ATB200 rhGAA activity (left trace) with Lumizyme® rhGAA activity (right trace) inside normal fibroblasts at various GAA concentrations. FIG. 11B is a table comparing ATB200 rhGAA activity (left trace) with Lumizyme® rhGAA activity (right trace) inside fibroblasts from a subject having Pompe Disease at various GAA concentrations. FIG. 11C is a table comparing $K_{uptake}$ of fibroblasts from normal subjects and subjects with Pompe Disease.

In FIG. 26A, "6MWT"=6-minute walk test; "FVC"=forced vital capacity; "QOW"=every other week, "a"=safety data from 2 sentinel patients from Cohort 1 were reviewed at each dose level before dosing in Cohorts 2 and 3; "b"=during stages 2 and 3, AT2221 was orally administered prior to the start of ATB200 intravenous infusion. For all doses, ATB200 was intravenously infused for a 4-hour duration, "c"=the first 2 patients in Cohorts 2 and 3 served as sentinel patients for their respective cohorts. FIG. 19C summarizes the baseline characteristics of patients enrolled across Cohorts 1, 2, and 3. "NA"=not applicable. "SD"=standard deviation, "a"=Cohort 1 patients were required to have been on alglucosidase alfa for 2-6 years at baseline. LOPD=late onset Pompe disease.

FIG. 20 depicts pharmacokinetic data for AT2221. "AUC"=area under the curve; "CL/F"=plasma clearance adjusted for AT2221 oral bioavailability; "$C_{max}$"=maximum drug concentration; "CV"=coefficient of variability; "$t_{1/2}$"=half-life; "$t_{max}$"=time to maximum drug concentration; "$V_z/F$"=apparent terminal phase volume of distribution adjusted for AT2221 oral bioavailability, "a"=geometric mean (CV %); "b"=median (min-max); "c"=arithmetic mean (CV %).

FIG. 21 depicts total GAA protein by signature peptide T09 for Cohorts 1 and 3. "AUC"=area under the curve; "$CL_T$"=total body clearance; "$C_{max}$"=maximum drug concentration; "CV"=coefficient of variability; "MD"=multiple doses; "$t_{1/2}$"=half-life; "$t_{max}$"=time to maximum drug concentration; "$F_{rel}$"=AUC Ratio of 20 mg/kg ATB 200 alone and 10 mg/kg ATB200 alone versus 5 mg/kg ATB200 alone, and 20 mg/kg ATB200+low dose or high dose AT2221 versus 20 mg/kg ATB200 alone, "a"=geometric mean (CV %); "b"=median (min-max); "c"=arithmetic mean (CV %); "d"=n=11; "e"=n=5. Low dose=130 mg. High dose=260 mg.

FIG. 22A shows the mean total GAA protein concentration-time profiles for Cohort 1 (single dose). FIG. 22B shows the mean total GAA protein concentration-time profiles for Cohort 1 (multiple dose). FIG. 22C shows the mean total GAA protein concentration-time profiles for Cohort 1 vs Cohort 3 (single dose). FIG. 22D shows the mean total GAA protein concentration-time profiles for Cohort 1 vs Cohort 3 (multiple dose). FIG. 22E shows total GAA protein comparisons to 20 mg/kg ATB200 at 12 hours post-dose; *=p<0.05; =p<0.01; * p<0.001. FIG. 22F shows total GAA protein comparisons to 20 mg/kg ATB200 at 24 hours post-dose; *=p<0.05; **=p<0.01; "ns"=not significant.

FIG. 23 shows an analysis of variance (ANOVA) for total GAA protein by signature peptide T09. The area under the curve (AUC) is provided in µg·h/mL; "CI"=confidence interval.

FIG. 24A depicts a summary of the analyses and available interim data from the 6-Minute Walk Test ("6MWT"), showing the change from baseline ("CFBL") at month 6, month 9, and month 12 for patients in Cohort 1 and Cohort 3.

FIG. 24B depicts 6MWT data for individual Cohort 1 and Cohort 3 patients.

FIG. 24C depicts a summary of the analysis and available interim data from other motor function tests: the Timed up and Go motor function test; the 4-stair climb test; the ten-meter (10M) walk test; gowers; and the gait-stair-gower-chair ("GSGC") motor function test, showing the change from baseline ("CFBL") at month 6, month 9, and month 12 for patients in Cohort 1 and Cohort 3. GSGC is an observer-rated combined score of four motor function assessments: gait (10-meter walk), 4-stair climb, gowers (stand from floor), and rising from chair. Each test is scored from 1 (normal) to 7 (cannot perform; max score of 6 for rising from chair test). Total scores range from 4 to 27. "a"=n=9, missing values not obtained due to patient refusal to perform test; "b"=median change from baseline was −1.5, and 7/9 patients had a decrease; "c"=median change from baseline was −0.8, and 4/5 patients had a decrease.

FIG. 25 depicts a summary of the analysis and available interim data from Muscle Strength Testing (QMT), showing the change from baseline ("CFBL") at month 6 and month 9 for patients in Cohort 2. QMT=quantified muscle test. The values shown represent pounds of force for right and left sides combined, "a"=shoulder adduction not available for one subject; "b"=scoring: (1) visible muscle movement, but no movement at the joint; (2) movement at the joint, but not against gravity; (3) movement against gravity, but not against added resistance; (4) movement against resistance, but less than normal; (5) normal strength.

FIG. 26A depicts of summary of the analysis and available interim data from manual muscle test (MMT) scores in Cohort 1 patients. MMT scores were calculated for upper body (maximum score: 40), lower body (maximum score: 40), and total body (maximum score: 80). Increases in manual muscle strength were observed in Cohort 1 patients at months 6, 9, and 12. "SD"=standard deviation.

FIG. 26B depicts of summary of the analysis and available interim data from manual muscle test (MMT) scores in Cohort 2 patients. MMT scores w ere calculated for upper body (maximum score: 40). Increases in manual muscle strength were observed in Cohort 2 patients at months 6 and 9. "SD"=standard deviation. MMT results were generally consistent with QMT results (shown in FIG. 28).

FIG. 26C depicts of summary of the analysis and available interim data from manual muscle test (MMT) scores in Cohort 3 patients. MMT scores were calculated for upper body (maximum score: 40), lower body (maximum score:

40), and total body (maximum score: 80). Increases in manual muscle strength were observed in Cohort 3 patients at each of months 6, 9, and 12. "SD"=standard deviation.

FIG. 27 depicts a summary of the analysis and available interim data from sitting forced vital capacity ("FVC"), maximal inspiratory pressure ("MIP"), and maximal expiratory-pressure ("MEP"), showing the change from baseline ("CFBL") at month 6, month 9, and month 12 for patients in Cohort 1 and Cohort 3. "a"=FVC not available for one subject. MEP and MIP were measured in cmH$_2$O.

Figure 28:
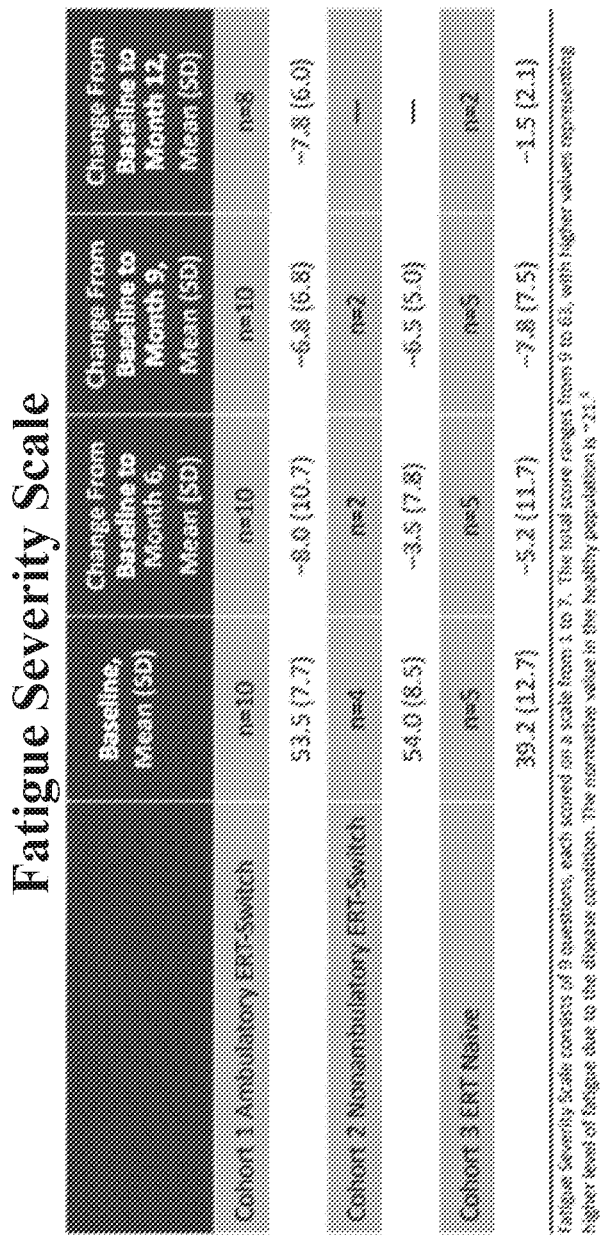

FIG. 28 depicts a summary of the analysis and available interim data from the Fatigue Severity Scale ("FSS"), a self-assessment questionnaire consisting of nine questions, each scored on a scale of 1 to 7. The total score ranges from 9 to 63, with higher values representing higher level of fatigue due to the disease condition. The normative value in the healthy population is ~21. FIG. 28 shows the change from baseline ("CFBL") at month 6, month 9, and month 12 for patients in Cohort 1, Cohort 2, and Cohort 3.

Figure 29A:
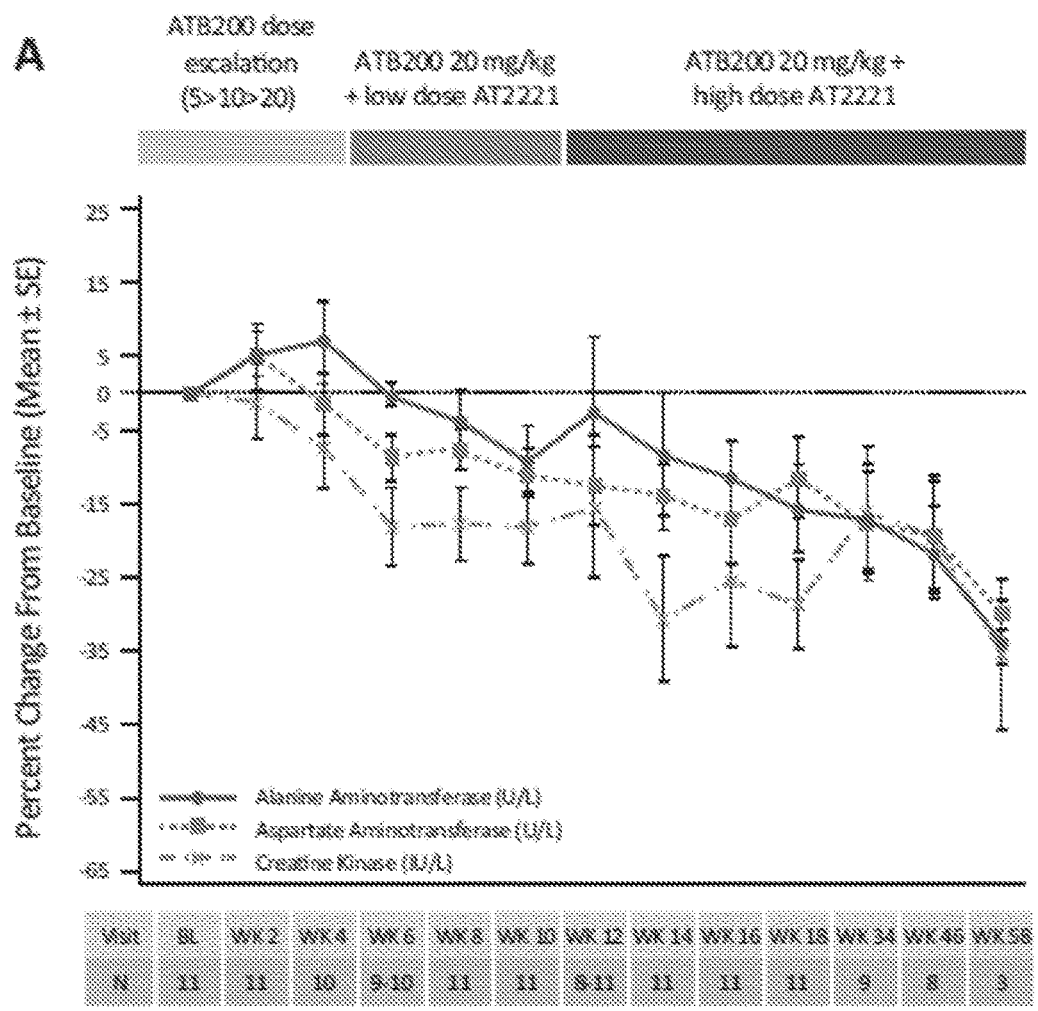
Figure 29B:
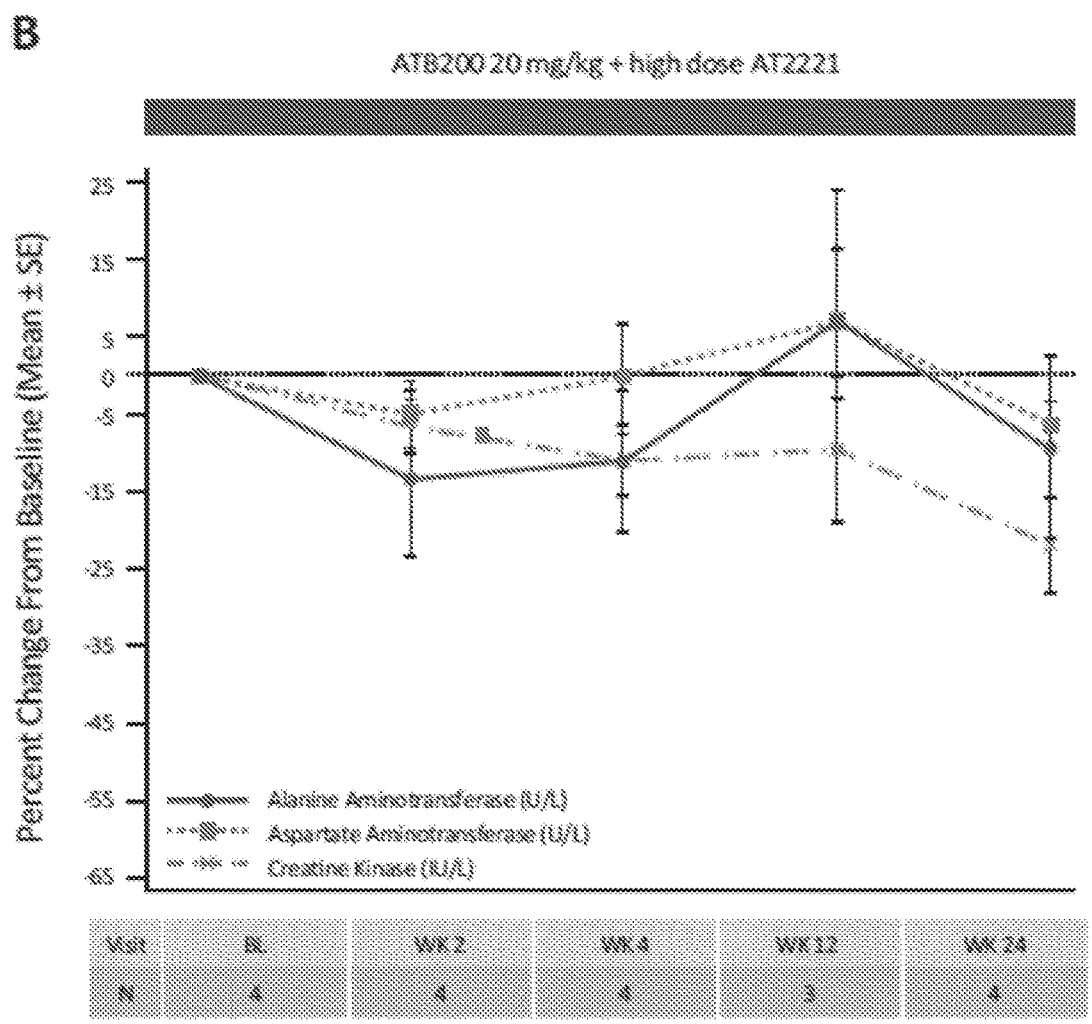
Figure 29C:
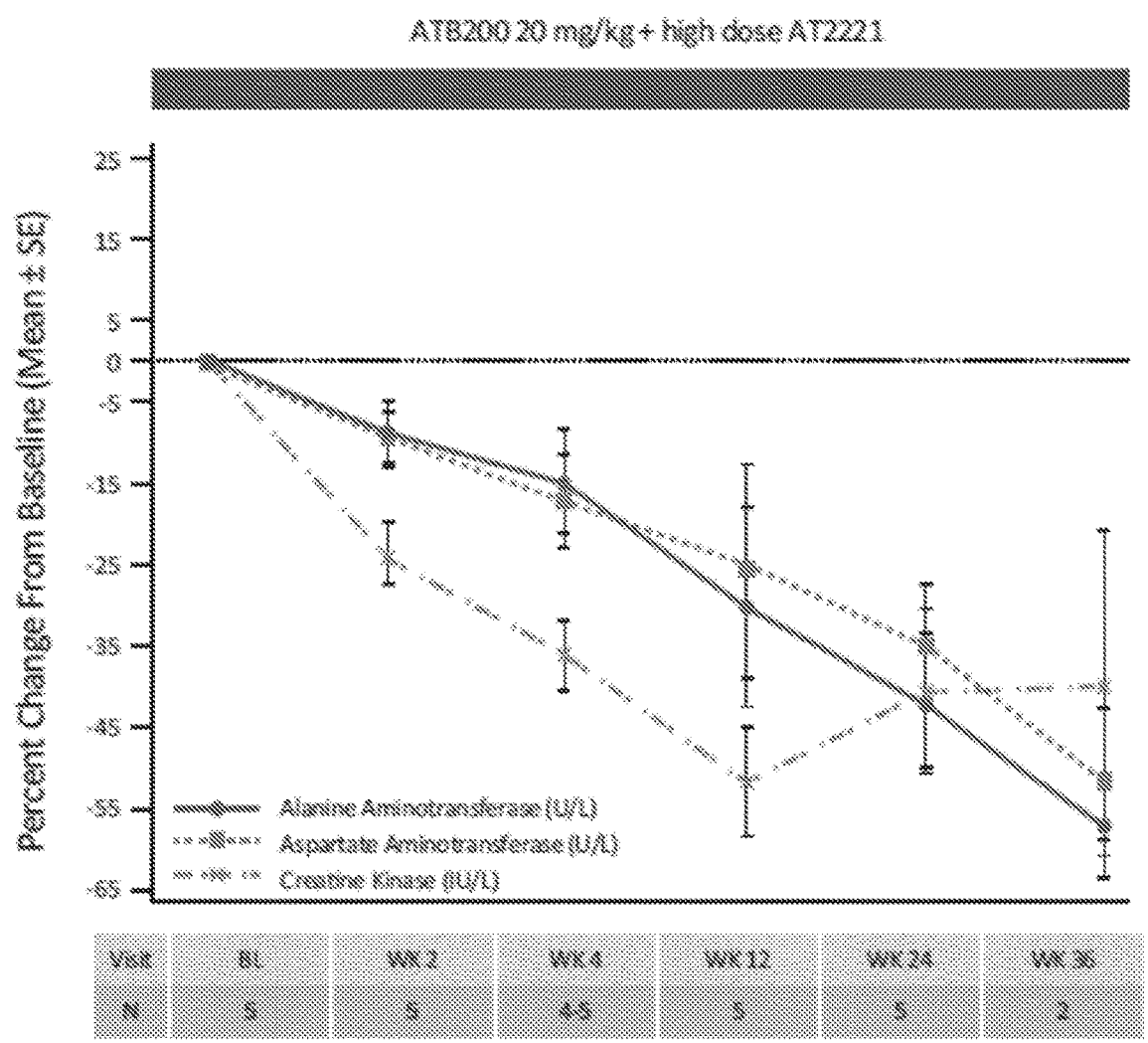

FIGS. 29A-29C depict the mean percentage change from baseline in markers of marker injury (alanine aminotransferase, aspartate aminotransferase, and creatine kinase) in all patient cohorts. FIG. 29A depicts data from Cohort 1 patients over 58 weeks, FIG. 29B depicts data from Cohort 2 patients over 24 weeks, and FIG. 29C depicts data from Cohort 3 patients over 36 weeks. FIG. 29D depicts the mean percentage change from baseline in markers of muscle injury (CK=creatine kinase) and disease substrate (Hex4=urine hexose tetrasaccharide) for up to 12 months for patients in Cohort 1, Cohort 2, and Cohort 3. "BL"=baseline. "SE"=standard error. "WK"=week. "M"=month.

FIG. 30 summarizes safety data from the ATB200-02 study. "AE"=adverse events. "IAR"=infusion-associated reaction; "a"=Reported through interim data analysis (maximum 204-months); "b"=Includes upper and lower abdominal pain.

FIG. 31 summarizes available efficacy and safety data from the ATB200-02 study.

FIGS. 32A-32H show the results of a site-specific N-glycosylation analysis of ATB200 rhGAA, including an N-glycosylation profile for the seventh potential N-glycosylation site, using LC/MS-MS analysis of protease-digested ATB200. FIGS. 32A-32H provide average data for ten lots of ATB200 produced at different scales.

Figure 32A:
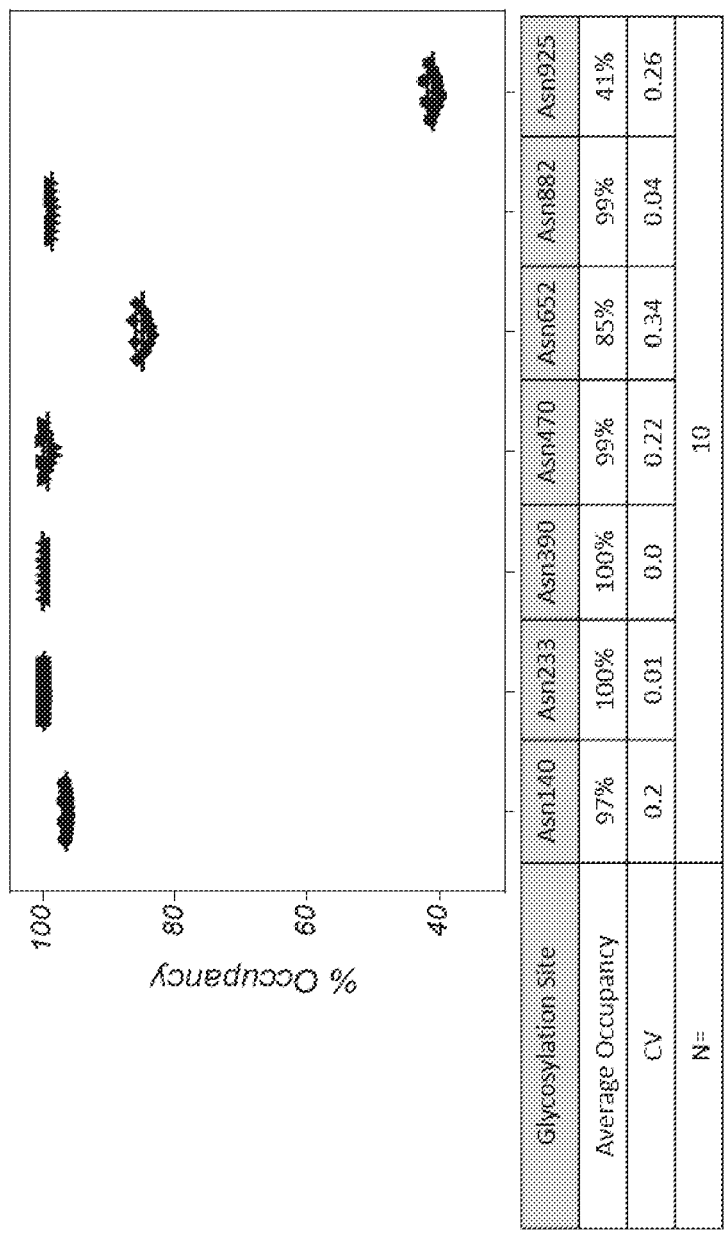

FIG. 32A shows the average site occupancy of the seven potential N-glycosylation sites for ATB200. The N-glycosylation sites are provided according to SEQ ID NO: 1. CV=coefficient of variation.

Figure 32B:
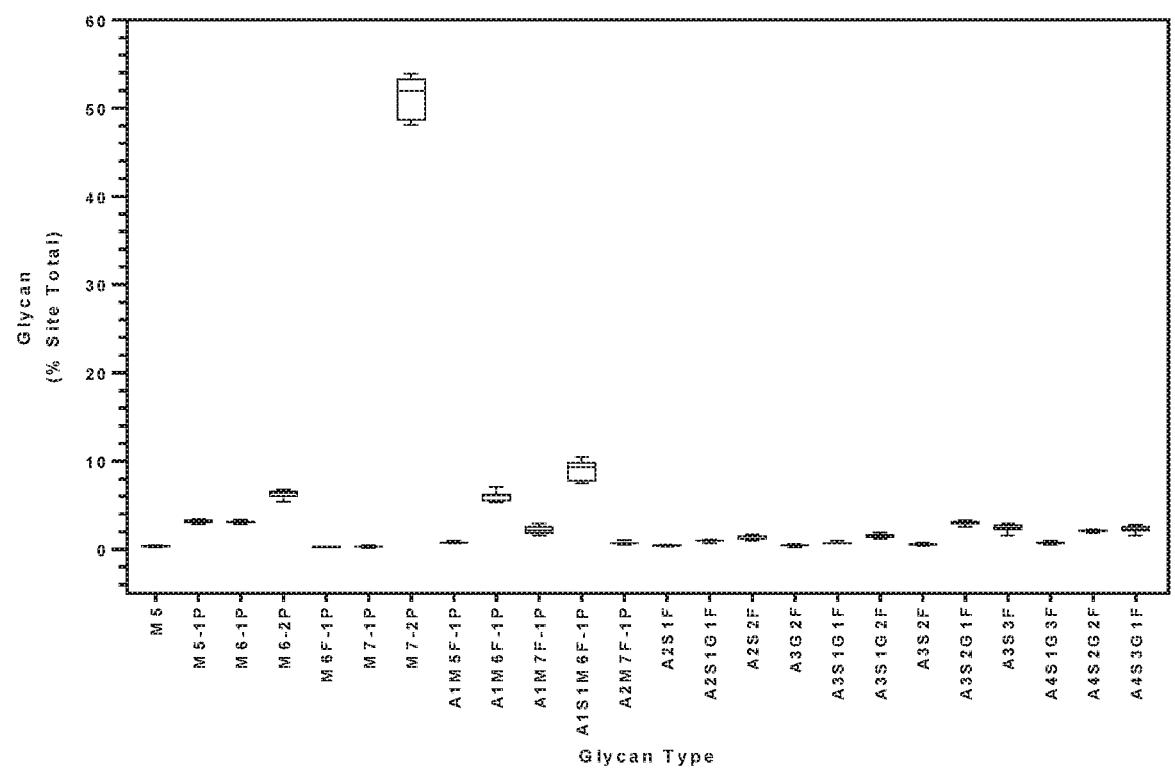
Figure 32C:
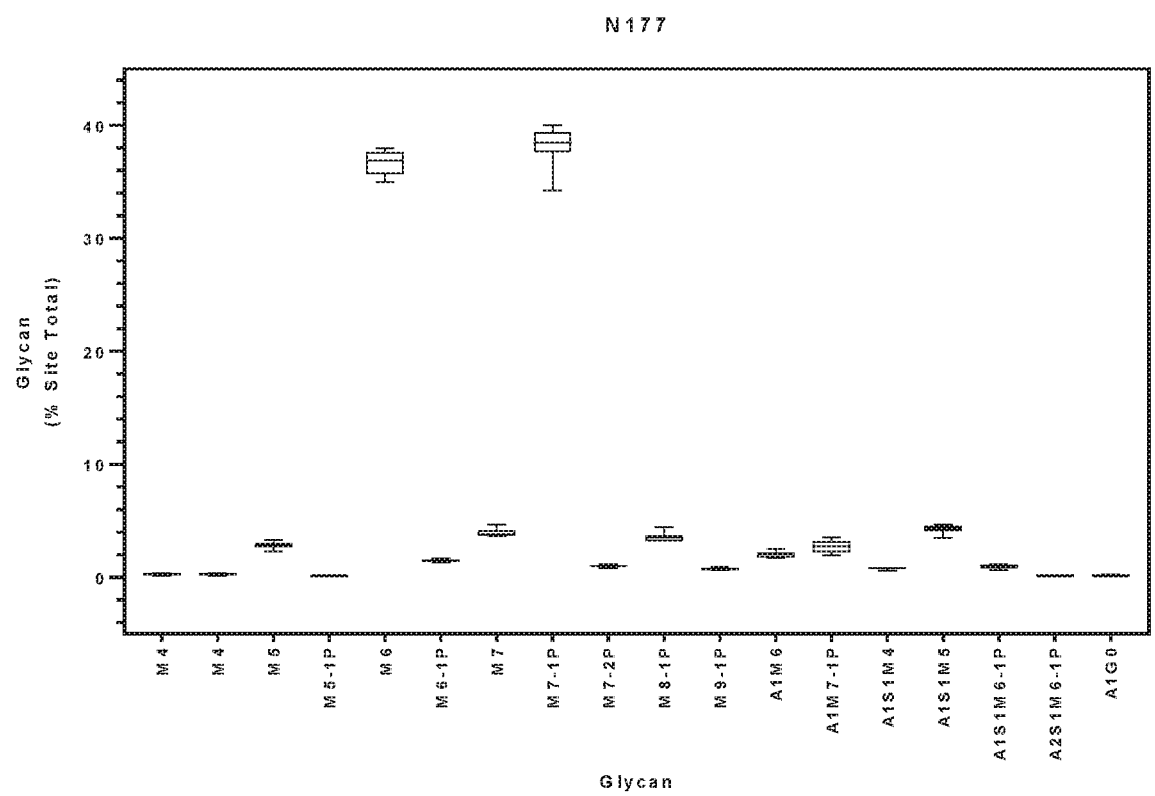
Figure 32D:
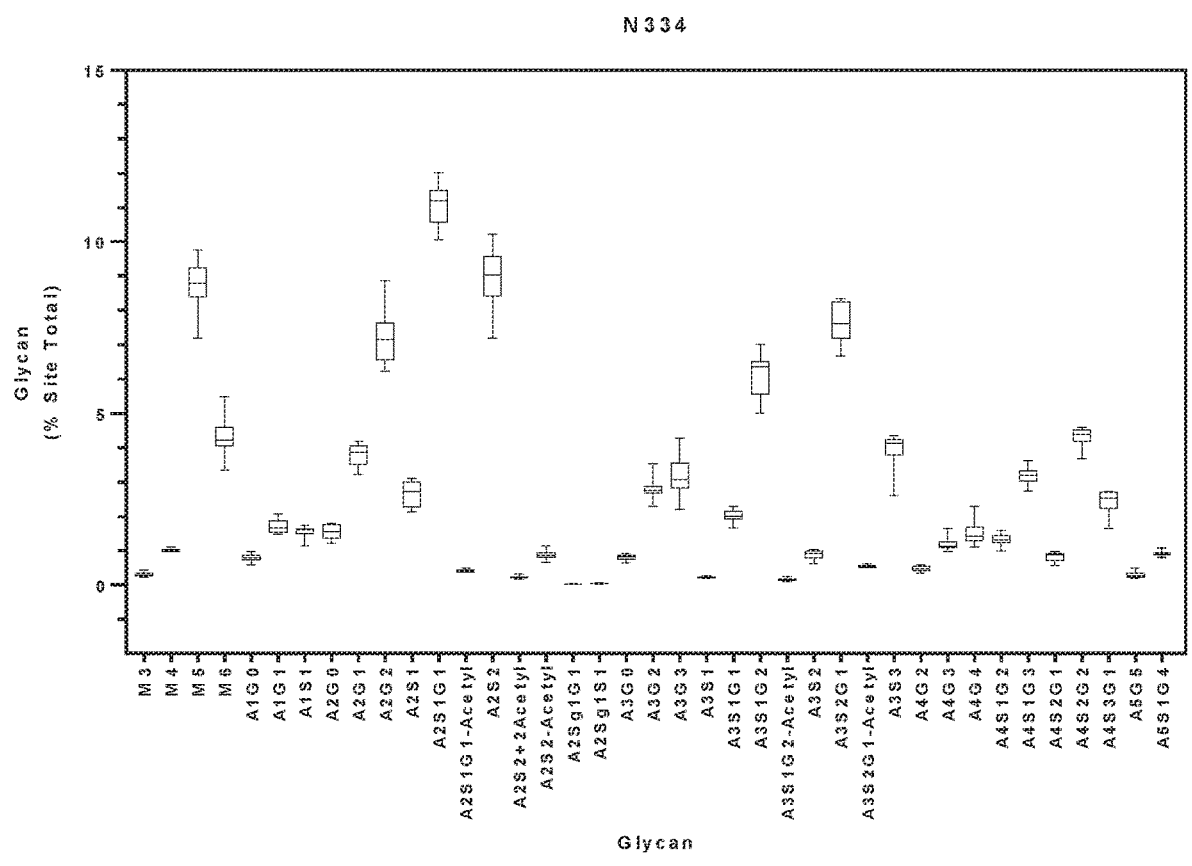
Figure 32E:
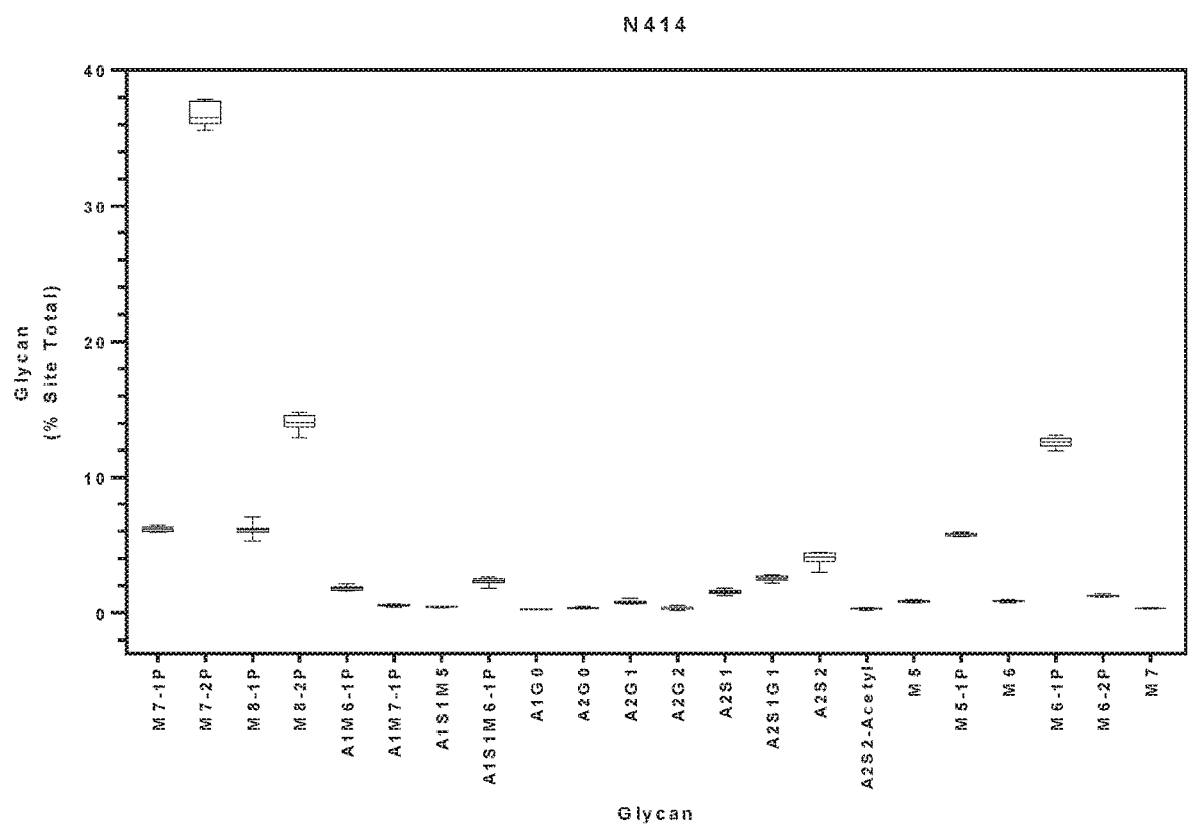
Figure 32F:
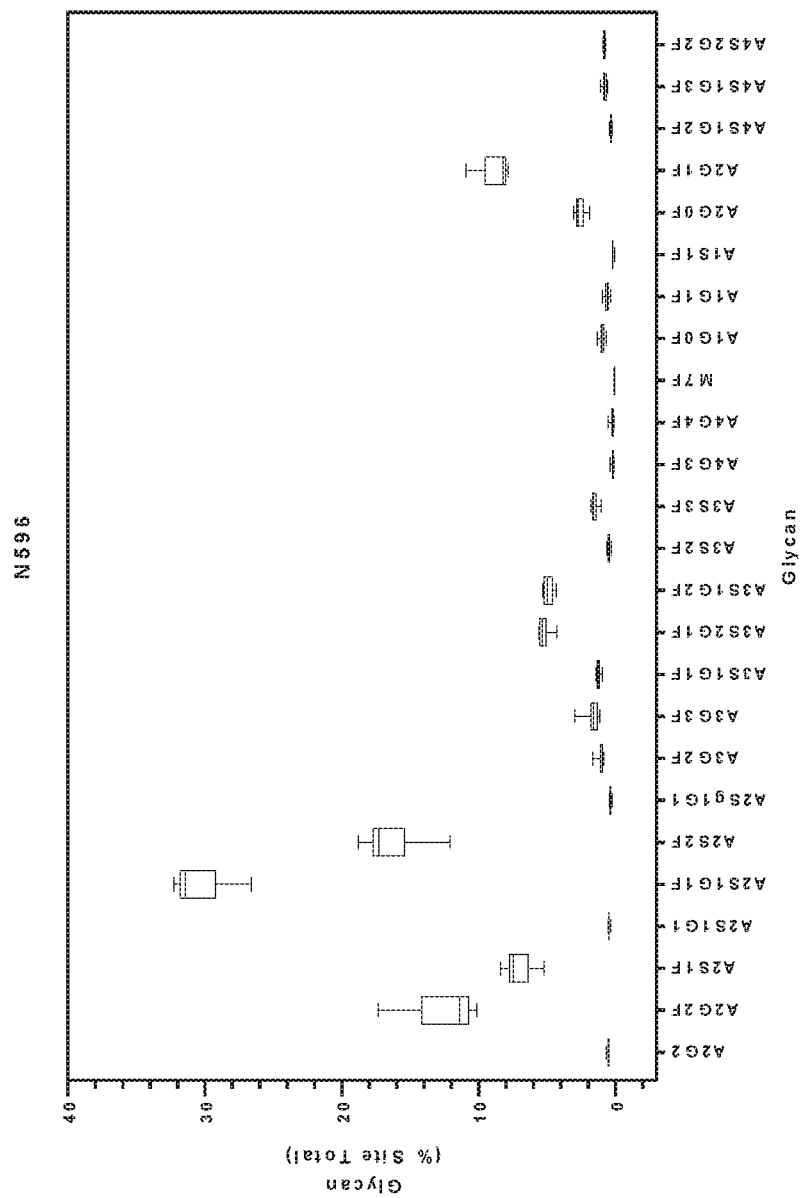
Figure 32G:
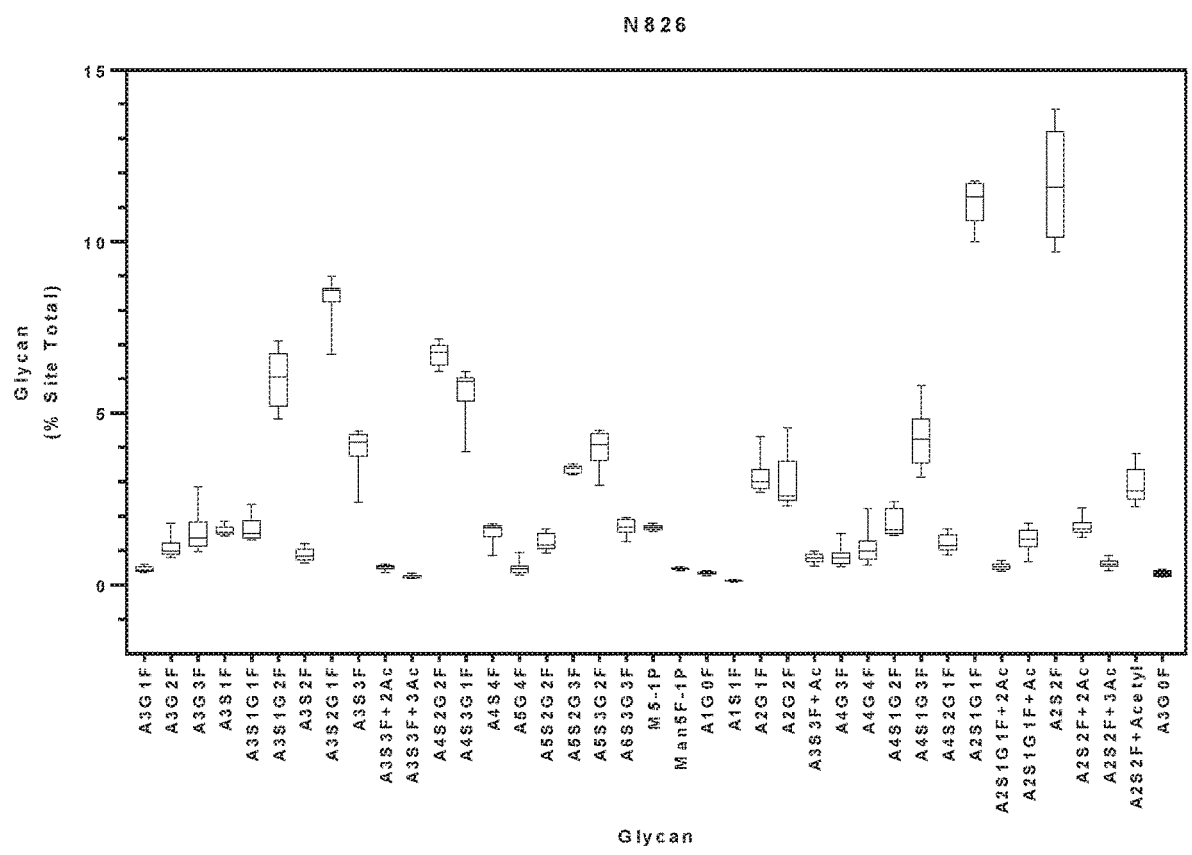
Figure 32H:
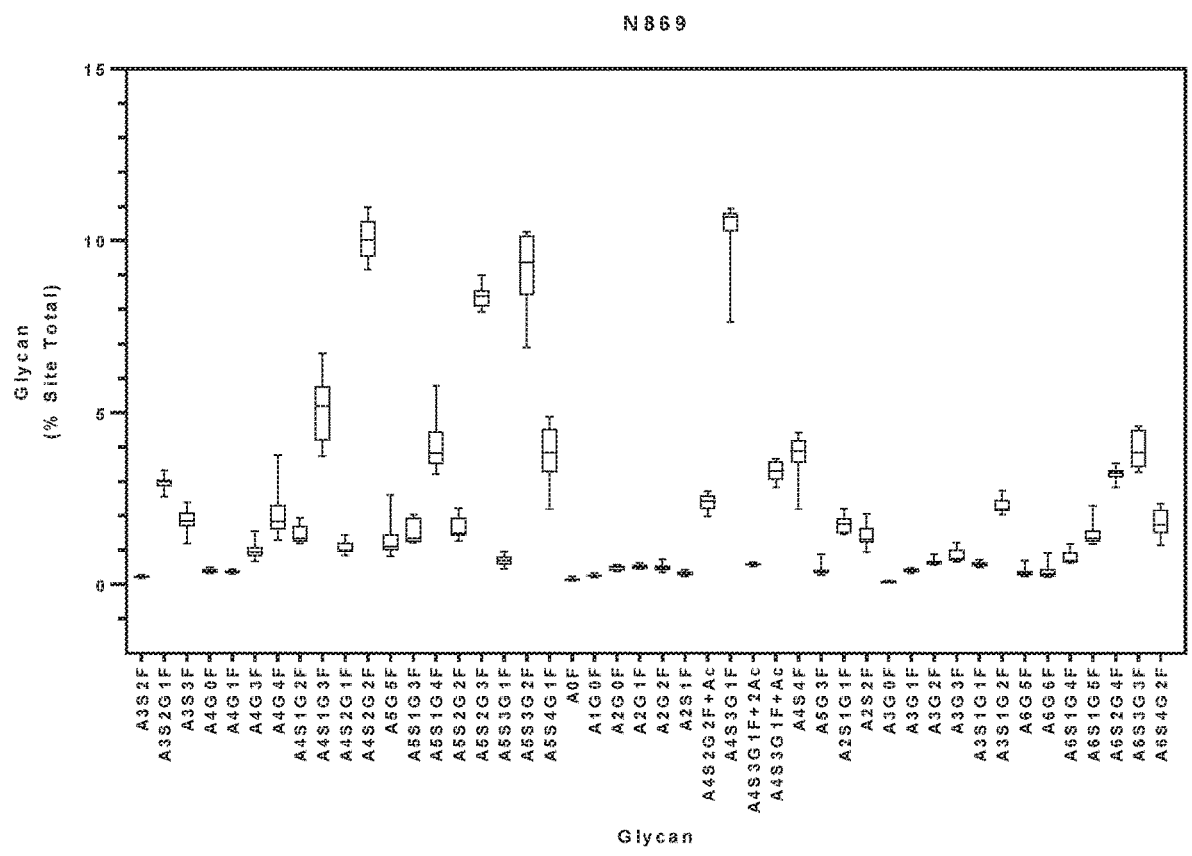

FIGS. 32B-32H show the site-specific N-glycosylation analyses of all seven potential N-glycosylation sites for ATB200, with site numbers provided according to SEQ ID NO: 5. Bars represent the maximum and minimum percentage of N-glycan species identified as a particular N-glycan group for the ten lots of ATB200 analyzed. FIG. 32B shows the N-glycosylation profile of the first potential N-glycosylation site for ATB200. FIG. 32C shows the N-glycosylation profile of the second potential N-glycosylation site for ATB200. FIG. 32D shows the N-glycosylation profile of the third potential N-glycosylation site for ATB200. FIG. 32E shows the N-glycosylation profile of the fourth potential N-glycosylation site for ATB200. FIG. 32F shows the N-glycosylation profile of the fifth potential N-glycosylation site for ATB200. FIG. 32G shows the N-glycosylation profile of the sixth potential N-glycosylation site for ATB200. FIG. 32H shows the N-glycosylation profile of the seventh potential N-glycosylation site for ATB200.

Figure 33A:
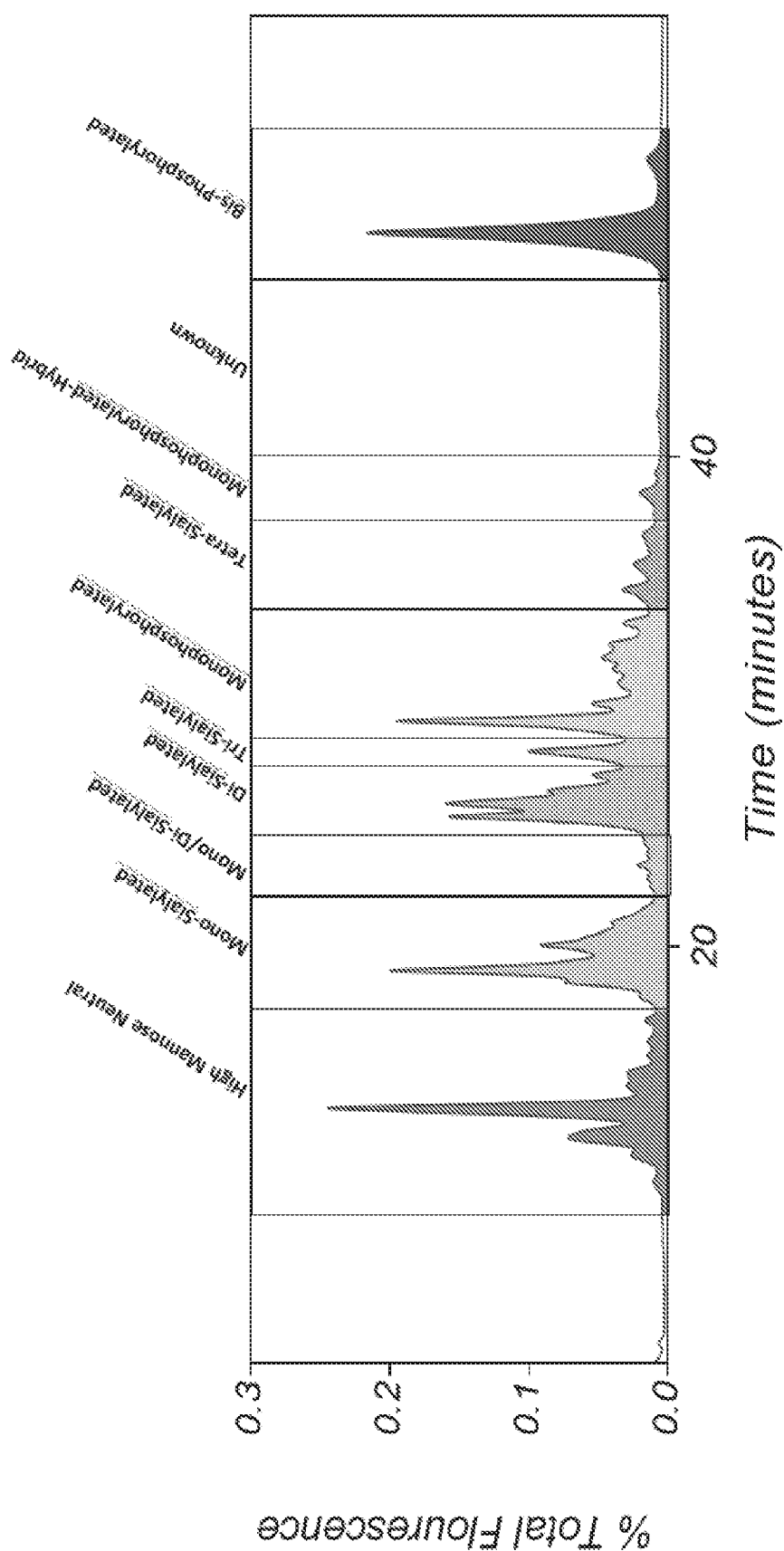

FIGS. 33A-33B further characterize and summarize the N-glycosylation profile of ATB200, as also shown in FIGS. 32A-32H. FIG. 33A shows 2-Anthranilic acid (2-AA) glycan mapping and LC/MS-MS analysis of ATB200 and summarizes the N-glycan species identified in ATB200 as a percentage of total fluorescence. Data from 2-AA glycan mapping and LC-MS/MS analysis are also depicted in Table 5. FIG. 33B summarizes the average site occupancy and average N-glycan profile, including total phosphorylation, mono-phosphorylation, bis-phosphorylation, and sialylation, for all seven potential N-glycosylation sites for ATB200. ND=not detected.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

I. Definition

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them. The articles "a" and "an" refer to one or to more than one (i.e., to at least one) of the grammatical object of the article. The term "or" means, and is used interchangeably with, the term "and/or," unless context clearly indicates otherwise. In this application, the use of the singular includes the plural unless specifically stated otherwise. Furthermore, the use of the term "including," as well as other forms, such as "includes" and "included," are not limiting. Any range described herein will be understood to include the endpoints and all values between the endpoints. In the present specification, except where the context requires otherwise due to express language or necessary implication, the word "comprises", or variations such as "comprising" is used in an inclusive sense, i.e., to specify the presence of the stated features but not to preclude the presence or addition of further features in various embodiments of the invention.

The term "GAA" refers to human acid α-glucosidase (GAA) enzyme that catalyzes the hydrolysis of α-1,4- and α-1,6-glycosidic linkages of lysosomal glycogen as well as to insertional, relational, or substitution variants of the GAA amino acid sequence and fragments of a longer GAA sequence that exert enzymatic activity. Human acid α-glucosidase is encoded by the GAA gene (National Centre for Biotechnology Information (NCBI) Gene ID 2548), which has been mapped to the long arm of chromosome 17 (location 17q25.2-q25.3). An exemplary DNA sequence encoding GAA is NP 000143.2, which is incorporated by reference. More than 500 mutations have currently been identified in the human GAA gene, many of which are associated with Pompe disease. Mutations resulting in misfolding or misprocessing of the acid α-glucosidase enzyme include T1064C (Leu355Pro) and C2104T (Arg702Cys). In addition, GAA mutations which affect maturation and processing of the enzyme include Leu405Pro and Met519Thr. The conserved hexapeptide WIDMNE at amino acid residues 516-521 is required for activity of the acid α-glucosidase protein. As used herein, the abbreviation "GAA" is intended to refer to human acid α-glucosidase enzyme, while the italicized abbreviation "GAA" is intended to refer to the human gene coding for the human acid α-glucosidase enzyme. The italicized abbreviation "Gad" is intended to refer to non-human genes coding for non-human acid α-glucosidase enzymes, including but not limited to rat or mouse genes, and the abbreviation "Gaa" is intended to refer to non-human acid α-glucosidase enzymes.

The term "rhGAA" is intended to refer to the recombinant human acid α-glucosidase enzyme and is used to distinguish endogenous GAA from synthetic or recombinant-produced GAA (e.g., GAA produced from CHO cells transformed with DNA encoding GAA). The term "rhGAA" encompasses a population of individual rhGAA molecules. Characteristics of the population of rhGAA molecules are provided herein. The term "conventional rhGAA product" is intended to refer to products containing alglucosidase alfa, such as Lumizyme® or Myozyme®.

The term "genetically modified" or "recombinant" refers to cells, such as CHO cells, that express a particular gene product, such as rhGAA, following introduction of a nucleic acid comprising a coding sequence which encodes the gene product, along wife regulatory elements feat control expression of fee coding sequence. Introduction of fee nucleic acid may be accomplished by any method known in fee art including gene targeting and homologous recombination. As used herein, fee term also includes cells feat have been engineered to express or overexpress an endogenous gene or gene product not normally expressed by such cell, e.g., by gene activation technology.

The term "purified" as used herein refers to material feat has been isolated under conditions feat reduce or eliminate fee presence of unrelated materials, i.e., contaminants, including native materials from which fee material is obtained. For example, a purified protein is preferably substantially free of other proteins or nucleic acids with which it is associated in a cell: a purified nucleic acid molecule is preferably substantially free of proteins or other unrelated nucleic acid molecules wife which it can be found within a cell. As used herein, fee term "substantially free" is used operationally, in fee context of analytical testing of fee material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, enzymatic assay and other methods known in fee art. In a specific embodiment, purified means feat fee level of contaminants is below a level acceptable to regulatory authorities for safe administration to a human or non-human animal. Recombinant proteins, such as rhGAA may be isolated or purified from CHO cells using methods known in fee art including by chromatographic size separation, affinity chromatography, or anionic exchange chromatography. In some embodiments, rhGAA is purified by a method comprising anionic exchange chromatography followed by immobilized metal affinity chromatography, optionally followed by purification using a third chromatography column.

As used herein, the term "alglucosidase alfa" is intended to refer to a recombinant human acid α-glucosidase identified as [199-arginine,223-histidine]prepro-α-glucosidase (human); Chemical Abstracts Registry Number 420794-05-0. Alglucosidase at fa is approved for marketing in the United States by Genzyme, as the products Lumizyme® and Myozyme®.

As used herein, the term "ATB200" is intended to refer to a recombinant human acid α-glucosidase described in International Application PCT/US2015/053252, the disclosure of which is herein incorporated by reference.

As used herein, the term "glycan" is intended to refer to a polysaccharide chain covalently bound to an amino acid residue on a protein or polypeptide. As used herein, the term "N-glycan" or "N-linked glycan" is intended to refer to a polysaccharide chain attached to an amino acid residue on a protein or polypeptide through covalent binding to a nitrogen atom of the amino acid residue. For example, an N-glycan can be covalently bound to the side chain nitrogen atom of an asparagine residue. Glycans may contain one or several monosaccharide units, and the monosaccharide units may be covalently linked to form a straight chain or a branched chain. In at least one embodiment, N-glycan units attached to a rhGAA may comprise one or more monosaccharide units each independently selected from N-acetylglucosamine, mannose, galactose, fucose, mannose-6-phosphate, or sialic acid. The N-glycan units on the protein may be determined by any appropriate analytical technique, such as mass spectrometry. In some embodiments, the N-glycan units attached to a rhGAA are determined by liquid chromatography-tandem mass spectrometry (LC-MS/MS) utilizing an instrument such as the Thermo Scientific™ Orbitrap Velos Pro™ Mass Spectrometer, Thermo Scientific™ Orbitrap Fusion™ Lumos Tribid™ Mass Spectrometer or Waters Xevo® G2-XS QTof Mass Spectrometer.

As used herein, the term "high-mannose N-glycan" is intended to refer to an N-glycan having one to six or more mannose units. In some embodiment, a high mannose N-glycan unit may contain a bis(N-acetylglucosamine) chain bonded to an asparagine residue and further bonded to a branched polymannose chain. As used herein interchangeably, the term "M6P" or "mannose-6-phosphate" is intended to refer to a mannose unit phosphorylated at the 6 position, i.e., having a phosphate group bonded to the hydroxyl group at the 6 position. In some embodiments, one or more mannose units of one or more N-glycan units are phosphorylated at the 6 position to form mannose-6-phosphate units. In some embodiment, the term "M6P" or "mannose-6-phosphate" refers to both a mannose phosphodiester having N-acetylglucosamine (GlcNAc) as a "cap" on the phosphate group, as well as a mannose unit having an exposed phosphate group lacking the GlcNAc cap. In at least one embodiment, the N-glycans of a protein may have multiple M6P groups, with at least one M6P group having a GlcNAc cap and at least one other M6P group lacking a GlcNAc cap.

Figure 1A:
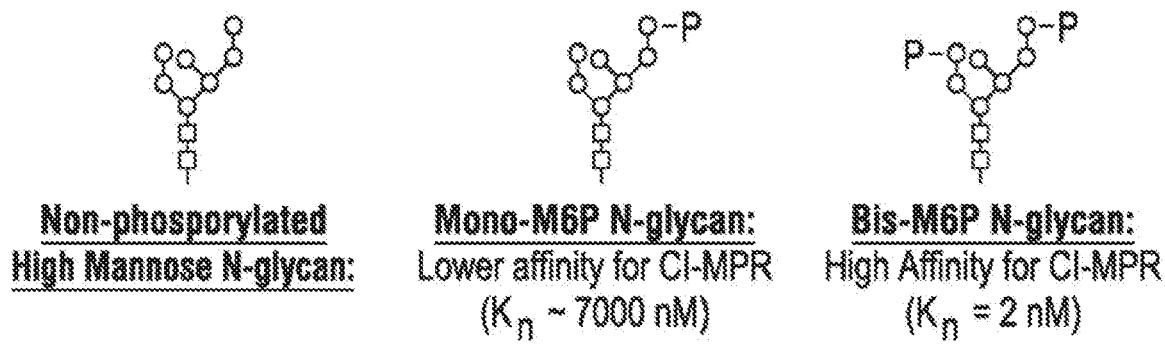
FIG. 1A shows non-phosphorylated high mannose N-glycan, a mono-M6P N-glycan, and a bis-M6PN-glycan.
Figure 1B:
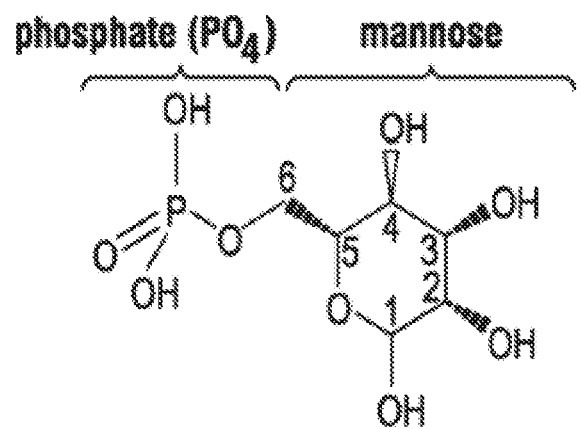
FIG. 1B shows the chemical structure of the M6P group. Each square represents N-acetylglucosamine (GlcNAc), each circle represents mannose, and each P represents phosphate.

As used herein, the term "complex N-glycan" is intended to refer to an N-glycan comprising types of saccharides other than GlcNac and mannose, for example, one or more galactose and/or sialic acid units. In at least one embodiment, a complex N-glycan can be a high-mannose N-glycan in which one or mannose units are further bonded to one or more monosaccharide units each independently selected from N-acetylglucosamine, galactose, and sialic acid. As used herein, a "hybrid N-glycan" is intended to refer to an N-glycan comprising at least one high-mannose branch and at least one complex branch. Representative structures for non-phosphorylated, mono-M6P. and bis-M6P N-glycans are shown in FIG. 1A. The mannose-6-phosphate group is shown in FIG. 1B.

As used herein, "normalization" of lysosomes in a muscle refers to the process of restoring the affected muscle to a lysosomal morphology of a wild-type muscle by reducing the size and number of its accumulated glycogen so that the affected muscle would substantially resemble the normal lysosomal morphology, ultimately leading to reverse disease progression.

As used herein, "reversal of disease progression" means, among other things, adequately (i) reducing or eliminating glycogen accumulation, (ii) reducing or eliminating lysosomal swelling and/or dysfunction, and (iii) reducing or eliminating the buildup of autophagic debris. Reversal of disease progression may manifest in an ambulatory ERT-experienced Pompe disease patient as two or more of the following "clinical improvements": (a) an average increase in six-minute walk test distance of at least 20 meters, (b) an average improvement in maximum expiratory pressure of at least 16 cmH$_2$O, and (c) an average decrease in fatigue severity scale score of at least 7. Reversal of disease progression may manifest in a nonambulatory ERT-experienced Pompe disease patient as two or more of the following "clinical improvements": (a) an average improvement in shoulder adduction of at least 8 pounds of force, (b) an average improvement in elbow extension of at least 5 pounds of force, and (c) an average decrease in fatigue severity scale score of at least 3.5. Reversal of disease progression may manifest in an ERT-naive Pompe disease patient as two or more of the following "clinical improvements": (a) an average increase in six-minute walk test distance of at least 40 meters, (b) an average improvement in upright (sitting) forced vital capacity of at least 4%, (c) an average improvement in maximum inspiratory pressure of at least 11 cmH$_2$O, and (d) an average decrease in fatigue severity scale score of at least 5.

An advantage of the method of treatment disclosed herein compared to administration of alglucosidase alfa is that Pompe patients treated with the former exhibit prolonged clinical improvement. For example, improvements may be observed at two to three years from the administration of first treatment or beyond, including, for example, four, five, or six years from the administration of first treatment. In contrast, after two years of enzyme replacement therapy with the standard of care (e.g., alglucosidase alfa), Pompe disease patients either (i) maintain their gains from baseline prior to treatment, but exhibit no discernable improvement beyond the two or three-year mark or (ii) experience a gradual decline and lose any gains achieved through two or three years after treatment with the standard of care. Kuperus et al. 2017. Long-term benefit of enzyme replacement therapy in Pompe disease: A 5-year prospective study. Neurology. 89:2365-2373. In contrast, the rhGAA described herein clears lysosomal glycogen more efficiently than docs the standard of care and has been shown to elicit improvements in patients (e.g., "ERT-switch ambulatory," Cohort 1 of Study ATB200-02) not expected to improve after taking an enzyme replacement therapy for at least two years. Clinical data to date using the rhGAA or pharmaceutical composition described herein is expected to deliver continued improvement in patient outcomes even after two-years post-treatment. Thus, in some embodiments, a patient treated with the rhGAA or pharmaceutical composition described herein continues to exhibit progress in one or more clinical improvements for more than two years after treatment (e.g., experiences further gains beyond the gain achieved by or at the two-year mark).

As used herein, "reversal of lysosomal pathology" means partial or complete clearance of glycogen that had accumulated in the cell due to lack of optimal GAA activity.

As used herein, forced vital capacity, or "FVC," is the amount of air that can be forcibly exhaled from the lungs of a subject after the subject takes the deepest breath possible.

As used herein, a "six-minute walk test" (6MWT) is a test for measuring the distance an individual is able to walk over a total of six minutes on a hard, flat surface. The test is conducted by having the individual to walk as far as possible in six minutes.

As used herein, a "ten-meter walk test" (10MWT) is a test for measuring the time it takes an individual in walking shoes to walk ten meters on a flat surface.

As used herein, the compound miglustat, also known as N-butyl-1-deoxynojirimycin or NB-DNJ or (2R,3R,4R,5S)-1-butyl-2-(hydroxymethyl)piperidine-3,4,5-triol, is a compound having the following chemical formula:

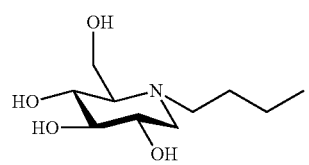

One formulation of miglustat is marketed commercially under the trade name Zavcsca® as monotherapy for type 1 Gaucher disease. In some embodiments, miglustat is referred to as AT2221.

As discussed below, pharmaceutically acceptable salts of miglustat may also be used in the present invention. When a salt of miglustat is used, the dosage of the salt will be adjusted so that the dose of miglustat received by the patient is equivalent to the amount which would have been received had the miglustat free base been used.

As used herein, the compound duvoglustat, also known as 1-dcoxynojirimycin or DNJ or (2R,3R,4R,5S)-2-(hydroxymethyl)piperidine-3,4,5-triol, is a compound having the following chemical formula:

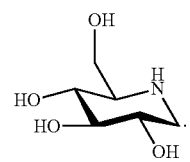

As used herein, the term "pharmacological chaperone" or sometimes simply the term "chaperone" is intended to refer to a molecule that specifically binds to acid α-glucosidase and has one or more of the following effects:
  enhances the formation of a stable molecular conformation of the protein;
  enhances proper trafficking of the protein from the endoplasmic reticulum to another cellular location, preferably a native cellular location, so as to prevent endoplasmic reticulum-associated degradation of the protein;
  prevents aggregation of conformationally unstable or misfolded proteins;
  restores and/or enhances at least partial wild-type function, stability, and/or activity of the protein; and/or
  improves the phenotype or function of the cell harboring acid α-glucosidase.

Thus, a pharmacological chaperone for acid α-glucosidase is a molecule that binds to acid α-glucosidase, resulting in proper folding, trafficking, non-aggregation, and activity of acid α-glucosidase. As used herein, this term includes but is not limited to active site-specific chaperones (ASSCs)

which bind in the active site of the enzyme, inhibitors or antagonists, and agonists. In at least one embodiment, the pharmacological chaperone can be an inhibitor or antagonist of acid α-glucosidase. As used herein, the term "antagonist" is intended to refer to any molecule that binds to acid α-glucosidase and either partially or completely blocks, inhibits, reduces, or neutralizes an activity of acid α-glucosidase. In at least one embodiment, the pharmacological chaperone is miglustat. Another non-limiting example of a pharmacological chaperone for acid α-glucosidase is duvoglustat.

As used herein, the term "active site" is intended to refer to a region of a protein feat is associated with and necessary for a specific biological activity of fee protein. In at least one embodiment, the active site can be a site feat binds a substrate or other binding partner and contributes fee amino acid residues feat directly participate in the making and breaking of chemical bonds. Active sites in this invention can encompass catalytic sites of enzymes, antigen binding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "AUC" or "area under the curve" is intended to refer to a mathematical calculation to evaluate the body's total exposure over time to a given drug. In a graph plotting how concentration in the blood of a drug administered to a subject changes with time after dosing, the drug concentration variable lies on the y-axis and time lies on the x-axis. The area between the drug concentration curve and the x-axis for a designated time interval is the AUC. AUCs are used as a guide for dosing schedules and to compare the bioavailability of different drugs' availability in the body.

As used herein, the term "Cmax" is intended to refer to the maximum plasma concentration of a drug achieved after administration to a subject.

As used herein, the term "volume of distribution" or "V" is intended to refer to the theoretical volume that would be necessary to contain the total amount of an administered drug at the same concentration that it is observed in the blood plasma, and represents the degree to which a drug is distributed in body tissue rather than the plasma. Higher values of V indicate a greater degree of tissue distribution. "Central volume of distribution" or "Vc" is intended to refer to the volume of distribution within the blood and tissues highly perfused by blood. "Peripheral volume of distribution" or "V2" is intended to refer to the volume of distribution within the peripheral tissue.

As used interchangeably herein, the term "clearance," "systemic clearance," or "CL" is intended to refer to the volume of plasma that is completely cleared of an administered drug per unit time. "Peripheral clearance" is intended to refer to the volume of peripheral tissue that is cleared of an administered drug per unit time.

As used herein, the term "pharmaceutically acceptable" is intended to refer to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. As used herein, the term "carrier" is intended to refer to a diluent, adjuvant, excipient, or vehicle with which a compound is administered. Suitable pharmaceutical carriers are known in the art and, in at least one embodiment, are described in "Remington's Pharmaceutical Sciences" by E. W. Martin, 18th Edition, or other editions.

The term "pharmaceutically acceptable salt" as used herein is intended to mean a salt which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Beige et al., J. Pharm. Sci., 1977, 66, pp. 1-19, herein incorporated by reference. The term "pharmaceutically-acceptable acid addition salt" as used herein is intended to mean those salts which retain the biological effectiveness and properties of the fee bases and which are not biologically or otherwise undesirable, formed with inorganic acids. The term "pharmaceutically-acceptable base addition salt" as used herein is intended to mean those salts which retain the biological effectiveness and properties of the free acids and which are not biologically or otherwise undesirable, formed with inorganic bases.

As used herein, the term "buffer" refers to a solution containing a weak acid and its conjugate base that helps to prevent changes in pH.

As used herein, the terms "therapeutically effective dose" and "effective amount" are intended to refer to an amount of acid α-glucosidase and/or of miglustat and/or of a combination thereof, which is sufficient to result in a therapeutic response in a subject. A therapeutic response may be any response that a user (for example, a clinician) will recognize as an effective response to the therapy, including any surrogate clinical markers or symptoms described herein and known in the art. Thus, in at least one embodiment, a therapeutic response can be an amelioration or inhibition of one or more symptoms or markers of Pompe disease such as those known in the art. Symptoms or markers of Pompe disease include but are not limited to decreased acid α-glucosidase tissue activity: cardiomyopathy; cardiomegaly; progressive muscle weakness, especially in the trunk or lower limbs; profound hypotonia: macroglossia (and in some cases, protrusion of the tongue): difficulty swallowing, sucking, and/or feeding: respiratory insufficiency: hepatomegaly (moderate); laxity of facial muscles; areflexia; exercise intolerance: exertional dyspnea: orthopnea: sleep apnea; morning headaches; somnolence; lordosis and/or scoliosis; decreased deep tendon reflexes; lower back pain; and failure to meet developmental motor milestones. It should be noted that a concentration of miglustat that has an inhibitory effect on acid α-glucosidase may constitute an "effective amount" for purposes of this invention because of dilution (and consequent shift in binding due to the change in equilibrium and pH), bioavailability, and metabolism of miglustat upon administration in vivo.

The therapeutic response may also include molecular responses such as glycogen accumulation, lysosomal proliferation, and formation of autophagic zones. The therapeutic responses may be evaluated by comparing physiological and molecular responses of muscle biopsies before and after treatment with a rhGAA described herein. For instance, the amount of glycogen present in the biopsy samples can be used as a marker for determining the therapeutic response. Another example includes biomarkers such as LAMP-1, LC3, and Dysferlin, which can be used as an indicator of lysosomal storage dysfunction. For instance, muscle biopsies collected prior to and after treatment with a rhGAA described herein may be stained with an antibody that recognizes one of the biomarkers.

As used herein, the term "enzyme replacement therapy" or "ERT" is intended to refer to the introduction of a non-native, purified enzyme into an individual having a deficiency in such enzyme. The administered protein can be obtained from natural sources or by recombinant expression. The term also refers to the introduction of a purified enzyme in an individual otherwise requiring or benefiting from administration of a purified enzyme. In at least one embodiment, such an individual suffers from enzyme insufficiency. The introduced enzyme may be a purified, recombinant enzyme produced in vitro, or a protein purified from isolated tissue or fluid, such as, for example, placenta or animal milk, or from plants.

As used herein, the term "combination therapy" is intended to refer to any therapy wherein two or more individual therapies are administered concurrently or sequentially. In some embodiment, the results of the combination therapy are enhanced as compared to the effect of each therapy when it is performed individually. Enhancement may include any improvement of the effect of the various therapies that may result in an advantageous result as compared to the results achieved by the therapies when performed alone. Enhanced effect or results can include a synergistic enhancement, wherein the enhanced effect is more than the additive effects of each therapy when performed by itself; an additive enhancement, wherein the enhanced effect is substantially equal to the additive effect of each therapy when performed by itself; or less than additive effect, wherein the enhanced effect is lower than the additive effect of each therapy when performed by itself, but still better than the effect of each therapy when performed by itself. Enhanced effect may be measured by any means known in the art by which treatment efficacy or outcome can be measured.

The term "concurrently" as used herein is intended to mean at the same time as or within a reasonably short period of time before or after, as will be understood by those skilled in the art. For example, if two treatments are administered concurrently with each other, one treatment can be administered before or after the other treatment, to allow for time needed to prepare for the later of the two treatments. Therefore "concurrent administration" of two treatments includes but is not limited to one treatment following the other by about 30 minutes or less, about 30 minutes, 20 minutes or less, about 20 minutes, about 15 minutes, about 10 minutes, about 9 minutes, about 8 minutes, about 7 minutes, about 6 minutes about 5 minutes, about 4 minutes, about 3 minutes, about 2 minutes, about 1 minute, or less than 1 minute.

"Pompe Disease" refers to an autosomal recessive LSD characterized by deficient acid alpha glucosidase (GAA) activity which impairs lysosomal glycogen metabolism. The enzyme deficiency leads to lysosomal glycogen accumulation and results in progressive skeletal muscle weakness, reduced cardiac function, respiratory insufficiency, and/or CNS impairment at late stages of disease. Genetic mutations in the GAA gene result in either lower expression or produce mutant forms of the enzyme with altered stability, and/or biological activity ultimately leading to disease, (see generally Hirschhorn R, 1995, Glycogen Storage Disease Type II: Acid a-Glucosidase (Acid Maltase) Deficiency, The Metabolic and Molecular Bases of Inherited Disease, Scriver et al., eds., McGraw-Hill, New York, 7th ed., pages 2443-2464). The three recognized clinical forms of Pompe Disease (infantile, juvenile and adult) are correlated with the level of residual α-glucosidase activity (Reuser A J et al., 1995, Glycogenosis Type 11 (Acid Maltase Deficiency), Muscle & Nerve Supplement 3, S61-S69). Infantile Pompe disease (type I or A) is most common and most severe, characterized by failure to thrive, generalized hypotonic, cardiac hypertrophy, and cardiorespiratory failure within the second year of life. Juvenile Pompe disease (type II or B) is intermediate in severity and is characterized by a predominance of muscular symptoms without cardiomegaly. Juvenile Pompe individuals usually the before reaching 20 years of age due to respiratory failure. Adult Pompe disease (type III or C) often presents as a slowly progressive myopathy in the teenage years or as late as the sixth decade (Felicia K J et al., 1995, Clinical Variability in Adult-Onset Acid Maltase Deficiency: Report of Affected Sibs and Review of the Literature, Medicine 74, 131-135). In Pompe, it has been shown that α-glucosidase is extensively modified post-translationally by glycosylation, phosphorylation, and proteolytic processing. Conversion of the 110 kilodalton (kDa) precursor to 76 and 70 KDa mature forms by proteolysis in the lysosome is required for optimum glycogen catalysis. As used herein, the term "Pompe Disease" refers to all types of Pompe Disease. The formulations and dosing regimens disclosed in this application may be used to treat, for example, Type I, Type II or Type III Pompe Disease.

A "subject" or "patient" is preferably a human, though other mammals and non-human animals having disorders involving accumulation of glycogen may also be treated. A subject may be a fetus, a neonate, child, juvenile, or an adult with Pompe disease or other glycogen storage or accumulation disorder. One example of an individual being treated is an individual (fetus, neonate, child, juvenile, adolescent, or adult human) having GSD-II (e.g., infantile GSD-II, juvenile GSD-II, or adult-onset GSD-II). The individual can have residual GAA activity, or no measurable activity. For example, the individual having GSD-11 can have GAA activity that is less than about 1% of normal GAA activity (infantile GSD-II), GAA activity that is about 1-10% of normal GAA activity (juvenile GSD-II), or GAA activity that is about 10-40% of normal GAA activity (adult GSD-II). In some embodiments, the subject or patient is an "ERT-experienced" or "ERT-switch" patient, referring to a Pompe disease patient who has previously received enzyme replacement therapy. In some embodiments, the subject or patient is an "ERT-naïve" patient, referring to a Pompe disease patient who has not previously received enzyme replacement therapy. In certain embodiments, the subject or patient is ambulatory (e.g., an ambulatory ERT-switch patient or an ambulatory ERT-naïve patient). In certain embodiments, the subject or patient is nonambulalory (e.g., a nonambulatory ERT-switch patient). Ambulatory or non-ambulatory status may be determined by a six-minute walk test (6MWT). In some embodiments, an ambulatory patient is a Pompe disease patient who is able to walk at least 200 meters in the 6MWT. In some embodiments, a nonambulatory patient is a Pompe disease patient who is unable to walk unassisted or who is wheelchair bound.

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to improvement of cardiac status (e.g. increase of end-diastolic and/or end-systolic volumes, or reduction, amelioration or prevention of the progressive cardiomyopathy that is typically found in GSD-II) or of pulmonary function (e.g., increase in crying vital capacity over baseline capacity, and/or normalization of oxygen desaturation during crying): improvement in neurodevelopment and/or motor skills (e.g., increase in AIMS score); reduction of glycogen levels in tissue of the individual affected by the disease; or any combination of these effects. In one preferred embodiment, treatment includes improvement of cardiac status, particularly in reduction or prevention of GSD-II-associated cardiomyopathy.

The terms, "improve," "increase," and "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of GSD-II (either infantile, juvenile, or adult-onset) as the individual being treated, who is about the same age as the individual being treated (to ensure that the stages of the disease in the treated individual and the control individual(s) are comparable).

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Numerical quantities given herein are approximate unless stated otherwise, meaning that the term "about" or "approximately" can be inferred when not expressly stated.

II. Recombinant Human Acid α-Glucosidase (rhGAA)

In some embodiments, the recombinant human acid α-glucosidase (rhGAA) is an enzymic having an amino acid sequence as set forth in SEQ ID NO; 1, SEQ ID NO: 3, SEQ ID NO: 4, or SEQ ID NO: 5. In some embodiments, the rhGAA is encoded by a nucleotide sequence as set forth in SEQ ID NO: 2

Table 1

Nucleotide Sequences and Protein Sequences

| SEQ ID NO: | Sequences |
|---|---|
| 1 | MGVRHPPCSHRLLAVCALVS<br>LATAALLGHILLHDFLLVPR<br>ELSGSSPVLEETHPAHQQGA<br>SRPGPRDAQAHPGRPRAVPT<br>QCDVPPNSRFDCAPDKAITQ<br>EQCEARGCCYIPAKQGLQGA<br>QMGQPWCFFPPSYPSYKLEN<br>LSSSEMGYTATLTRTTPTFF<br>PKDILTLRLDVMMETENRLH<br>FTIKDPANRRYEVPLETPRV<br>HSRAPSPLYSVEFSEEPFGV<br>IVHRQLDGRVLLNTTVAPLF<br>FADQFLQLSTSLPSQYITGL<br>AEHLSPLMLSTSWTRITLWN<br>RDLAPTPGANLYGSHPFYLA |

Table 1 -continued

Nucleotide Sequences and Protein Sequences

| SEQ ID NO: | Sequences |
|---|---|
| | LEDGGSAHGVFLLNSNAMDV<br>VLQPSPALSWRSTGGILDVY<br>IFLGPEPKSVVQQYLDVVGY<br>PFMPPYWGLGFHLCRWGYSS<br>TAITRQVVENMTRAHFPLDV<br>QWNDLDYMDSRRDFTFNKDG<br>FRDFPAMVQELHQGGRRYMM<br>IVDPAISSSGPAGSYRPYDE<br>GLRRGVFITNETGQPLIGKV<br>WPGSTAFPDFTNPTALAWWE<br>DMVAEFHDQVPFDGMWIDMN<br>EPSNFIRGSEDGCPNNELEN<br>PPYVPGVVGGTLQAATICAS<br>SHQFLSTHYNLHNLYGLTEA<br>IASHRALVKARGTRPFVISR<br>STFAGHGRYAGHWTGDVWSS<br>WEQLASSVPEILQFNLLGVP<br>LVGADVCGFLGNTSEELCVR<br>WTQLGAFYPFMRNHNSLLSL<br>PQEPYSFSEPAQQAMRKALT<br>LRYALLPHLYTLFHQAHVAG<br>ETVARPLFLEFPKDSSTWTV<br>DHQLLWGEALLITPVLQAGK<br>AEVTGYFPLGTWYDLQTVPI<br>EALGSLPPPPAAPREPAIHS<br>EGQWVTLPAPLDTINVHLRA<br>GYIIPLQGPGLTTTESRQQP<br>MALAVALTKGGEARGELFWD<br>DGESLEVLERGAYTQVIFLA<br>RNNTIVNELVRVTSEGAGLQ<br>LQKVTVLGVATAPQQVLSNG<br>VPVSNFTYSPDTKVLDICVS<br>LLMGEQFLVSWC |
| 2 | cagttgggaaagctgaggtt<br>gtcgccggggccgcgggtgg<br>aggtcggggatgaggcagca<br>ggtaggacagtgacctcggt<br>gacgcgaaggaccccggcca<br>cctctaggttctcctcgtcc<br>gcccgttgttcagcgaggga<br>ggctctgggcctgccgcagc<br>tgacggggaaactgaggcac<br>ggagcgggcctgtaggagct<br>gtccaggccatctccaacca<br>tgggagtgaggcacccgccc<br>tgctcccaccggctcctggc<br>cgtctgcgccctcgtgtcct<br>tggcaaccgctgcactcctg<br>gggcacatcctactccatga<br>tttcctgctggttccccgag<br>agctgagtggctcctcccca<br>gtcctggaggagactcaccc<br>agctcaccagcagggagcca<br>gcagaccagggccccgggat<br>gcccaggcacaccccggccg<br>tcccagagcagtgcccacac<br>agtgcgacgtccccccaac<br>agccgcttcgattgcgcccc<br>tgacaaggccatcacccagg<br>aacagtgcgaggcccgcggc<br>tgctgctacatccctgcaaa<br>gcaggggctgcagggagccc<br>agatggggcagccctggtgc<br>ttcttcccacccagctaccc<br>cagctacaagctggagaacc<br>tgagctcctctgaaatgggc<br>tacacggccaccctgacccg<br>taccaccccaccttcttcc<br>ccaaggacatcctgaccctg<br>cggctggacgtgatgatgga<br>gactgagaaccgcctccact<br>tcacgatcaaagatccagct<br>aacaggcgctacgaggtgcc |

Table 1 -continued
Nucleotide Sequences and Protein Sequences

| SEQ ID NO: | Sequences |
|---|---|
| | cttggagaccccgcgtgtcc |
| | acagccgggcaccgtcccca |
| | ctctacagcgtggagttctc |
| | cgaggagcccttcggggtga |
| | tcgtgcaccggcagctggac |
| | ggccgcgtgctgctgaacac |
| | gacggtggcgccctgttct |
| | ttgcggaccagttccttcag |
| | ctgtccacctcgctgccctc |
| | gcagtatatcacaggcctcg |
| | ccgagcacctcagtccccctg |
| | atgctcagcaccagctggac |
| | caggatcaccctgtggaacc |
| | gggaccttgcgcccacgccc |
| | ggtgcgaacctctacgggtc |
| | tcacccttctacctggcgc |
| | tggaggacggcgggtcggca |
| | cacggggtgttcctgctaaa |
| | cagcaatgccatggatgtgg |
| | tcctgcagccgagccctgcc |
| | cttagctggaggtcgacagg |
| | tgggatcctggatgtctaca |
| | tcttcctgggcccagagccc |
| | aagagcgtggtgcagcagta |
| | cctggacgttgtgggatacc |
| | cgttcatgccgccatactgg |
| | ggcctgggcttccacctgtg |
| | ccgctggggctactcctcca |
| | ccgctatcacccgccaggtg |
| | gtggagaacatgaccagggc |
| | ccacttccccctggacgtcc |
| | aatggaacgacctggactac |
| | atggactcccggagggactt |
| | cacgttcaacaaggatggct |
| | tccgggacttcccggccatg |
| | gtgcaggagctgcaccaggg |
| | cggccggcgctacatgatga |
| | tcgtggatcctgccatcagc |
| | agctcgggcctgccgggag |
| | etacaggccctacgacgagg |
| | gtctgcggagggggggttttc |
| | atcaccaacgagacceggcca |
| | gccgctgattgggaaggtat |
| | ggcccgggtccactgcctc |
| | cccgacttcaccaaccccac |
| | agccctggcctggtgggagg |
| | acatggtggctgagttccat |
| | gaccaggtgccccttcgacgg |
| | catgtggattgacatgaacg |
| | agccttccaacttcatcaga |
| | ggctctgaggacggctgccc |
| | caacaatgagctggagaacc |
| | caccctacgtgcctgggstg |
| | gttggggggaccctccaggc |
| | ggccaccatctgtgcctcca |
| | gccaccagtttctctcxaca |
| | cactacaaactgcacaacct |
| | ctacggcctgaccgaagcca |
| | tcgcctcccacagggcgctg |
| | gtgaaggctcggggggacacg |
| | cccatttgtgatctcccgct |
| | cgacctttgctggccacggc |
| | cgatacgccggccactggac |
| | gggggacgtgtggagctcct |
| | gggagcagctcgcctcctcc |
| | gtgccagaaatctgcagtt |
| | taacctgctgggggtgcctc |
| | tggtcgggccgacgtctgc |
| | ggcttcctgggcaaaeactc |
| | agaggagctgtgtgtgcgct |
| | ggacccagctgggggccttc |
| | tacccttcatgcggaacca |
| | caacagcctgctcagtctgc |
| | cccaggagccgtacagcttc |

| SEQ ID NO: | Sequences |
|---|---|
| | agcgagccggcccagcaggc |
| | catgaggaaggccctcaccc |
| | tgcgctacgcaetcctcccc |
| | cacetctacacactgttcca |
| | ccaggcccacgtcgcggggg |
| | agaccgtggcccggcccctc |
| | ttcctggagttcccccaagga |
| | ctctagcacctggactgtgg |
| | accaccagctcctgtggggg |
| | gaggccctgctcatcacccc |
| | agtgctccaggccgggaagg |
| | ccgaagtgactggctacttc |
| | cccttgggcacatggtacga |
| | cctgcagacggtgccaatag |
| | aggcccttggcagcctccca |
| | cccccacctgcagctcccg |
| | tgagccagccatccacagcg |
| | aggggcagtgggtgacgctg |
| | ccggcccccctggacaccat |
| | caacgtccacctccgggctg |
| | ggtacatcatccccctgcag |
| | ggccctggcctcacaaccac |
| | agagtcccgccagcagccca |
| | tggccctggctgtggccctg |
| | accaagggtggagaggcccg |
| | aggggagctgttctgggacg |
| | atggagagagcctggaagtg |
| | ctggagcgaggggcctacac |
| | acaggtcatcttcctggcca |
| | ggaataaacacgatcgtgaat |
| | gagctggtacgtgtgaccag |
| | tgagggagctggcctgcagc |
| | tgcagaaggtgactgtcctg |
| | ggcgtggccacggcgccccca |
| | gcaggtcctctccaacggtg |
| | tccctgtctccaacttcacc |
| | tacagccccgacaccaaggt |
| | cctggacatctgtgtctcgc |
| | tgttgatgggagagcagttt |
| | ctcgtcagctggtgttagcc |
| | gggcggagtgtgttagtctc |
| | tccagagggaggctggttcc |
| | ccaggaagcagagcctgtg |
| | tgcgggcagcagctgtgtgc |
| | gggcctgggggttgcatgtg |
| | tcacctggagctgggcacta |
| | accattccaagccgccgcat |
| | cgcttgttttccacctcctgg |
| | gccggggctctggcccccaa |
| | cgtgtctaggagagctttct |
| | ccctagatcgcactgtgggc |
| | cggggcctggagggctgctc |
| | tgtgttaataagattgtaag |
| | gtttgccctcctcacctgtt |
| | gccggcatgcgggtagtatt |
| | agccaccccctccatctgt |
| | tcccagcaccggagaaggg |
| | gtgctcaggtggaggtgtgg |
| | ggtatgcacctgagctcctg |
| | cttcgcgcctgctgctctgc |
| | cccaacgcgaccgcttcccg |
| | gctgcccagagggctggatg |
| | cctgccggtccccgagcaag |
| | cctgggaactcaggaaaatt |
| | cacaggacttgggagattct |
| | aaatcttaagtgcaattatt |
| | ttaataaaaggggcatttgg |
| | aatc |
| 3 | MGVRHPPCSHRLLAVCALVS LATAALLGHILLHDFLLVPR ELSGSSPVLEETHPAHQQGA SRPGPRDAQAHPGRPRAVPT QCDVPPNSRFDCAPDKAITQ |

Table 1 -continued

Nucleotide Sequences and Protein Sequences

| SEQ ID NO: | Sequences |
|---|---|
| | EQCEARGCCYTPAKQGLQGA QMGQPWCFFPPSYPSYKLEN LSSSEMGYTATLTRTTPTFF PKDILTLRLDVMMETENRLH FTIKDPANRRYEVPLETPRV HSRAPSPLYSVEFSEEPFGV IVHRQLDGRVLLNTTVAPLF FADQFLQLSTSLPSQYITGL AEHLSPLMLSTSWTRITLWN RDLAPTPGANLYGSHPFYLA LEDGGSAHGVFLLNSNAMDV VLQPSPALSWRSTGGILDVY IFLGPEPKSVVQQYLDVVGY PFMPPYWGLGFHLCRWGYSS TAITRQVVENMTRAHFPLDV QWNDLDYMDSRRDFTFNKDG FRDFPAMVQELHQGGRRYMM IVDPAISSSGPAGSYRPYDE GLRRGVFITNETGQPLIGKV WPGSTAFPDFTNPTALAWWE DMVAEFHDQVPFDGMWIDMN EPSNFIRGSEDGCPNNELEN PPYVPGVVGGTLQAATICAS SHQFLSTHYNLHNLYGLTEA IASHRALVKARGTRPFVISR STFAGHGRYAGHWTGDVWSS WEQLASSVPEILQFNLLGVP LVGADVCGFLGNTSEELCVR WTQLGAFYPFMRNHNSLLSL PQEPYSFSEPAQQAMRKALT LRYALLPHLYTLFHQAHVAG ETVARPLFLEFPKDSSTWTV DHQLLWGEALLITPVLQAGK AEVTGYFPLGTWYDLQTVPI EALGSLPPPPAAPREPAIHS EGQWVTLPAPLDTINVHLRA GYIIPLQGPGLTTTESRQQP MALAVALTKGGEARGELFWD DGESLEVLERGAYTQVIFLA RNNTIVNELVRVTSEGAGLQ LQKVTVLGVATAPQQVLSNG VPVSNFTYSPDTKVLDICVS LLMGEQFLVSWC |
| 4 | MGVRHPPCSHRLLAVCALVS LATAALLGHILLHDFLLVPR ELSGSSPVLEETHPAHQQGA SRPGPRDAQAHPGRPRAVPT QCDVPPNSRFDCAPDKAITQ EQCEARGCCYIPAKQGLQGA QMGQPWCFFPPSYPSYKLEN LSSSEMGYTATLTRTTPTFF PKDILTLRLDVMMETENRLH FTIKDPANRRYEVPLETPHV HSRAPSPLYSVEFSEEPFGV IVRRQLDGRVLGNTTVAPLF FADQFLQLSTSLPSQYITGL AEHLSPLMLSTSWTRITLWN RDLAPTPGANLYGSHPFYLA LEDGGSAHGVFLLNSNAMDV VLQPSPALSWRSTGGILDVY IFLGPEPKSVVQQYLDVVGY PFMPPYWGLGFHLCRWGYSS TAITRQVVENMTRAHFPLDV QWNDLDYMDSRRDFTFNKDG FRDFPAMVQELHQGGRRYMM IVDPAISSSGPAGSYRPYDE GLRRGVFITNETGQPLIGKV WPGSTAFPDFTNPTALAWWE DMVAEFHDQVPFDGMWIDMN EPSNFIRGSEDGCPNNELEN PPYVPGVVGGTLQAATICAS SHQFLSTHYNLHNLYGLTEA IASHRALVKARGTRPFVISR |

Table 1 -continued

Nucleotide Sequences and Protein Sequences

| SEQ ID NO: | Sequences |
|---|---|
| | STFAGHGRYAGHWTGDVWSS WEQLASSVPEILQFNLLGVP LVGADVCGFLGNTSEELCVR WTQLGAFYPFMRNHNSLLSL PQEPYSFSEPAQQAMRKALT LRYALLPHLYTLFHQAHVAG ETVARPLFLEFPKDSSTWTV DHQLLWGEALLITPVLQAGK AEVTGYFPLGTWYDLQTVPV EALGSLPPPPAAPREPAIHS EGQWVTLPAPLDTINVHLRA GYIIPLQGPGLTTTESRQQP MALAVALTKGGEARGELFWD DGESLEVLERGAYTQVIFLA RNNTIVNELVRVTSEGAGLQ LQKVTVLGVATAPQQVLSNG VPVSNFTYSPDTKVLDICVS LLMGEQFLVSWC |
| 5 | QQGASRPGPRDAQAHPGRPR AVPTQCDVPPNSRFDCAPDK AITQEQCEARGCCYIPAKQG LQGAQMGQPWCFFPPSYPSY KLENLSSSEMGYTATLTRTT PTFFPKDILTLRLDVMMETE NRLHFTIKDPANRRYEVPLE TPRVHSRAPSPLYSVEFSEE PFGVIVHRQLDGRVLLNTVV APLFFADQFLQLSTSLPSQY ITGLAEHLSPLMLSTSWTRI TLWNRDLAPTPGANLYGSHP FYLALEDGGSAHGVFLLNSN AMDVVLQPSPALSWRSTGGI LDVYTFLGPEPKSVVQQYLD VVGYPFMPPYWGLGFHLCRW GYSSTAITRQVVENMTRAHF PLDVQWNDLDYMDSRRDFTF NKDGFRDFPAMVQELHQGGR RYMMIVDPAISSSGPAGSYR PYDEGLRRGVFITNETGQPL IGKVWPGSTAFPDFTNPTAL AWWEDMVAEFHDQVPFDGMW IDMNEPSNFIRGSEDGCPNN ELENPPYVPGVVGGTLQAAT ICASSHQFLSTHYNLHNLYG LTEAIASHRALVKARGTRPF VISRSTFAGHGRYAGHWTGD VWSSWEQLASSVPETLQFNL LGVPLVGADVCGFLGNTSEE LCVRWTQLGAFYPFMRNHNS LLSLPQEPYSFSEPAQQAMR KALTERYALLPHLYTLFHQA HVAGETVARPLFLEFPKDSS TWTVDHQLLWGEALLITPVL QAGKAEVTGYFPLGTWYDLQ TVPIEALGSLPPPPAAPREP ATHSEGQWVTLPAPLDTINV HLRAGYIIPLQGPGLTTTES RQQPMALAVALTKGGEARGE LFWDDGESLEVLERGAYTQV IFLARNNTIVNELVRVTSEG AGLQLQKVTVLGVATAPQQV LSNGVPVSNFTYSPDTKVLD ICVSLLMGEQFLVSWC |

In some embodiments, the rhGAA has a wild-type GAA amino acid sequence as set forth in SEQ ID NO: 1, as described in U.S. Pat. No. 8,592,362 and has GenBank accession number AHE24104.1 (GI:568760974). In some embodiments, the rhGAA has a wild-type GAA amino acid sequence as encoded in SEQ ID NO: 2, the mRNA sequence having GenBank accession number Y00839.1. In some embodiments, the rhGAA has a wild-type GAA amino acid sequence as set forth in SEQ ID NO: 3. In at some embodiments, the rhGAA has a GAA amino acid sequence as set forth in SEQ ID NO: 4, and has National Center for Biotechnology Information (NCBI) accession number NP 000143.2. In some embodiments, the rhGAA is alglucosidase alfa, the human acid α-glucosidase enzyme encoded by the most predominant of nine observed haplotypes of the GAA gene.

In some embodiments, the rhGAA is initially expressed as having the full-length 952 amino acid sequence of wild-type GAA as set forth in SEQ ID NO: 1, and the rhGAA undergoes intracellular processing that removes a portion of the amino acids, e.g. the first 56 amino acids. Accordingly, the rhGAA that is secreted by the host cell can have a shorter amino acid sequence than the rhGAA that is initially expressed within the cell. In one embodiment, the shorter protein has the amino acid sequence set forth in SEQ ID NO: 5, which only differs from SEQ ID NO: 1 in that the first 56 amino acids comprising the signal peptide and precursor peptide have been removed, thus resulting in a protein having 896 amino acids. Other variations in the number of amino acids are also possible, such as having 1, 2, 3, 4, 5, 6, 7, 8, 9, 10, 11, 12, 13, 14, 15, or more deletions, substitutions and/or insertions relative to the amino acid sequence described by SEQ ID NO: 1 or SEQ ID NO: 5. In some embodiments, the rhGAA product includes a mixture of recombinant human acid α-glucosidase molecules having different amino acid lengths.

In some embodiments, the rhGAA comprises an amino acid sequence that is at least 90%, 95%, 98% or 99% identical to SEQ ID NO: 1 or SEQ ID NO: 5. Various alignment algorithms and/or programs may be used to calculate the identity between two sequences, including FASTA, or BLAST which are available as a part of the GCG sequence analysis package (University of Wisconsin, Madison. Wis.), and can be used with, e.g., default setting. For example, polypeptides having at least 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical: and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

In some embodiments, the rhGAA undergoes post-translational and/or chemical modifications at one or more amino acid residues in the protein. For example, methionine and tryptophan residues can undergo oxidation. As another example, the N-terminal glutamine can form pyro-glutamate. As another example, asparagine residues can undergo deamidation to aspartic acid. As yet another example, aspartic acid residues can undergo isomerization to iso-aspartic acid. As yet another example, unpaired cysteine residues in the protein can form disulfide bonds with free glutathione and/or cysteine. Accordingly, in some embodiments, the enzyme is initially expressed as having an amino acid sequence as set forth in SEQ ID NO: 1, SEQ ID NO: 3, SEQ ID NO: 4, or SEQ ID NO: 5, or an amino acid sequence encoded by SEQ ID NO: 2 and the enzyme undergoes one or more of these post-translational and/or chemical modifications. Such modifications are also within the scope of the present disclosure.

III. N-Linked Glycosylation of rhGAA

There are seven potential N-linked glycosylation sites on a single rhGAA molecule. These potential glycosylation sites are at the following positions of SEQ ID NO: 5: N84, N177, N334, N414, N596, N826, and N869. Similarly, for the full-length amino acid sequence of SEQ ID NO: 1, these potential glycosylation sites are at the following positions: N140, N233, N390, N470, N652, N882, and N925. Other variants of rhGAA can have similar glycosylation sites, depending on the location of asparagine residues. Generally, sequences of Asn-X-Ser or Asn-X-Thr in the protein amino acid sequence indicate potential glycosylation sites, with the exception that X cannot be His or Pro.

The rhGAA molecules described herein may have, on average, 1, 2, 3, or 4 mannose-6-phosphate (M6P) groups on their N-glycans. For example, only one N-glycan on a rhGAA molecule may bear M6P (mono-phosphorylated or mono-M6P), a single N-glycan may bear two M6P groups (bis-phosphorylated or bis-M6P), or two different N-glycans on the same rhGAA molecule may each bear single M6P groups. In some embodiments, the rhGAA molecules described herein on average have 3-4 M6P groups on their N-glycans. Recombinant human acid α-glucosidase molecules may also have N-glycans bearing no M6P groups. In another embodiment, on average the rhGAA comprises greater than 2.5 mol M6P per mol rhGAA and greater than 4 mol sialic acid per mol rhGAA. In some embodiments, on average the rhGAA comprises about 3-3.5 mol M6P per mol rhGAA. In some embodiments, on average the rhGAA comprises about 4-5.4 mol sialic acid per mol rhGAA. On average at least about 3, 4, 5, 6, 7, 8, 9, 10%, or 20% of the total N-glycans on the rhGAA may be in the form of a mono-M6P N-glycan, for example, about 6.25% of the total N-glycans may carry a single M6P group and on average, at least about 0.5, 1, 1.5, 2.0, 2.5, 3.0% of the total N-glycans on the rhGAA are in the form of a bis-M6P N-glycan and on average less than 25% of total rhGAA contains no phosphorylated N-glycan binding to CIMPR. In some embodiments, on average about 10% to about 14% of the total N-glycans on the rhGAA are mono-phosphorylated. In some embodiments, on average about 7% to about 25% of the total N-glycans on the rhGAA are bis-phosphorylated. In some embodiments, on average the rhGAA comprises about 1.3 mol bis-M6P per mol rhGAA.

The rhGAA described herein may have an average content of N-glycans carrying M6P ranging from 0.5 to 7.0 mol M6P per mol rhGAA or any intermediate value or subrange thereof including 0.5, 1.0, 1.5, 2.0, 2.5, 3.0, 3.5, 4.0, 4.5, 5.0, 5.5, 6.0, 6.5, or 7.0 mol M6P per mol rhGAA. The rhGAA can be fractionated to provide rhGAA preparations with different average numbers of mono-M6P-bearing or bis-M6P-bearing N-glycans, thus permitting further customization of rhGAA targeting to the lysosomes in target tissues by selecting a particular fraction or by selectively-combining different fractions.

In some embodiments, up to 60% of the N-glycans on the rhGAA may be fully sialylated, for example, up to 10%, 20%, 30%, 40%, 50% or 60% of the N-glycans may be fully sialylated. In some embodiments, no more than 50% of the N-glycans on the rhGAA are fully sialylated. In some embodiments, from 4% to 20% of the total N-glycans are fully sialylated. In other embodiments, no more than 5%, 10%, 20% or 30% of N-glycans on the rhGAA carry sialic acid and a terminal galactose residue (Gal). This range includes all intermediate values and subranges, for example, 7% to 30% of the total N-glycans on the rhGAA can carry sialic acid and terminal galactose. In yet other embodiments, no more than 5%, 10%, 15%, 16%, 17%, 18%, 19%, or 20% of the N-glycans on the rhGAA have a terminal galactose only and do not contain sialic acid. This range includes all intermediate values and subranges, for example, from 8% to 19% of the total N-glycans on the rhGAA in the composition may have terminal galactose only and do not contain sialic acid.

In some embodiments, 40% 45%, 50%, or 55% to 60% of the total N-glycans on the rhGAA are complex type N-glycans; or no more than 1%, 2%, 3%, 4%, 5% 6,%, or 7% of total N-glycans on the rhGAA are hybrid-type N-glycans; no more than 5%, 10%, 15%, 20%, or 25% of the high mannose-type N-glycans on the rhGAA are non-phosphorylated; at least 5% or 10% of the high mannose-type N-glycans on the rhGAA are mono-phosphorylated; and/or at least 1% or 2% of the high mannose-type N-glycans on the rhGAA are bis-phosphorylated. These values include all intermediate values and subranges. A rhGAA may meet one or more of the content ranges described above.

In some embodiments, the rhGAA may bear, on average, 2.0 to 8.0 moles of sialic acid residues per mole of rhGAA. This range includes all intermediate values and subranges thereof, including 2.0, 2.5, 3.0, 3.5, 4.0, 4.5, 5.0, 5.5, 6.0, 6.5, 7.0, 7.5, and 8.0 mol sialic acid residues per mol rhGAA. Without being bound by theory, it is believed that the presence of N-glycan units bearing sialic acid residues may prevent non-productive clearance of the rhGAA by asialoglycoprotein receptors.

Figure 6A:
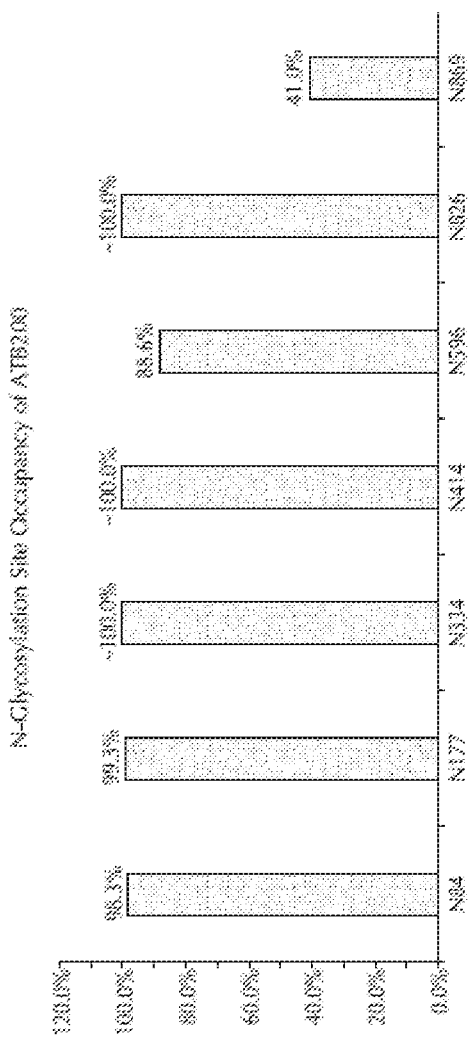
FIGS. 6A-6H show the results of a site-specific N-glycosylation analysis of ATB200 rhGAA, using two different LC-MS/MS analytical techniques.
Figure 6B:
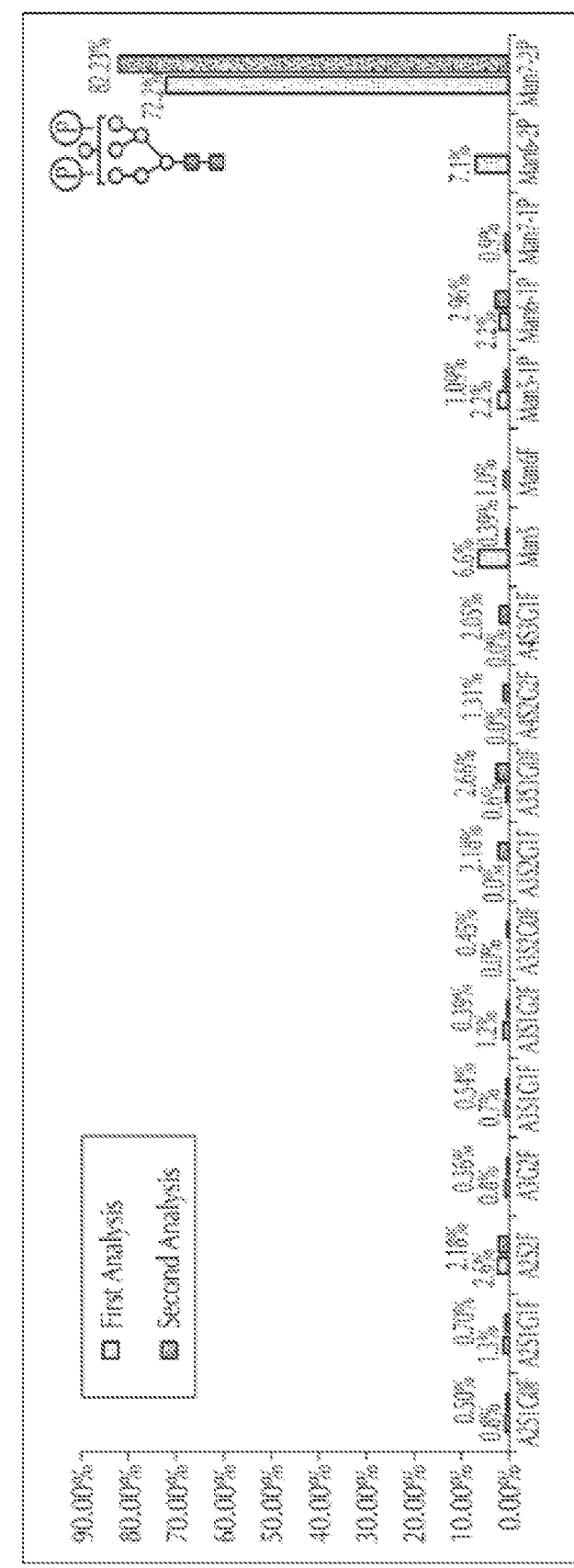

In one or more embodiments, the rhGAA has a certain N-glycosylation profile at certain potential N-glycosylation sites. In some embodiments, the rhGAA has seven potential N-glycosylation sites. In some embodiments, at least 20% of the rhGAA is phosphorylated at the first potential N-glycosylation site (e.g., N84 for SEQ ID NO: 5 and N140 for SEQ ID NO: 1). For example, at least 20%, 25%, 30%, 35%, 40%, 45%, 50%, 55%, 60%, 65%, 70%, 75%, 80%, 85%, 90%, or 95% of the rhGAA can be phosphorylated at the first potential N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90%, or 95% of the rhGAA bears a mono-M6P unit at the first potential N-glycosylation site. In some embodiments, at least 10%, 15%, 20%, 25%, 30%, 35%, 40%, 45%, 50%, 55%, 60%, 65%, 70%, 75%, 80%, 85%, 90%, or 95% of the rhGAA bears a bis-M6P unit at the first potential N-glycosylation site. In some embodiments, the rhGAA comprises on average about 1.4 mol M6P (mono-M6P and bis-M6P) per mol rhGAA at the first potential N-glycosylation site. In some embodiments, the rhGAA comprises on average about at least 0.5 mol bis-M6P per mol rhGAA at the first potential N-glycosylation site. In some embodiments, the rhGAA comprises on average about 0.25 mol mono-M6P per mol rhGAA at the first potential N-glycosylation site. In some embodiments, the rhGAA comprises on average about 0.2 mol to about 0.3 mol sialic acid per mol rhGAA at the first potential N-glycosylation site. In at least one embodiment, the rhGAA comprises a first potential N-glycosylation site occupancy as depicted in FIG. 6A and an N-glycosylation profile as depicted in FIG. 6B. In at least one embodiment, the rhGAA comprises a first potential N-glycosylation site occupancy as depicted in FIG. 32A and an N-glycosylation profile as depicted in FIG. 32B or FIG. 33B.

Figure 6C:
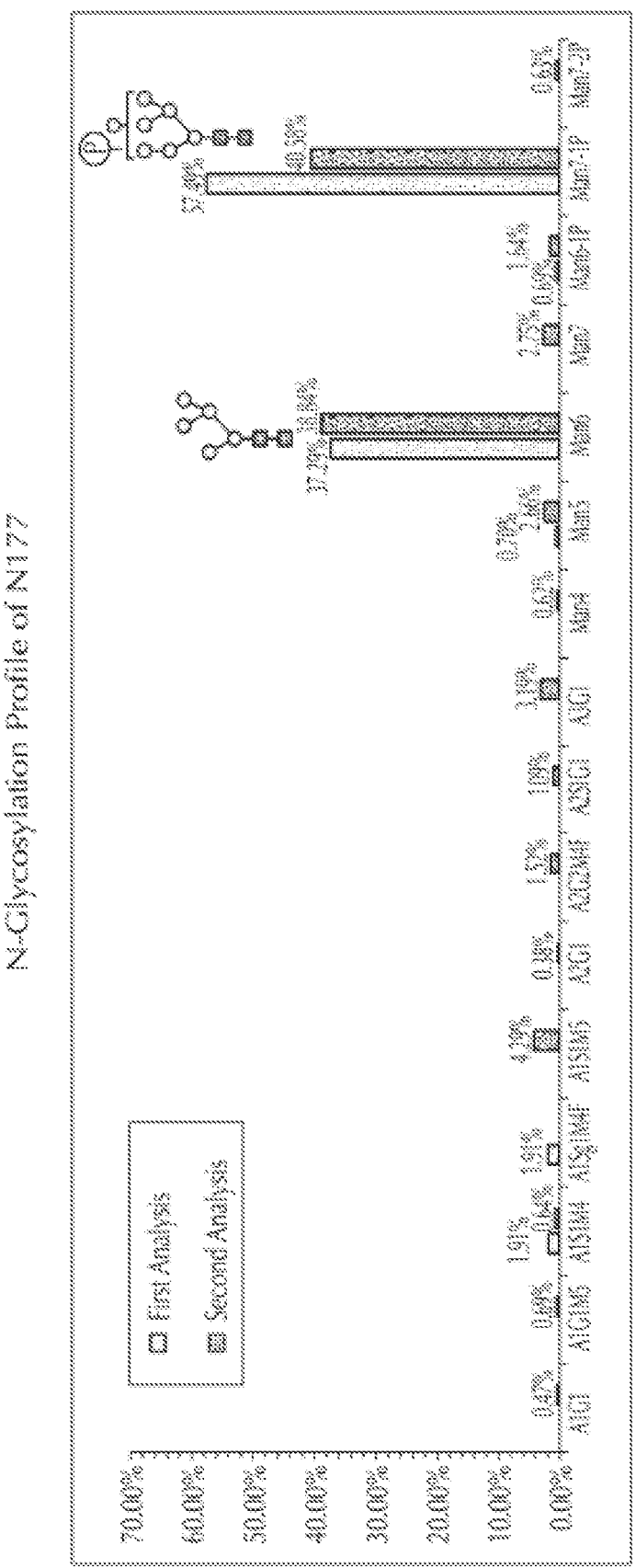

In some embodiments, at least 20% of the rhGAA is phosphorylated at the second potential N-glycosylation site (e.g., N177 for SEQ ID NO: 5 and N223 for SEQ ID NO: 1). For example, at least 20%, 25%, 30%, 35%, 40%, 45%, 50%, 55%, 60%, 65%, 70%, 75%, 80%, 85%, 90%, or 95% of the rhGAA can be phosphorylated at the second N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65% 70% 75%, 80%, 85% 90% or 95% of the rhGAA bears a mono-M6P unit at the second N-glycosylation site. In some embodiments, at least 10% 15%, 20%, 25%, 30%, 35%, 40%, 45%, 50% 55% 60%, 65% 70% 75%, 80% 85%, 90%, or 95% of the rhGAA bears a bis-M6P unit at the second N-glycosylation site. In some embodiments, the rhGAA comprises on average about 0.5 mol M6P (mono-M6P and bis-M6P) per mol rhGAA at the second potential N-glycosylation site. In some embodiments, the rhGAA comprises on average about 0.4 to about 0.6 mol mono-M6P per mol rhGAA at the second potential N-glycosylation site. In at least one embodiment, the rhGAA comprises a second potential N-glycosylation site occupancy as depicted in FIG. 6A and an N-glycosylation profile as depicted in FIG. 6C. In at least one embodiment, the rhGAA comprises a second potential N-glycosylation site occupancy as depicted in FIG. 32A and an N-glycosylation profile as depicted in FIG. 32C or FIG. 33B.

Figure 6D:
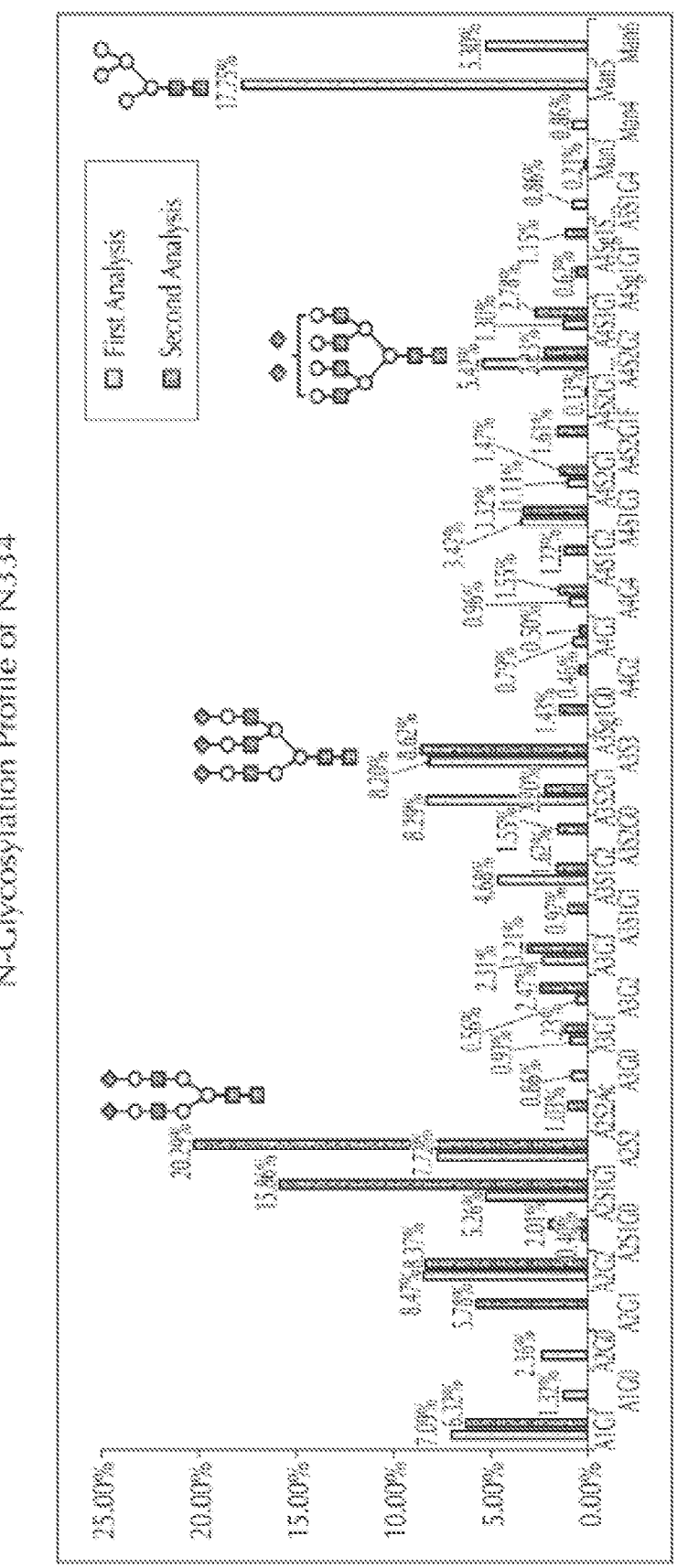

In one or more embodiments, at least 5% of the rhGAA is phosphorylated at the third potential N-glycosylation site (e.g., N334 for SEQ ID NO: 5 and N390 for SEQ ID NO: 1). In other embodiments, less than 5%, 10%, 15%, 20%, or 25% of the rhGAA is phosphorylated at the third potential N-glycosylation site. For example, the third potential N-glycosylation site can have a mixture of non-phosphorylated high mannose N-glycans, di-, tri-, and tetra-antennary complex N-glycans, and hybrid N-glycans as the major species. In some embodiments, at least 3%, 5%, 8%, 10%, 15%, 20%, 25%, 30%, 35%, 40%, 45%, or 50% of the rhGAA is sialylated at the third potential N-glycosylation site. In some embodiments, the rhGAA comprises on average about 0.9 to about 1.2 mol sialic acid per mol rhGAA at the third potential N-glycosylation site. In at least one embodiment, the rhGAA comprises a third potential N-glycosylation site occupancy as depicted in FIG. 6A and an N-glycosylation profile as depicted in FIG. 6D. In at least one embodiment, the rhGAA comprises a third potential N-glycosylation site occupancy as depicted in FIG. 32A and an N-glycosylation profile as depicted in FIG. 32D or FIG. 33B.

Figure 6E:
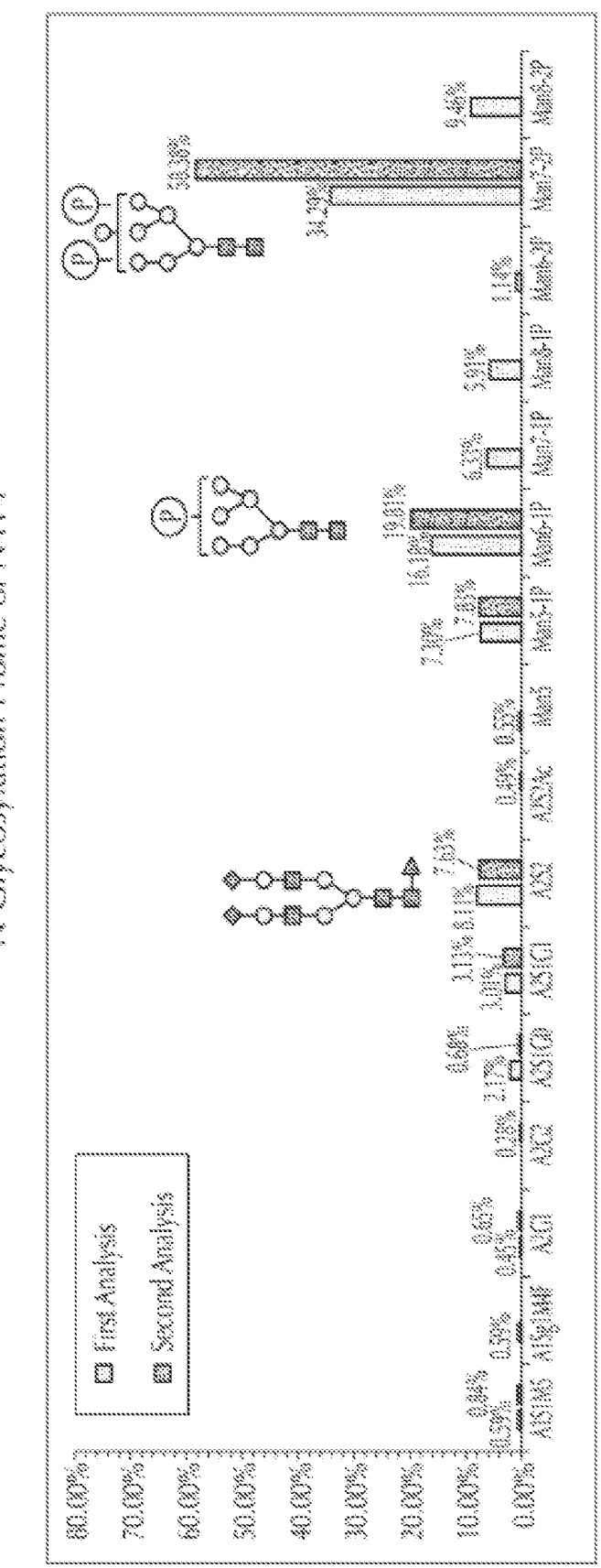

In some embodiments, at least 20% of the rhGAA is phosphorylated at the fourth potential N-glycosylation site (e.g., N414 for SEQ ID NO: 5 and N470 for SEQ ID NO: 1). For example, at least 20%, 25%, 30%, 35%, 40%, 45%, 50%, 55%, 60%, 65%, 70%, 75%, 80%, 85%, 90%, or 95% of the rhGAA can be phosphorylated at the fourth potential N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65% 70% 75%, 80%, 85% 90% or 95% of the rhGAA bears a mono-M6P unit at the fourth potential N-glycosylation site. In some embodiments, at least 10%, 15%, 20%, 25%, 30% 35%, 40%, 45% 50%, 55%, 60%, 65%, 70% 75%, 80% 85%, 90%, or 95% of the rhGAA bears a bis-M6P unit at the fourth potential N-glycosylation site. In some embodiments, at least 3%, 5%, 8%, 10%, 15% 20%, or 25% of the rhGAA is sialylated at the fourth potential N-glycosylation site. In some embodiments, the rhGAA comprises on average about 1.4 mol M6P (mono-M6P and bis-M6P) per mol rhGAA at the fourth potential N-glycosylation site. In some embodiments, the rhGAA comprises on average about 0.4 to about 0.6 mol bis-M6P per mol rhGAA at the fourth potential N-glycosylation site. In some embodiments, the rhGAA comprises on average about 0.3 to about 0.4 mol mono-M6P per mol rhGAA at the fourth potential N-glycosylation site. In at least one embodiment, the rhGAA comprises a fourth potential N-glycosylation site occupancy as depicted in FIG. 6A and an N-glycosylation profile as depicted in FIG. 6E. In at least one embodiment, the rhGAA comprises a fourth potential N-glycosylation site occupancy as depicted in FIG. 32A and an N-glycosylation profile as depicted in FIG. 32E or FIG. 33B.

Figure 6F:
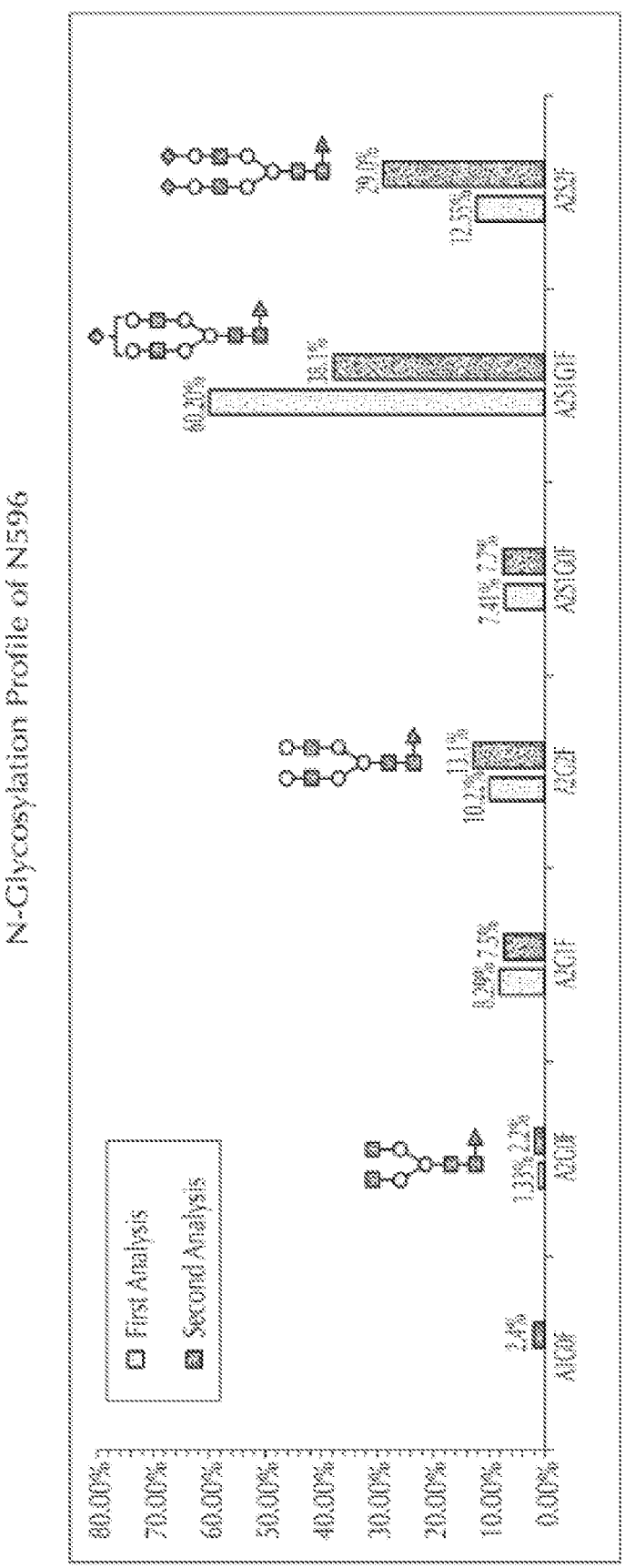

In some embodiments, at least 5% of the rhGAA is phosphorylated at the fifth potential N-glycosylation site (e.g., N596 for SEQ ID NO: 5 and N692 for SEQ ID NO: 1). In other embodiments, less than 5%, 10%, 15% 20%, or 25% of the rhGAA is phosphorylated at the fifth potential N-glycosylation site. For example, the fifth potential N-glycosylation site can have fucosylated di-antennary complex N-glycans as the major species. In some embodiments, at least 3%, 5% 8% 10%, 15%, 20%, 25%, 30%, 35%, 40% 45% 50%, 55% 60% 65%, 70% 75%, 80%, 85% 90%, or 95% of the rhGAA is sialylated at the fifth potential N-glycosylation site. In some embodiments, the rhGAA comprises on average about 0.8 to about 0.9 mol sialic acid per mol rhGAA at the fifth potential N-glycosylation site. In at least one embodiment, the rhGAA comprises a fifth potential N-glycosylation site occupancy as depicted in FIG. 6A and an N-glycosylation profile as depicted in FIG. 6F. In at least one embodiment, the rhGAA comprises a fifth potential N-glycosylation site occupancy as depicted in FIG. 32A and an N-glycosylation profile as depicted in FIG. 32F or FIG. 33B.

Figure 6G:
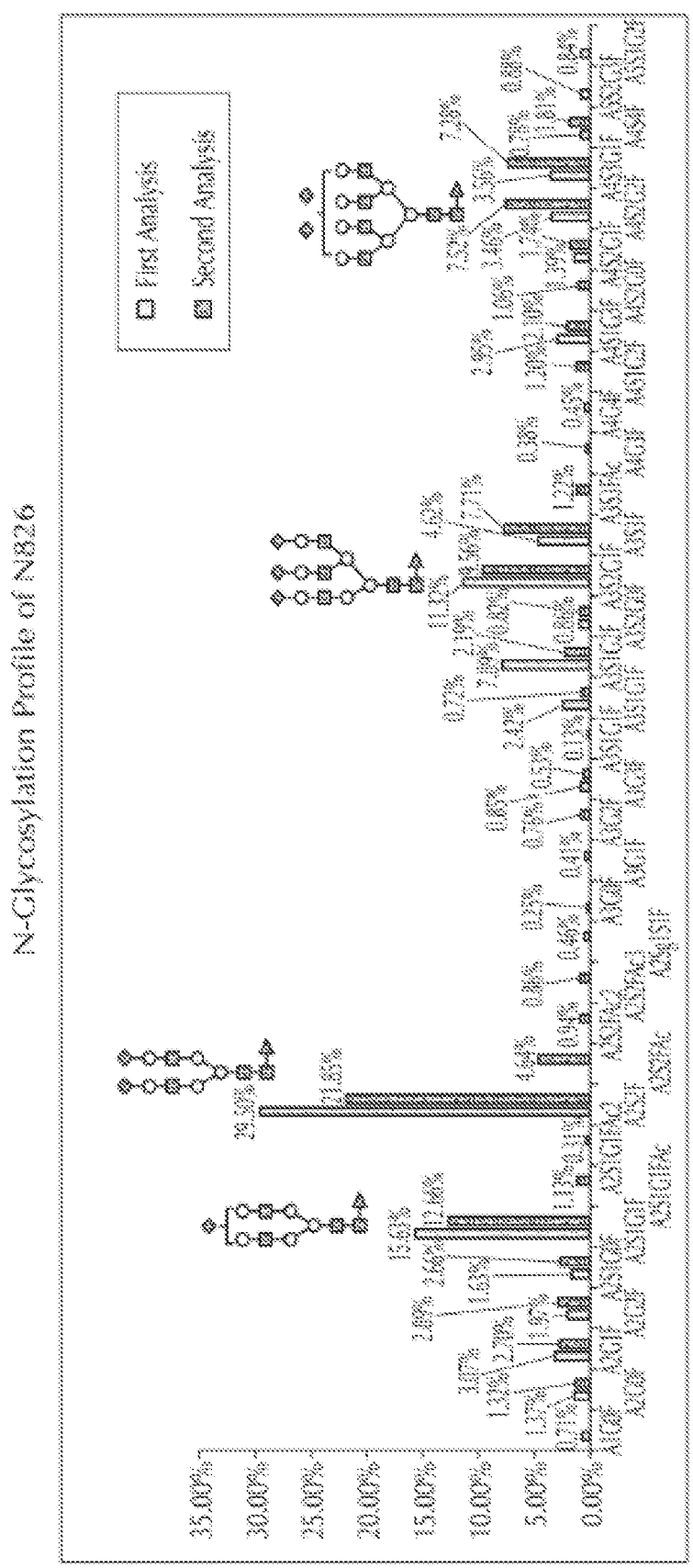

In some embodiments, at least 5% of the rhGAA is phosphorylated at the sixth N-glycosylation site (e g. N826 for SEQ ID NO: 5 and N882 for SEQ ID NO: 1). In other embodiments, less than 5%, 10% 15% 20% or 25% of the rhGAA is phosphorylated at the sixth N-glycosylation site. For example, the sixth N-glycosylation site can have a mixture of di-, tri-, and tetra-antennary complex N-glycans as the major species. In some embodiments, at least 3%, 5% 8%, 10%, 15% 20% 25%, 30% 35%, 40%, 45% 50% 55%, 60%, 65% 70%, 75% 80%, 85%, 90% or 95% of the rhGAA is sialylated at the sixth N-glycosylation site. In some embodiments, the rhGAA comprises on average about 1.5 to about 4.2 mol sialic acid per mol rhGAA at the sixth potential N-glycosylation site. In some embodiments, the rhGAA comprises on average about 0.9 mol acetylated sialic acid per mol rhGAA at the sixth potential N-glycosylation site. In at least one embodiment, the rhGAA comprises a sixth potential N-glycosylation site occupancy as depicted in FIG. 6A and an N-glycosylation profile as depicted in FIG. 6G. In at least one embodiment, the rhGAA comprises a sixth potential N-glycosylation site occupancy as depicted in FIG. 32A and an N-glycosylation profile as depicted in FIG. 32G or FIG. 33B.

In some embodiments, at least 5% of the rhGAA is phosphorylated at the seventh potential N-glycosylation site (e.g., N869 for SEQ ID NO: 5 and N925 for SEQ ID NO: 1). In other embodiments, less than 5% 10% 15%, 20%, or 25% of the rhGAA is phosphorylated at the seventh potential N-glycosylation site. In some embodiments, less than 40%, 45%, 50% 55%, 60%, or 65% of the rhGAA has any N-glycan at the seventh potential N-glycosylation site. In some embodiments, at least 30% 35%, or 40% of the rhGAA has an N-glycan at the seventh potential N-glycosylation site. In some embodiments, the rhGAA comprises on average about 0.86 mol sialic acid per mol rhGAA at the seventh potential N-glycosylation site. In at least on embodiment, all N-glycans identified at the seventh potential N-glycosylation site are complex N-glycans. In at least one embodiment, the rhGAA comprises a seventh potential N-glycosylation site occupancy as depicted in FIG. 6A or as depicted in FIG. 32A and an N-glycosylation profile as depicted in FIG. 32H or FIG. 33B.

In some embodiments, the rhGAA comprises on average 3-4 M6P residues per rhGAA molecule and about 4 to about 7.3 mol sialic acid per mol rhGAA. In some embodiments, the rhGAA further comprises on average at least about 0.5 mol bis-M6P per mol rhGAA at the first potential N-glycosylation site, about 0.4 to about 0.6 mol mono-M6P per mol rhGAA at the second potential N-glycosylation site, about 0.9 to about 1.2 mol sialic acid per mol rhGAA at the third potential N-glycosylation site, about 0.4 to about 0.6 mol bis-M6P per mol rhGAA at the fourth potential N-glycosylation site, about 0.3 to about 0.4 mol mono-M6P per mol rhGAA at the fourth potential N-glycosylation site, about 0.8 to about 0.9 mol sialic acid per mol rhGAA at the fifth potential N-glycosylation site, and about 1.5 to about 4.2 mol sialic acid per mol rhGAA at the sixth potential N-glycosylation site. In at least one embodiment, the rhGAA further comprises on average about 0.86 mol sialic acid per mol rhGAA at the seventh potential N-glycosylation site. In at least one embodiment, the rhGAA comprises seven potential N-glycosylation sites with occupancy and N-glycosylation profiles as depicted in FIGS. 6A-6H. In at least one embodiment, the rhGAA comprises seven potential N-glycosylation sites with occupancy and N-glycosylation profiles as depicted in FIGS. 32A-32H and FIGS. 33A-33B.

Methods of making rhGAA are disclosed in U.S. Provisional Patent Application No. 62/057,842, filed Sep. 30, 2014, the entire content of which is incorporated herein by reference.

Figures 2A, 2B:
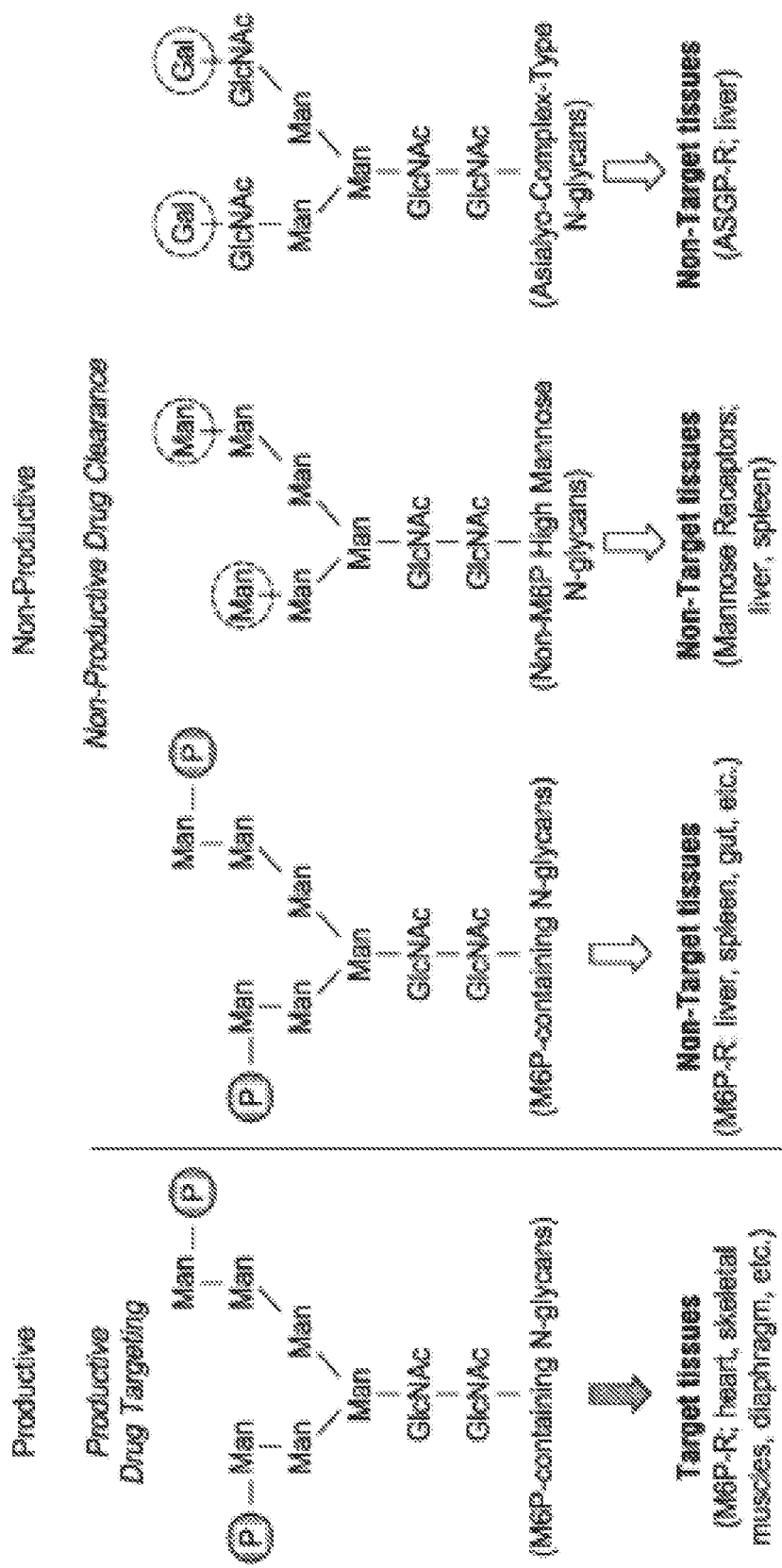
FIG. 2A describes productive targeting of rhGAA via N-glycans bearing M6P to target tissues (e.g. muscle tissues of subject with Pompe Disease).
FIG. 2B describes non-productive drug clearance to non-target tissues (e.g. liver and spleen) or by binding of non-M6P N-glycans to non-target tissues.

Once inside the lysosome, rhGAA can enzymatically degrade accumulated glycogen. However, conventional rhGAA products have low total levels of mono-M6P- and bis-M6P bearing N-glycans and, thus, target muscle cells poorly, resulting in inferior delivery of rhGAA to the lysosomes. The majority of rhGAA molecules in these conventional products do not have phosphorylated N-glycans, thereby lacking affinity for the CIMPR. Non-phosphorylated high mannose N-glycans can also be cleared by the mannose receptor, which results in non-productive clearance of the ERT (FIG. 2B). In contrast, as shown in FIG. 2A, a rhGAA described herein may contains a higher amount of mono-M6P- and bis-M6P bearing N-glycans, leading to productive uptake of rhGAA into specific tissues such as muscle.

IV. Production and Purification of N-Linked Glycosylated rhGAA

As described in International Application PCT/US2015/053252, the entirety of which is incorporated herein by reference, cells such as Chinese hamster ovary (CHO) cells may be used to produce the rhGAA described therein. Expressing high M6P rhGAA in CHO cells is advantageous over modifying the glycan profile of an rhGAA post-translationally at least in part because only the former may be converted by glycan degration to a form of rhGAA with optimal glycogen hydrolysis, thus enhancing therapeutic efficacy.

In some embodiments, the rhGAA is preferably produced by one or more CHO cell lines that are transformed with a DNA construct encoding the rhGAA described therein. Such CHO cell lines may contain multiple copies of a gene, such as S, 10, 15, or 20 or more copies, of a polynucleotide encoding GAA. DNA constructs, which express allelic variants of acid α-glucosidase or other variant acid α-glucosidase amino acid sequences such as those that are at least 90%, 95%, 98%, or 99% identical to SEQ ID NO: 1 or SEQ ID NO: 5, may be constructed and expressed in CHO cells. Those of skill in the art may select alternative vectors suitable for transforming CHO cells for production of such DNA constructs.

Methods for making such CHO cell lines are described in International Application PCT/US2015/053252, the entirety of which is incorporated herein by reference. Briefly, these methods involve transforming a CHO cell with DNA encoding GAA or a GAA variant, selecting a CHO cell that stably integrates the DNA encoding GAA into its chromosome(s) and that stably expresses GAA, and selecting a CHO cell that expresses GAA having a high content of N-glycans bearing mono-M6P or bis-M6P, and, optionally, selecting a CHO cell having N-glycans with high sialic acid content and/or having N-glycans with a low non-phosphorylated high-mannose content. The selected CHO cell lines may be used to produce rhGAA and rhGAA compositions by culturing the CHO cell line and recovering said composition from the culture of CHO cells. In some embodiments, a rhGAA produced from the selected CHO cell lines contains a high content of N-glycans bearing mono-M6P or bis-M6P that target the CIMPR. In some embodiments, a rhGAA produced as described herein has low levels of complex N-glycans with terminal galactose. In some embodiments, the selected CHO cell lines are referred to as GA-ATB200 or ATB200-X5-14. In some embodiments, the selected CHO cell lines encompass a subculture or derivative of such a CHO cell culture. In some embodiments, a rhGAA produced from the selected CHO cell lines is referred to as ATB200.

Figure 3:
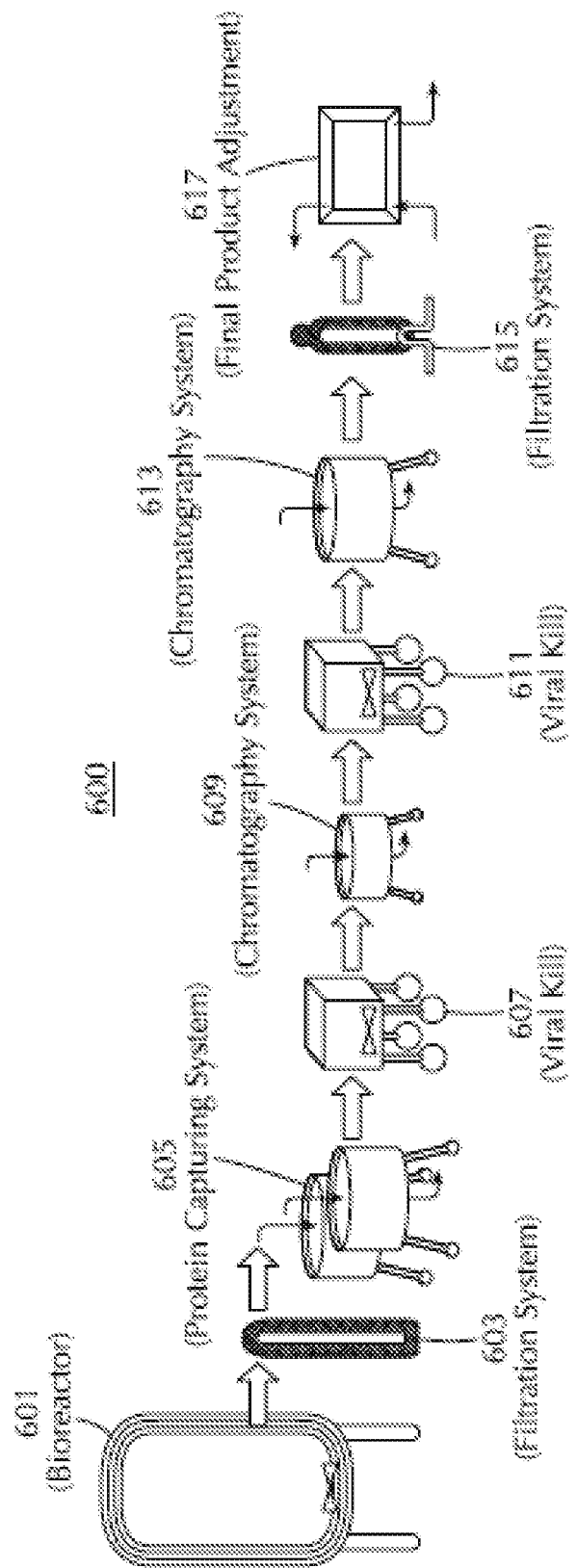
FIG. 3 is a schematic diagram of an exemplary process for the manufacturing, capturing and purification of a recombinant lysosomal protein.

A rhGAA produced as described herein may be purified by following methods described in International Application PCT/US2017/024981 and in U.S. Provisional Application No. 62/506,569, both of which are incorporated herein by reference in their entirety. An exemplary process for producing, capturing, and purifying a rhGAA produced from CHO cell lines is shown in FIG. 3.

Briefly, bioreactor 601 contains a culture of cells, such as CHO cells, that express and secrete rhGAA into the surrounding liquid culture media. The bioreactor 601 may be any appropriate bioreactor for culturing the cells, such as a perfusion, batch or fed-batch bioreactor. The culture media is removed from the bioreactor after a sufficient period of time for cells to produce rhGAA. Such media removal may be continuous for a perfusion bioreactor or may be batchwise for a batch or fed-batch reactor. The media may be filtered by filtration system 603 to remove cells. Filtration system 603 may be any suitable filtration system, including an alternating tangential flow filtration (ATF) system, a tangential flow filtration (TFF) system, and/or centrifugal filtration system. In various embodiments, the filtration system utilizes a filter having a pore size between about 10 nanometers and about 2 micrometers.

After filtration, the filtrate is loaded onto a protein capturing system 605. The protein capturing system 605 may include one or more chromatography columns. If more than one chromatography column is used, then the columns may be placed in series so that the next column can begin loading once the first column is loaded. Alternatively, the media removal process can be stopped during the time that the columns are switched.

In various embodiments, the protein capturing system 605 includes one or more anion exchange (AEX) columns for the direct product capture of rhGAA, particularly rhGAA having a high M6P content. The rhGAA captured by the protein capturing system 605 is eluted from the column(s) by changing the pH and/or salt content in the column. Exemplary conditions for an AEX column are provided in Table 2.

TABLE 2

Exemplary conditions for an AEX column

| Procedure | Buffer | Flow rate (cm/h) | Volume (CV) | Temperature (° C.) |
|---|---|---|---|---|
| Pre-used Sanitization | 0.1-10M NaOH | ≤25-2500 | ≥1-3 (≥10-120 min) | 15-25 |
| Pre-Equilibration | 20-2000 mM phosphate buffer (PB), pH 6 9-7.3 | ≤25-2500 | ≥1-5 | 15-25 |
| Equilibration | 4-400 mM PB, pH 6.9-7.3 | ≤25-2500 | ≥1-5 | 2-15 |
| Load | NA | ≤10-1000 | NA | 2-15 |
| Wash1 | 4-400 mM PB, pH 6.9-7.3 | ≤25-2500 | ≥2-10 | 2-15 |
| Wash2 | 4-400 mM PB, pH 6.9-7.3 | ≤25-2500 | ≥2-10 | 15-25 |
| Elution | 4-400 mM PB, 20-2000 mM NaCl, pH 6.1-6.5 | ≤25-2500 | NA | 15-25 |
| Strip | 4-400 mM PB, 0.1-10 M NaCl, pH 6.1-6.5 | ≤25-2500 | ≥1-5 | 15-25 |
| Post-use Sanitization | 0.1-10M NaOH | ≤25-2500 | ≥1-3 (≥10-120 min) | 15-25 |
| Storage | 0.01-1.0M NaOH | ≤25-2500 | ≥1-5 | 15-25 |

The eluted rhGAA can be subjected to further purification steps and/or quality assurance steps. For example, the eluted rhGAA may be subjected to a virus kill step 607. Such a virus kill 607 may include one or more of a low pH kill, a detergent kill, or other technique known in the art. The rhGAA from the virus kill step 607 may be introduced into a second chromatography system 609 to further purify the rhGAA product. Alternatively, the eluted rhGAA from the protein capturing system 605 may be fed directly to the second chromatography system 609. In various embodiments, the second chromatography system 609 includes one or more immobilized metal affinity chromatography (IMAC) columns for further removal of impurities. Exemplary conditions for an IMAC column are provided in Table 3 below.

TABLE 3

Exemplary conditions for an IMAC column

| Procedure | Buffer | Flow rate (cm/h) | Vol |
|---|---|---|---|
| Rinse | 4-400 mM PB, pH 6.3-6.7 | ≤25-2500 | ≥1-5 |
| Pre-use Sanitization | 0.01-1.0M NaOH | ≤25-2500 | ≥1-3 (10-30 min) |
| Equilibration | 4-400 mM PB, pH 6.5 | ≤25-2500 | ≥1-5 |
| Wash with WFI | Water For Injection (WFI) | ≤25-2500 | ≥1-3 |
| Chelating | 0.01-1.0 M Copper Acetate | ≤25-2500 | ≥1-5 |
| Wash with WFI | WFI | ≤25-2500 | ≥2-10 |
| Wash with acidic buffer | 2-200 mM Sodium Acetate, 0.05-5M NaCl, pH 3.5-4.5 | ≤25-2500 | ≥2-10 |
| Equilibration | 4-400 mM PB, pH 6.3-6.7 | ≤25-2500 | ≥1-5 |
| Blank run with elution buffer | 4-400 mM PB, 15-1500 mM Glycine, pH 6.1-6.5 | ≤25-2500 | ≥2-20 |
| Equilibration | 4-400 mM PB, pH 6.3-6.7 | ≤25-2500 | ≥1-5 |
| Load | NA | ≤25-2500 | ≥1-5 |
| Wash1 | 4-400 mM PB, pH 6.3-6.7 | ≤25-2500 | ≥2-10 |
| Wash2 | 4-400 mM PB, 0.1-10M NaCl, 5-30% propylene glycol, pH 6.3-6.7 | ≤25-2500 | ≥2-10 |
| Wash3 | 4-400 mM PB, pH 6.3-6.7 | ≤25-2500 | ≥2-10 |
| Elution | 4-400 mM PB, 15-1500 mM Glycine, pH 6.1-6.5 | ≤25-2500 | NA |
| Strip | 4-400 mM PB, 50-5000 mM imidazole, pH 6.3-6.7 | ≤25-2500 | ≥1-5 |
| Post-use Sanitization | 0.01-1M NaOH | ≤25-2500 | ≥1-3 (10-30 min) |
| Rinse | 4-400 mM PB, pH 6.3-6.7 | ≤25-2500 | ≥1-5 |
| Storage | 5-30% ethanol | ≤25-2500 | ≥1-5 |

After the rhGAA is loaded onto the second chromatography system 609, the recombinant protein is eluted from the column(s). The eluted rhGAA can be subjected to a virus kill step 611. As with vims kill 607, vims kill 611 may include one or more of a low pH kill, a detergent kill, or other technique known in the art. In some embodiments, only one of vims kill 607 or 611 is used, or the vims kills are performed at the same stage in the purification process.

The rhGAA from the vims kill step 611 may be introduced into a third chromatography system 613 to further purify the recombinant protein product. Alternatively, the eluted recombinant protein from the second chromatography system 609 may be fed directly to the third chromatography system 613. In various embodiments, the third chromatography system 613 includes one or more cation exchange chromatography (CEX) columns and/or size exclusion chromatography (SEC) columns for further removal of impurities. The rhGAA product is then eluted from the third chromatography system 613. Exemplary conditions for a CEX column are provided in Table 4 below.

The rhGAA product may also be subjected to further processing. For example, another filtration system 615 may be used to remove viruses. In some embodiments, such filtration can utilize filters with pore sizes between 5 and 50 μm. Other product processing can include a product adjustment step 617, in which the recombinant protein product may be sterilized, filtered, concentrated, stored, and/or have additional components for added for the final product formulation.

As used herein, the term "ATB200" refers to a rhGAA with a high content of N-glycans bearing mono-M6P and bis-M6P, which is produced from a GA-ATB200 cell line and purified using methods described herein.

V. Pharmaceutical Composition

In various embodiments, a pharmaceutical composition comprising the rhGAA described herein, either alone or in combination with other therapeutic agents, and/or a pharmaceutically acceptable carrier, is provided.

TABLE 4

Exemplary conditions for a CEX column

| Procedure | Buffer | Flow rate (cm/h) | Vol (CV) |
|---|---|---|---|
| Pre-used Sanitization | 0.1-10M NaOH | ≤25-2500 | ≥1-3 (≥10-120 min) |
| Equilibration | 2-200 mM Sodium citrate, pH 4.0-5.0 | ≤30-3000 | ≥2-10 |
| Load | NA | ≤30-3000 | NA |
| Wash | 2-200 mM Sodium citrate, pH 4.0-5.0 | ≤30-3000 | ≥2-10 |
| Elution | 2-200 mM Sodium citrate, 15-1500 mM NaCl, pH 4.0-5.0 | ≤30-3000 | ≥2-10 |
| Strip | 2-200 mM Sodium citrate, 0.1-10M NaCl, pH 4.0-5.0 | ≤25-2500 | ≥1-5 |
| Post-use Sanitization | 0.1-10M NaOH | ≤25-2500 | ≥1-3 (≥10-120 min) |
| Storage | 0.01-1.0M NaOH | ≤30-3000 | ≥1-5 |

In one or more embodiments, a pharmaceutical composition described herein comprises a pharmaceutically acceptable salt.

In some embodiments, the pharmaceutically acceptable salt used herein is a pharmaceutically-acceptable acid addition salt. The pharmaceutically-acceptable acid addition salt may include, but is not limited to, hydrochloric acid, hydrobromic acid, sulfuric acid, sulfamic acid, nitric acid, phosphoric acid, and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

In some embodiments, the pharmaceutically acceptable salt used herein is a pharmaceutically-acceptable base addition salt. The pharmaceutically-acceptable base addition salt may include, but is not limited to, ammonia or the hydroxide, carbonate, or bicarbonate of ammonium or a metal cation such as sodium, potassium, lithium, calcium, magnesium, iron, zinc, copper, manganese, aluminum, and the like. Salts derived from pharmaceutically-acceptable organic nontoxic bases include, but are not limited to, salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine. N-methylmorpholine, dicyclohexylamine, dibenzylamine, N,N-dibenzylphenethylamine, 1-ephenamine, N,N'-dibenzylethylenediamine, polyamine resins, and the like.

In some embodiments, the rhGAA or a pharmaceutically acceptable salt thereof may be formulated as a pharmaceutical composition adapted for intravenous administration. In some embodiments, the pharmaceutical composition is a solution in sterile isotonic aqueous buffer. Where necessary, the composition may also include a solubilizing agent and a local anesthetic to ease pain at the site of the injection. The ingredients of the pharmaceutical composition may be supplied either separately or mixed together in unit dosage form, for example, as a dry lyophilized powder or water free concentrate in a hermetically sealed container such as an ampule or sachet indicating the quantity of active agent. Where the composition is to be administered by infusion, it may be dispensed with an infusion bottle containing sterile pharmaceutical grade water, saline or dextrose/water. In some embodiments, the infusion may occur at a hospital or clinic. In some embodiments, the infusion may occur outside the hospital or clinic setting, for example, at a subject's residence. Where the composition is administered by injection, an ampule of sterile water for injection or saline may be provided so that the ingredients may be mixed prior to administration.

In some embodiments, the rhGAA or a pharmaceutically acceptable salt thereof may be formulated for oral administration. Orally administrate compositions may be formulated in a form of tablets, capsules, ovules, elixirs, solutions or suspensions, gels, syrups, mouth washes, or a dry powder for reconstitution with water or other suitable vehicle before use, optionally with flavoring and coloring agents for immediate-, delayed-, modified-, sustained-, pulsed-, or controlled-release applications. Solid compositions such as tablets, capsules, lozenges, pastilles, pills, boluses, powder, pastes, granules, bullets, dragees, or premix preparations can also be used. Solid and liquid compositions for oral use may be prepared according to methods well known in the art. Such compositions can also contain one or more pharmaceutically acceptable carriers and excipients which can be in solid or liquid form. Tablets or capsules can be prepared by conventional means with pharmaceutically acceptable excipients, including but not limited to binding agents, fillers, lubricants, disintegrants, or wetting agents. Suitable pharmaceutically acceptable excipients are known in the art and include but are not limited to pregelatinized starch, polyvinylpyrrolidone, povidone, hydroxypropyl methylcellulose (HPMC), hydroxypropyl ethylcellulose (HPEC), hydroxypropyl cellulose (HPC), sucrose, gelatin, acacia, lactose, microcrystalline cellulose, calcium hydrogen phosphate, magnesium stearate, stearic acid, glyceryl behenate, talc, silica, corn, potato or tapioca starch, sodium starch glycolate, sodium lauryl sulfate, sodium citrate, calcium carbonate, dibasic calcium phosphate, glycine croscarmellose sodium, and complex silicates. Tablets can be coated by methods well known in the art.

In some embodiments, a pharmaceutical composition described herein may be formulated according to International Application PCT/US2017/024982 and U.S. Provisional Application No. 62/506,574, both incorporated herein by reference in their entirety. For instance, in some embodiments, the pH of a pharmaceutical composition described herein is from about 5.0 to about 7.0 or about 5.0 to about 6.0. In some embodiments, the pH ranges from about 5.5 to about 6.0. In some embodiments, the pH of the pharmaceutical composition is 6.0. In some embodiments, the pH may be adjusted to a target pH by using pH adjusters (e.g., alkalizing agents and acidifying agents) such as sodium hydroxide and/or hydrochloric acid.

The pharmaceutical composition described herein may comprise a buffer system such as a citrate system, a phosphate system, and a combination thereof. The citrate and/or phosphate may be a sodium citrate or sodium phosphate. Other salts include potassium and ammonium salts. In one or more embodiments, the buffer comprises a citrate. In further embodiments, the buffer comprises sodium citrate (e.g., a mixture of sodium citrate dehydrate and citric acid monohydrate). In one or more embodiments, buffer solutions comprising a citrate may comprise sodium citrate and citric acid. In some embodiments, both a citrate and phosphate buffer are present.

In some embodiments, a pharmaceutical composition described herein comprises at least one excipient. The excipient may function as a tonicity agent, bulking agent, and/or stabilizer. Tonicity agents are components which help to ensure the formulation has an osmotic pressure similar to or the same as human blood. Bulking agents are ingredients which add mass to the formulations (e.g. lyophilized) and provide an adequate structure to the cake. Stabilizers are compounds that can prevent or minimize the aggregate formation at the hydrophobic air-water interfacial surfaces. One excipient may function as a tonicity agent and bulking agent at the same time. For instance, mannitol may function as a tonicity agent and also provide benefits as a bulking agent.

Examples of tonicity agents include sodium chloride, mannitol, sucrose, and trehalose. In some embodiments, the tonicity agent comprises mannitol. In some embodiments, the total amount of tonicity agent(s) ranges in an amount of from about 10 mg/mL to about 50 mg/mL. In further embodiments, the total amount of tonicity agent(s) ranges in an amount of from about 10, 11, 12, 13, 14, or 15 mg/mL to about 16, 20, 25, 30, 35, 40, 45, or 50 mg/mL.

In some embodiments, the excipient comprises a stabilizer. In some embodiments, the stabilizer is a surfactant. In some embodiments, the stabilizer is polysorbate 80. In one or mote embodiments, the total amount of stabilizer ranges from about 0.1 mg/mL to about 1.0 mg/mL. In further embodiments, the total amount of stabilizer ranges from about 0.1, 0.2, 0.3, 0.4, or 0.5 mg/mL to about 0.5, 0.6, 0.7, 0.8, 0.9, or 1.0 mg/mL. In yet further embodiments, the total amount of stabilizer is about 0.1, 0.2, 0.3, 0.4, 0.5, 0.6, 0.7, 0.8, 0.9, or 1.0 mg/mL.

In some embodiments, a pharmaceutical composition comprises (a) a rhGAA (such as ATB200), (b) at least one buffer selected from the group consisting of a citrate, a phosphate, and a combination thereof, and (c) at least one excipient selected from the group consisting of mannitol, polysorbate 80, and a combination thereof, and has a pH of (i) from about 5.0 to about 6.0, or (ii) from about 5.0 to about 7.0. In some embodiments, the composition further comprises water. In some embodiments, the composition may further comprise an acidifying agent and/or alkalizing agent.

In some embodiments, the pharmaceutical composition comprises (a) a rhGAA (such as ATB200) at a concentration of about 5-50 mg/mL, about 5-30 mg/mL, or about 15 mg/mL, (b) sodium citrate buffer at a concentration of about 10-100 mM or about 25 mM, (c) mannitol at a concentration of about 10-50 mg/mL, or about 20 mg/mL, (d) polysorbate 80, present at a concentration of about 0.1-1 mg/mL, about 0.2-0.5 mg/mL, or about 0.5 mg/mL, and (e) water, and has a pH of about 6.0. In at least one embodiment, the pharmaceutical composition comprises (a) 15 mg/mL rhGAA (such as ATB200) (b) 25 mM sodium citrate buffer, (c) 20 mg/mL mannitol (d) 0.5 mg/mL polysorbate 80, and (e) water, and has a pH of about 6.0. In some embodiments, the composition may further comprise an acidifying agent and/or alkalizing agent.

In some embodiments, the pharmaceutical composition comprising rhGAA is diluted prior to administration to a subject in need thereof.

In some embodiments, a pharmaceutical composition described herein comprises a chaperone. In some embodiments, the chaperone is miglustat or a pharmaceutically acceptable salt thereof. In another embodiment, the chaperone is duvoglustat or a pharmaceutically acceptable salt thereof.

In some embodiments, a rhGAA described herein is formulated in one pharmaceutical composition while a chaperone such as miglustat is formulated in another pharmaceutical composition. In some embodiments, the pharmaceutical composition comprising miglustat is based on a formulation available commercially as Zavesca® (Actelion Pharmaceuticals).

In some embodiments, the pharmaceutical composition described herein may undergo lyophilization (freeze-drying) process to provide a cake or powder. Accordingly, another aspect of the invention pertains to a pharmaceutical composition after lyophilization. The lyophilized mixture may comprise the rhGAA described herein (e.g., ATB200), buffer selected from the group consisting of a citrate, a phosphate, and combinations thereof, and at least one excipient selected from the group consisting of trehalose, mannitol, polysorbate 80, and a combination thereof. In some embodiments, other ingredients (e.g., other excipients) may be added to the lyophilized mixture. The pharmaceutical composition comprising the lyophilized formulation may be provided vial, which then can be stored, transported, reconstituted and/or administered to a patient.

VI. Methods of Treatment

A. Treatment of Diseases

Another aspect of the invention pertains to a method of treatment of a disease or disorder related to glycogen storage dysregulation by administering the rhGAA or pharmaceutical composition described herein. In some embodiments, the disease is Pompe disease (also known as acid maltase deficiency (AMD) and glycogen storage disease type II (GSDII)). In some embodiments, the rhGAA is ATB200. In some embodiments, the pharmaceutical composition comprises ATB200.

The rhGAA or pharmaceutical composition described herein is administered by an appropriate route. In one embodiment, the rhGAA or pharmaceutical composition is administered intravenously. In other embodiments, the rhGAA or pharmaceutical composition is administered by direct administration to a target tissue, such as to heart or skeletal muscle (e.g., intramuscular), or nervous system (e.g., direct injection into the brain; intraventricularly; intrathecally). In some embodiments, the rhGAA or pharmaceutical composition is administered orally. More than one route can be used concurrently, if desired.

In some embodiments, the therapeutic effects of the rhGAA or pharmaceutical composition described herein may be assessed based on one or more of the following criteria: (1) cardiac status (e.g., increase of end-diastolic and/or end-systolic volumes, or reduction, amelioration or prevention of the progressive cardiomyopathy that is typically found in GSD-II), (2) pulmonary function (e.g., increase in crying vital capacity over baseline capacity, and/or normalization of oxygen desaturation during crying), (3) neurodevelopment and/or motor skills (e.g., increase in AIMS score), and (4) reduction of glycogen levels in tissue of the individual affected by the disease.

In some embodiments, the cardiac status of a subject is improved by 10%, 20%, 30%, 40%, or 50% (or any percentage in-between) after administration of one or more dosages of the rhGAA or pharmaceutical composition described herein, as compared to that of a subject treated with a vehicle or that of a subject prior to treatment. The cardiac status of a subject may be assessed by measuring end-diastolic and/or end-systolic volumes and/or by clinically evaluating cardiomyopathy. In some embodiments, the pulmonary function of a subject is improved by 10%, 20%, 30%, 40%, or 50% (or any percentage in-between) after administration of one or more dosages of ATB200 or pharmaceutical composition comprising ATB200, as compared to that of a subject treated with a vehicle or that of a subject prior to treatment. In certain embodiments, the improvement is achieved after 1 week, 2 weeks, 3 weeks, 1 month, 2 months, or more from administration (or any time period in between). In certain embodiments, ATB200 or pharmaceutical composition comprising ATB200 improves the pulmonary function of a subject after 1 week, 2 weeks, 3 weeks, 1 month, 2 months, or more from administration (or any time period in between).

In some embodiments, the pulmonary function of a subject is improved by 10%, 20%, 30%, 40%, or 50% (or any percentage in-between) after administration of one or more dosages of the rhGAA or pharmaceutical composition described herein, as compared to that of a subject treated with a vehicle or that of a subject prior to treatment. The pulmonary function of a subject may be assessed by crying vital capacity over baseline capacity, and/or normalization of oxygen desaturation during crying. In some embodiments, the pulmonary function of a subject is improved by 10%, 20%, 30%, 40%, or 50% (or any percentage in-between) after administration of one or more dosages of ATB200 or pharmaceutical composition comprising ATB200, as compared to that of a subject treated with a vehicle or that of a subject prior to treatment. In certain embodiments, the improvement is achieved after 1 week, 2 weeks, 3 weeks, 1 month, 2 months, or more from administration (or any time period in between). In certain embodiments, ATB200 or pharmaceutical composition comprising ATB200 improves the pulmonary function of a subject after 1 week, 2 weeks, 3 weeks, 1 month, 2 months, or more from administration (or any time period in between).

In some embodiments, the neurodevelopment and/or motor skills of a subject is improved by 10%, 20%, 30%, 40%, or 50% (or any percentage in-between) after administration of one or more dosages of the rhGAA or pharmaceutical composition described herein, as compared to that of a subject treated with a vehicle or that of a subject prior to treatment. The neurodevelopment and/or motor skills of a subject may be assessed by determining an AIMS score. The AIMS is a 12-item anchored scale that is clinician-administered and scored (see Rush J A Jr., Handbook of Psychiatric Measures, American Psychiatric Association, 2000, 166-168). Items 1-10 are rated on a 5-point anchored scale. Items 1-4 assess orofacial movements. Items 5-7 deal with extremity and truncal dyskinesia. Items 8-10 deal with global severity as judged by the examiner, and the patient's awareness of the movements and the distress associated with them. Items 11-12 are yes/no questions concerning problems with teeth and/or dentures (such problems can lead to a mistaken diagnosis of dyskinesia). In some embodiments, the neurodevelopment and/or motor skills of a subject is improved by 10%, 20%, 30%, 40%, or 50% (or any percentage in-between) after administration of one or more dosages of ATB200 or pharmaceutical composition comprising ATB200, as compared to that of a subject treated with a vehicle or that of a subject prior to treatment. In certain embodiments, the improvement is achieved after 1 week, 2 weeks, 3 weeks, 1 month, 2 months, or more from administration (or any time period in between). In certain embodiments, ATB200 or pharmaceutical composition comprising ATB200 improves the neurodevelopment and/or motor skills of a subject after 1 week, 2 weeks, 3 weeks, 1 month, 2 months, or more from administration (or any time period in between).

In some embodiments, the glycogen level of a certain tissue of a subject is reduced by 10%, 20%, 30%, 40%, or 50% (or any percentage in-between) after administration of one or more dosages of the rhGAA or pharmaceutical composition described herein, as compared to that of a subject treated with a vehicle or that of a subject prior to treatment. In some embodiment, the tissue is muscle such as quadriceps, triceps, and gastrocnemius. The glycogen level of a tissue can be analyzed using methods known in the art. The determination of glycogen levels is well known based on amyloglucosidase digestion, and is described in publications such as: Amalfitano et al. (1999), "Systemic correction of the muscle disorder glycogen storage disease type ii after hepatic targeting of a modified adenovirus vector encoding human acid-alphaglucosidase," Proc Natl Acad Sci USA, 96:8861-8866. In some embodiments, the glycogen level in muscle of a subject is reduced by 10%, 20%, 30%, 40%, or 50% (or any percentage in between) after administration of one or more dosages of ATB200 or pharmaceutical composition comprising ATB200, as compared to that of a subject treated with a vehicle or that of a subject prior to treatment. In certain embodiments, the reduction is achieved after 1 week, 2 weeks, 3 weeks, 1 month, 2 months, or more from administration (or any-time period in between). In certain embodiments, ATB200 or pharmaceutical composition comprising ATB200 reduces the glycogen level in muscle of a subject after 1 week, 2 weeks, 3 weeks, 1 month, 2 months, or more from administration (or any time period in between).

B. Biomarkers

Biomarkers of glycogen accumulation in a muscle fiber in a subject, such as urine hexose tetrasaccharide (Hex4), may be used to assess and compare the therapeutic effects of enzyme replacement therapy in a subject with Pompe disease. In some embodiments, the therapeutic effect of the rhGAA or a pharmaceutical composition comprising rhGAA on glycogen accumulation is assessed by measuring the levels of Hex4 in a subject.

Biomarkers of muscle injury or damage such as creatine kinase (CK), alanine aminotransferase (ALT), and aspartate aminotransferase (AST) may be used to assess and compare the therapeutic effects of enzyme replacement therapy in a subject with Pompe disease. In some embodiments, the therapeutic effect of the rhGAA or a pharmaceutical composition comprising rhGAA on muscle damage is assessed by measuring the levels of CK, ALT, and/or AST in a subject. In at least one embodiment, the therapeutic effect of the rhGAA or a pharmaceutical composition comprising rhGAA on muscle damage is assessed by measuring the levels of CK in a subject.

Biomarkers such as LAMP-1, LC3, and Dysferlin may also be used to assess and compare the therapeutic effects of the rhGAA or pharmaceutical composition described herein. In Pompe disease, the failure of GAA to hydrolyze lysosomal glycogen leads to the abnormal accumulation of large lysosomes filled with glycogen in some tissues. (Raben et al., JBC 273: 19086-19092, 1998.) Studies in a mouse model of Pompe disease have shown that the enlarged lysosomes in skeletal muscle cannot adequately account for the reduction in mechanical performance, and that the presence of large inclusions containing degraded myofibrils (i.e., autophagic buildup) contributes to the impairment of muscle function. (Raben et al., Human Mol Genet 17: 3897-3908, 2008.) Reports also suggest that impaired autophagy flux is associated with poor therapeutic outcome in Pompe patients. (Nascimbeni et al., Neuropathology and Applied Neurobiology doi: 10.1111/nan.12214, 2015; Fukuda et al., Mol Ther 14: 831-839, 2006.) In addition, late-onset Pompe disease is prevalent in unclassified limb-girdle muscular dystrophies (LGMDs) (Preisler et al., Mol Genet Metab 110. 287-289, 2013), which is a group of genetically heterogeneous neuromuscular diseases with more than 30 genetically defined subtypes of varying severity. IHC examination revealed substantially elevated sarcoplasmic presence of dysferlin in the skeletal muscle fibers of Gaa KO mice.

Various known methods can be used to measure the gene expression level and/or protein level of such biomarkers. For instance, a sample from a subject treated with the rhGAA or pharmaceutical composition described herein can be obtained, such as biopsy of tissues, in particular muscle. In some embodiments, the sample is a biopsy of muscle in a subject. In some embodiments, the muscle is selected from quadriceps, triceps, and gastrocnemius. The sample obtained from a subject may be stained with one or more antibodies or other detection agents that detect such biomarkers or be identified and quantified by mass spectrometry. The samples may also or alternatively be processed for detecting the presence of nucleic acids, such as mRNAs, encoding the biomarkers via, e.g., RT-qPCR methods.

In some embodiments, the gene expression level and/or protein level of one or more biomarkers is measured in a muscle biopsy obtained from an individual prior to and post treatment with the rhGAA or pharmaceutical composition described herein. In some embodiments, the gene expression level and/or protein level of one or more biomarkers is measured in a muscle biopsy obtained from an individual treated with a vehicle. In some embodiments, the gene expression level and/or protein level of one or more biomarkers is reduced by 10%, 20%, 30%, 40%, or 50% (or any percentage in-between) after administration of one or more dosages of the rhGAA or pharmaceutical composition described herein, as compared to that of a subject treated with a vehicle or that of a subject prior to treatment. In some embodiments, the gene expression level and/or protein level of one or more biomarkers is reduced by 10%, 20%, 30%, 40%, or 50% (or any percentage in-between) after administration of one or more dosages of ATB200 or pharmaceutical composition comprising ATB200, as compared to that of a subject treated with a vehicle or that of a subject prior to treatment. In certain embodiments, the reduction is achieved after 1 week, 2 weeks, 3 weeks, 1 month, 2 months, or more from administration (or any time period in between). In certain embodiments, ATB200 or pharmaceutical composition comprising ATB200 reduces the gene expression level and/or protein level of one or more biomarkers after 1 week, 2 weeks, 3 weeks, 1 month, 2 months, or more from administration (or any time period in between).

C. Dosages of rhGAA

The pharmaceutical formulation or reconstituted composition is administered in a therapeutically effective amount (e.g., a dosage amount that, when administered at regular intervals, is sufficient to treat the disease, such as by ameliorating symptoms associated with the disease, preventing or delaying the onset of the disease, and/or lessening the severity or frequency of symptoms of the disease). The amount which is therapeutically effective in the treatment of the disease may depend on the nature and extent of the disease's effects, and can be determined by standard clinical techniques. In addition, in vitro or in vivo assays may optionally be employed to help identify optimal dosage ranges. In at least one embodiment, a rhGAA described herein or pharmaceutical composition comprising the rhGAA is administered at a dose of about 1 mg/kg to about 100 mg/kg, such as about 5 mg/kg to about 30 mg/kg, typically about 5 mg/kg to about 20 mg/kg. In at least one embodiment, the rhGAA or pharmaceutical composition described herein is administered at a dose of about 5 mg/kg, about 10 mg/kg, about 15 mg/kg, about 20 mg/kg, about 25 mg/kg, about 30 mg/kg, about 35 mg/kg, about 40 mg/kg, about 50 mg/kg, about 50 mg/kg, about 60 mg/kg, about 70 mg/kg, about 80 mg/kg, about 90 mg/kg, or about 100 mg/kg. In some embodiments, the rhGAA is administered at a dose of 5 mg/kg, 10 mg/kg, 20 mg/kg, 50 mg/kg, 75 mg/kg, or 100 mg/kg. In at least one embodiment, the rhGAA or pharmaceutical composition is administered at a dose of about 20 mg/kg. In some embodiments, the rhGAA or pharmaceutical composition is administered concurrently or sequentially with a pharmacological chaperone. In some embodiments, the pharmacological chaperone is miglustat. In at least one embodiment, the miglustat is administered as an oral dose of about 260 mg. The effective dose for a particular individual can be varied (e.g. increased or decreased) over time, depending on the needs of the individual. For example, in times of physical illness or stress, or if anti-acid α-glucosidase antibodies become present or increase, or if disease symptoms worsen, the amount can be increased.

In some embodiments, the therapeutically effective dose of the rhGAA or pharmaceutical composition described herein is lower than that of conventional rhGAA products. For instance, if the therapeutically effective dose of a conventional rhGAA product is 20 mg/kg, the dose of the rhGAA or pharmaceutical composition described herein required to produce the same as or better therapeutic effects than the conventional rhGAA product may be lower than 20 mg/kg. Therapeutic effects may be assessed based on one or more criteria discussed above (e.g., cardiac status, glycogen level, or biomarker expression). In some embodiments, the therapeutically effective dose of the rhGAA or pharmaceutical composition described herein is at least about 5%, 10%, 15%, 20%, 30%, 40%, 50%, 60%, 70%, 80%, 90%, or more lower than that of conventional rhGAA products.

In some embodiments, the therapeutic effect of the rhGAA or pharmaceutical composition described herein comprises an improvement in motor function, an improvement in muscle strength (upper-body, lower-body, or total-body), an improvement in pulmonary function, decreased fatigue, reduced levels of at least one biomarker of muscle injury, reduced levels of at least one biomarker of glycogen accumulation, or a combination thereof. In some embodiments, the therapeutic effect of the rhGAA or pharmaceutical composition described herein comprises a reversal of lysosomal pathology in a muscle fiber, a faster and/or mote effective reduction in glycogen content in a muscle fiber, an increase in six-minute walk test distance, a decrease in timed up and go test time, a decrease in four-stair climb test time, a decrease in ten-meter walk test time, a decrease in gait-stair-gower-chair score, an increase in upper extremity strength, an improvement in shoulder adduction, an improvement in shoulder abduction, an improvement in elbow flexion, an improvement in elbow extension, an improvement in upper body strength, an improvement in lower body strength, an improvement in total body strength, an improvement in upright (sitting) forced vital capacity, an improvement in maximum expiratory pressure, an improvement in maximum inspiratory pressure, a decrease in fatigue severity scale score, a reduction in urine hexose tetrasaccharide levels, a reduction in creatine kinase levels, a reduction in alanine aminotransferase levels, a reduction in asparate aminotransferase levels, or any combination thereof.

In some embodiments, the rhGAA or pharmaceutical composition described herein achieves desired therapeutic effects faster than conventional rhGAA products when administered at the same dose. Therapeutic effects may be assessed based on one or more criteria discussed above (e.g., cardiac status, glycogen level, or biomarker expression). For instance, if a single dose of a conventional rhGAA product decreases glycogen levels in tissue of a treated individual by 10% in a week, the same degree of reduction may be achieved in less than a week when the same dose of the rhGAA or pharmaceutical composition described herein is administered. In some embodiments, when administered at the same dose, the rhGAA or pharmaceutical composition described herein may achieves desired therapeutic effects at least about 1.25, 1.5, 1.75, 2.0, 3.0, or more faster than conventional rhGAA products.

In some embodiments, the therapeutically effective amount of rhGAA (or composition or medicament comprising rhGAA) is administered more than once. In some embodiments, the rhGAA or pharmaceutical composition described herein is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In certain embodiments, rhGAA is administered bimonthly, monthly, bi-weekly, weekly, twice weekly, or daily. In some embodiments, the rhGAA is administered intravenously twice weekly, weekly, or every other week. The administration interval for a single individual need not be a fixed interval, but can be varied over time, depending on the needs of the individual. For example, in times of physical illness or stress, if anti-rhGAA antibodies become present or increase, or if disease symptoms worsen, the interval between doses can be decreased.

In some embodiments, when used at the same dose, the rhGAA or pharmaceutical composition as described herein may be administered less frequently than conventional rhGAA products and yet capable of producing the same as or better therapeutic effects than conventional rhGAA products. For instance, if a conventional rhGAA product is administered at 20 mg/kg weekly, the rhGAA or pharmaceutical composition as described herein may produce the same as or better therapeutic effects than the conventional rhGAA product when administered at 20 mg/kg, even though the rhGAA or pharmaceutical composition is administered less frequently, e.g., biweekly or monthly. Therapeutic effects may be assessed based on one or more criterion discussed above (e.g., cardiac status, glycogen level, or biomarker expression). In some embodiments, an interval between two doses of the rhGAA or pharmaceutical composition described herein is longer than that of conventional rhGAA products. In some embodiments, the interval between two doses of the rhGAA or pharmaceutical composition is at least about 1.25, 1.5, 1.75, 2.0, 3.0, or more longer than that of conventional rhGAA products.

In some embodiments, under the same treatment condition (e.g., the same dose administered at the same interval), the rhGAA or pharmaceutical composition described herein provides therapeutic effects at a degree superior than that provided by conventional rhGAA products. Therapeutic effects may be assessed based on one or more criteria discussed above (e.g., cardiac status, glycogen level, or biomarker expression). For instance, when compared to a conventional rhGAA product administered at 20 mg/kg weekly, the rhGAA or pharmaceutical composition administered at 20 mg/kg weekly may reduce glycogen levels in tissue of a treated individual at a higher degree. In some embodiments, when administered under the same treatment condition, the rhGAA or pharmaceutical composition described herein provides therapeutic effects that are at least about 1.25, 1.5, 1.75, 2.0, 3.0, or more greater than those of conventional rhGAA products.

D. Combination Therapy

In one or more embodiments, the rhGAA or pharmaceutical composition comprising the rhGAA described herein is administered concurrently or sequentially with a pharmacological chaperone. In some embodiments, the rhGAA or pharmaceutical composition is administered via a different route as compared to the pharmacological chaperone. For instance, a pharmacological chaperone may be administered orally while the rhGAA or pharmaceutical composition is administered intravenously.

In various embodiments, the pharmacological chaperone is miglustat. In some embodiments, the miglustat is administered at an oral dose of about 50 mg to about 600 mg. In at least one embodiment, the miglustat is administered at an oral dose of about 200 mg to about 600 mg, or at an oral dose of about 200 mg, about 250 mg, about 300 mg, about 350 mg, about 400 mg, about 450 mg, about 500 mg, about 550 mg, or about 600 mg. In at least one embodiment, the miglustat is administered at an oral dose of about 233 mg to about 500 mg. In at least one embodiment, the miglustat is administered at an oral dose of about 250 to about 270 mg, or at an oral dose of about 250 mg, about 255 mg, about 260 mg, about 265 mg or about 270 mg. In at least one embodiment, the miglustat is administered as an oral dose of about 260 mg.

It will be understood by those skilled in the art that an oral dose of miglustat in the range of about 200 mg to 600 mg or any smaller range therewith can be suitable for an adult patient depending on his/her body weight. For instance, for patients having a significantly lower body weight than about 70 kg, including but not limited to infants, children, or underweight adults, a smaller dose may be considered suitable by a physician. Therefore, in at least one embodiment, the miglustat is administered as an oral dose of from about 50 mg to about 200 mg, or as an oral dose of about 50 mg, about 75 mg, about 100 mg, 125 mg, about 150 mg, about 175 mg, or about 200 mg. In at least one embodiment, the miglustat is administered as an oral dose of from about 65 mg to about 195 mg, or as an oral dose of about 65 mg, about 130 mg, or about 195 mg.

In some embodiments, the rhGAA is administered intravenously at a dose of about 5 mg/kg to about 20 mg/kg and the miglustat is administered orally at a dose of about 50 mg to about 600 mg. In some embodiments, the rhGAA is administered intravenously at a dose of about 5 mg/kg to about 20 mg/kg and the miglustat is administered orally at a dose of about 50 mg to about 200 mg. In some embodiments, the rhGAA is administered intravenously at a dose of about 5 mg/kg to about 20 mg/kg and the miglustat is administered orally at a dose of about 200 mg to about 600 mg. In some embodiments, the rhGAA is administered intravenously at a dose of about 5 mg/kg to about 20 mg/kg and the miglustat is administered orally at a dose of about 233 mg to about 500 mg. In one embodiment, the rhGAA is administered intravenously at a dose of about 20 mg/kg and the miglustat is administered orally at a dose of about 260 mg.

In some embodiments, the miglustat and the rhGAA are administered concurrently. For instance, the miglustat may administered within 10, 9, 8, 7, 6, 5, 4, 3, 2, or 1 minute(s) before or after administration of the rhGAA. In some embodiments, the miglustat is administered within 5, 4, 3, 2, or 1 minute(s) before or after administration of the rhGAA.

In some embodiments, the miglustat and the rhGAA are administered sequentially. In at least one embodiment, the miglustat is administered prior to administration of the rhGAA. In at least one embodiment, the miglustat is administered less than three hours prior to administration of the rhGAA. In at least one embodiment, the miglustat is administered about two hours prior to administration of the rhGAA. For instance, the miglustat may be administered about 1.5 hours, about 1 hour, about 50 minutes, about 30 minutes, or about 20 minutes prior to administration of the rhGAA. In at least one embodiment, the miglustat is administered about one hour prior to administration of the rhGAA.

In some embodiments, the miglustat is administered after administration of the rhGAA. In at least one embodiment, the miglustat is administered within three hours after administration of the rhGAA. In at least one embodiment, the miglustat is administered within two hours after administration of the rhGAA. For instance, the miglustat may be administered within about 1.5 hours, about 1 hour, about 50 minutes, about 30 minutes, or about 20 minutes after administration of the rhGAA.

In some embodiments, the subject fasts for at least two hours before and at least two hours after administration of miglustat.

E. Kit

Another aspect of the invention pertains to kits comprising the rhGAA or pharmaceutical composition described herein. In one or more embodiments, the kit comprises a container (e.g., vial, tube, bag, etc.) comprising the rhGAA or pharmaceutical composition (either before or after lyophilization) and instructions for reconstitution, dilution and administration.

EXAMPLES

Figure 4:
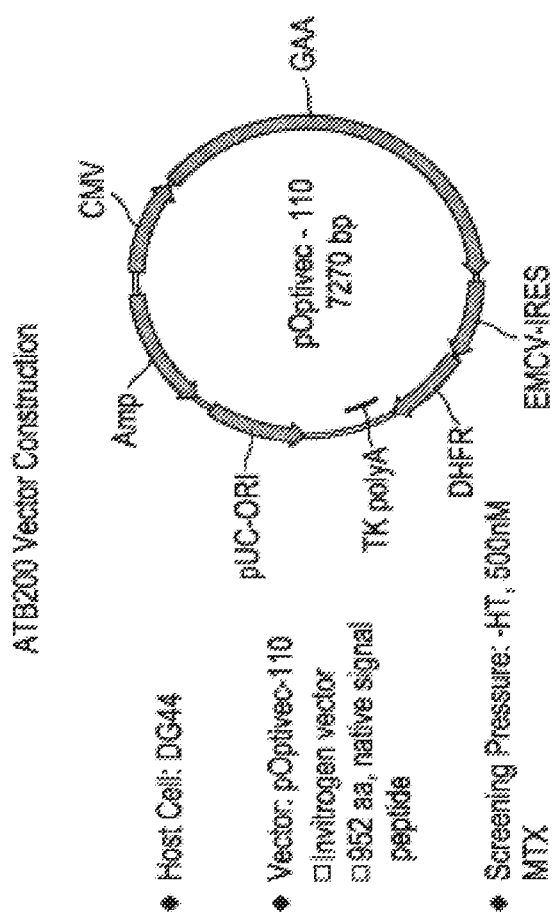
FIG. 4 shows a DNA construct for transforming CHO cells with DNA encoding rhGAA.

Example 1: Preparation of CHO Cells Producing rhGAA Having a High Content of Mono- or Bis-M6P-Bearing N-Glycans DG44 CHO (DHFR−) cells were transfected with a DNA construct that expresses rhGAA. The DNA construct is shown in FIG. 4. After transfection, CHO cells containing a stably integrated GAA gene were selected with hypoxanthine/thymidine deficient (-HT) medium). GAA expression in these cells was induced by methotrexate treatment (MTX, 500 nM).

Cell pools that expressed high amounts of GAA were identified by GAA enzyme activity assays and were used to establish individual clones producing rhGAA. Individual clones were generated on semisolid media plates, picked by ClonePix system, and were transferred to 24-deep well plates. The individual clones were assayed for GAA enzyme activity to identify clones expressing a high level of GAA. Conditioned media for determining GAA activity used a 4-MU-α-Glucosidase substrate. Clones producing higher levels of GAA as measured by GAA enzyme assays were further evaluated for viability, ability to grow, GAA productivity, N-glycan structure and stable protein expression. CHO cell lines, including CHO cell line GA-ATB200, expressing rhGAA with enhanced mono-M6P or bis-M6P N-glycans were isolated using this procedure.

Example 2: Purification of rhGAA

Multiple batches of the rhGAA according to the invention were produced in shake flasks and in perfusion bioreactors using CHO cell line GA-ATB200, the product of which is referred to as "ATB200." Weak anion exchange ("WAX") liquid chromatography was used to fractionate ATB200 rhGAA according to terminal phosphate and sialic acid. Elution profiles were generated by eluting the ERT with increasing amount of salt. The profiles were monitored by UV (A280 nm). Similar CIMPR receptor binding (at least ~70%) profiles were observed for purified ATB200 rhGAA from different production batches (FIG. 5), indicating drat ATB200 rhGAA can be consistently produced.

Example 3: Oligosaccharide Characterization of ATB200 rhGAA

ATB200 rhGAA was analyzed for site-specific N-glycan profiles using different LC-MS/MS analytical techniques. The results of the first two LC-MS/MS methods are shown in FIGS. 6A-6H. The results of a third LC-MS/MS method with 2-AA glycan mapping is shown in FIGS. 32A-32H, FIG. 33A-33B, and Table 5.

In the first LC-MS/MS analysis, the protein was denatured, reduced, alkylated, and digested prior to LC-MS/MS analysis. During protein denaturation and reduction, 200 μg of protein sample, 5 μL of 1 mol/L tris-HCl (final concentration 50 mM), 75 μL of 8 mol/L guanidine HCl (final concentration 6 M), 1 μL of 0.5 mol/L EDTA (final concentration 5 mM), 2 μL of 1 mol/L DTT (final concentration 20 mM), and Milli-Q® water were added to a 1.5 mL tube to provide a total volume of 100 μL. The sample was mixed and incubated at 56° C. for 30 minutes in a dry bath. During alkylation, the denatured and reduced protein sample was mixed with 5 μL of 1 mol/L iodoacetamide (IAM, final concentration 50 mM), then incubated at 10-30° C. in the dark for 30 minutes. After alkylation, 400 μL of precooled acetone was added to the sample and the mixture was frozen at −80° C. refrigeration for 4 hours. The sample was then centrifuged for 5 min at 13000 rpm at 4° C. and the supernatant was removed. 400 μL of precooled acetone was added to the pellets, which was then centrifuged for 5 min at 13000 rpm at 4° C. and the supernatant was removed. The sample was then air dried on ice in the dark to remove acetone residue. Forty microliters of 8M urea and 160 μL of 100 mM NH$_4$HCO$_3$ were added to the sample to dissolve the protein. During trypsin digestion, 50 μg of the protein was then added with trypsin digestion buffer to a final volume of 100 μL, and 5 μL of 0.5 mg/mL trypsin (protein to enzyme ratio of 20/1 w/w) was added. The solution was mixed well and incubated overnight (16±2 hours) at 37° C. Two and a half microliters of 20% TFA (final concentration 0.5%) were added to quench the reaction. The sample was then analyzed using the Thermo Scientific™ Orbitrap Velos Pro™ Mass Spectrometer.

In the second LC-MS/MS analysis, the ATB200 sample was prepared according to a similar denaturation, reduction, alkylation, and digestion procedure, except that iodoacetic acid (IAA) was used as the alkylation reagent instead of LAM, and then analyzed using the Thermo Scientific™ Orbitrap Fusion™ Lumos Tribid™ Mass Spectrometer.

The results of the first and second analyses are shown in FIGS. 6A-6H. In FIGS. 6A-6H, the results of the first analysis are represented by left bar (dark grey) and the results from the second analysis are represented by the right bar (light grey). The symbol nomenclature for glycan representation is in accordance with Varki, A., Cummings. R. D., Esko J. D., et al., Essentials of Glycobiology, 2nd edition (2009).

As can be seen from FIGS. 6A-6H, the two analyses provided similar results, although there was some variation between the results. This variation can be due to a number of factors, including the instrument used and the completeness of N-glycan analysis. For example, if some species of phosphorylated N-glycans were not identified and/or not quantified, then the total number of phosphorylated N-glycans may be underrepresented, and the percentage of rhGAA bearing the phosphorylated N-glycans at that site may be underrepresented. As another example, if some species of non-phosphorylated N-glycans were not identified and/or not quantified, then the total number of non-phosphorylated N-glycans may be underrepresented, and the percentage of rhGAA bearing the phosphorylated N-glycans at that site may be overrepresented.

FIG. 6A shows the N-glycosylation site occupancy of ATB200. As can be seen from FIG. 6A, the first, second, third, fourth, fifth, and sixth N-glycosylation sites are mostly occupied, with both analyses detecting around or over 90% and up to about 100% of the ATB200 enzyme having an N-glycan detected at each potential N-glycosylation site. However, the seventh potential N-glycosylation site is N-glycosylated about half of the time.

FIG. 6B shows the N-glycosylation profile of the first potential N-glycosylation site, N84. As can be seen from FIG. 6B, the major N-glycan species is bis-M6P N-glycans. Both the first and second analyses detected over 75% of the ATB200 having bis-M6P at the first site, corresponding to an average of about 0.8 mol bis-M6P per mol ATB200 at the first site.

FIG. 6C shows the N-glycosylation profile of the second potential N-glycosylation site, N177. As can be seen from FIG. 6C, the major N-glycan species are mono-M6P N-glycans and non-phosphorylated high mannose N-glycans. Both the first and second analyses detected over 40% of the ATB200 having mono-M6P at the second site, corresponding to an average of about 0.4 to about 0.6 mol mono-M6P per mol ATB200 at the second site.

FIG. 6D shows the N-glycosylation profile of the third potential N-glycosylation site, N334. As can be seen from FIG. 6D, the major N-glycan species are non-phosphorylated high mannose N-glycans, di-, tri-, and tetra-antennary complex N-glycans, and hybrid N-glycans. Both the first and second analyses detected over 20% of the ATB200 having a sialic acid residue at the third site, corresponding to an average of about 0.9 to about 1.2 mol sialic acid per mol ATB200 at the third site.

FIG. 6E shows the N-glycosylation profile of the fourth potential N-glycosylation site, N414. As can be seen from FIG. 6E, the major N-glycan species are bis-M6P and mono-M6P N-glycans. Both the first and second analyses detected over 40% of the ATB200 having bis-M6P at the fourth site, corresponding to an average of about 0.4 to about 0.6 mol bis-M6P per mol ATB200 at the fourth site. Both the first and second analyses also detected over 25% of the ATB200 having mono-M6P at the fourth site, corresponding to an average of about 0.3 to about 0.4 mol mono-M6P per mol ATB200 at the fourth site.

FIG. 6F shows the N-glycosylation profile of the fifth potential N-glycosylation site, N596. As can be seen from FIG. 6F, the major N-glycan species are fucosylated di-antennary complex N-glycans. Both the first and second analyses detected over 70% of the ATB200 having a sialic acid residue at the fifth site, corresponding to an average of about 0.8 to about 0.9 mol sialic acid per mol ATB200 at the fifth site.

FIG. 6G shows the N-glycosylation profile of the sixth potential N-glycosylation site, N826. As can be seen from FIG. 6G, the major N-glycan species are di-, tri-, and tetra-antennary complex N-glycans. Both the first and second analyses detected over 80% of the ATB200 having a sialic acid residue at the sixth site, corresponding to an average of about 1.5 to about 1.8 mol sialic acid per mol ATB200 at the sixth site.

An analysis of the N-glycosylation at the seventh site, N869, showed approximately 40% N-glycosylation, with the most common N-glycans being A4S3S3GF (12%), A5S3G2F (10%), A4S2G2F (8%) and A6S3G3F (8%).

Figure 6H:
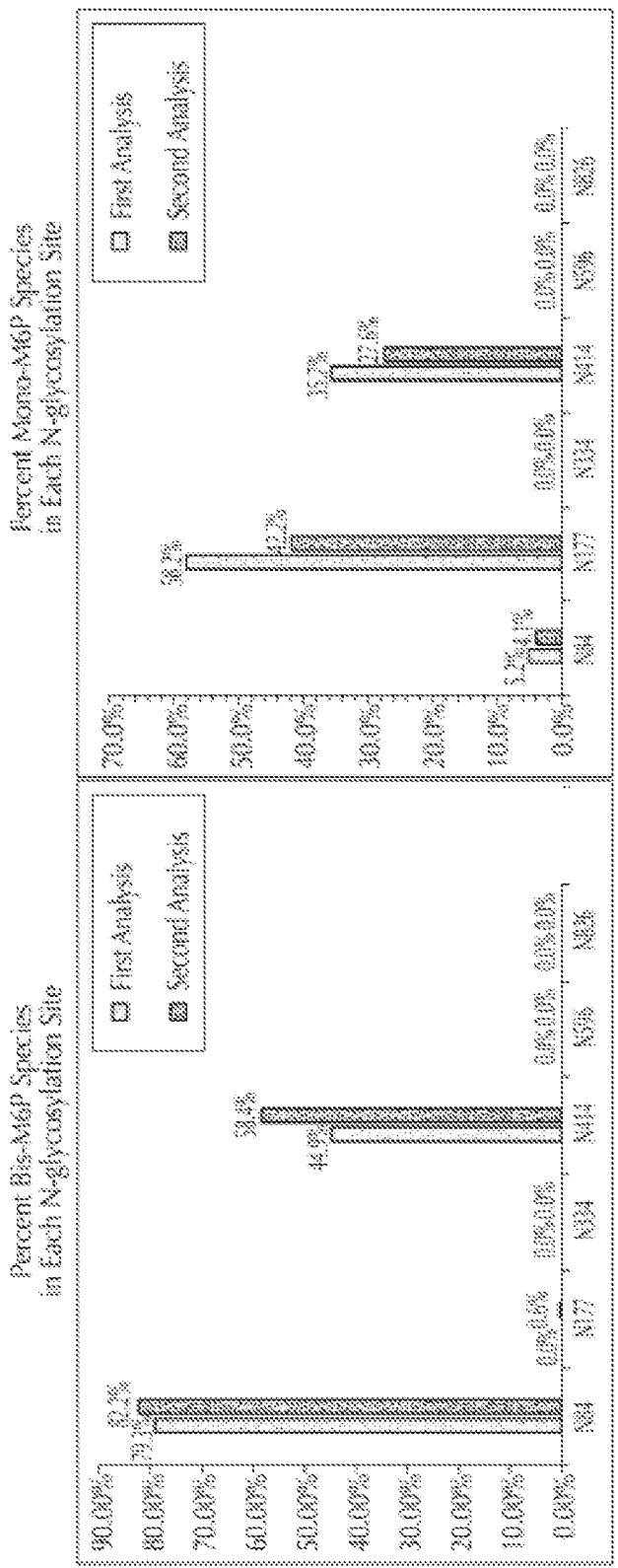

FIG. 6H shows a summary of the phosphorylation at each of the seven potential N-glycosylation sites. As can be seen from FIG. 6H, both the first and second analyses detected high phosphorylation levels at the first, second, and fourth potential N-glycosylation sites. Both analyses detected over 80% of the ATB200 was mono- or bis-phosphorylated at the first site, over 40% of the ATB200 was mono-phosphorylated at the second site, and over 80% of the ATB200 was mono- or bis-phosphorylated at the fourth site.

Another N-glycosylation analysis of ATB200 was performed according to an LC-MS/MS method as described below. This analysis yielded an average N-glycosylation profile over ten lots of ATB200 (FIGS. 32A-32H, FIGS. 33A-33B).

N-linked glycans from ATB200 were released enzymatically with PNGase-F and labeled with 2-Anthranilic acid (2-AA). The 2-AA labeled N-glycans were further processed by solid phase extraction (SPE) to remove excess salts and other contaminants. The purified 2-AA N-glycans were dissolved in acetonitrile/water (20/80; v/v), and 10 micrograms were loaded on an amino-polymer analytical column (apHera™, Supelco) for High Performance Liquid Chromatography with Fluorescence detection (HPLC-FLD) and High Resolution Mass Spectrometry (HRMS) analysis.

The liquid chromatographic (LC) separation was performed under normal phase conditions in a gradient elution mode with mobile phase A (2% acetic acid in acetonitrile) and mobile phase B (5% acetic acid; 20 millimolar ammonium acetate in water adjusted to pH 4.3 with ammonium hydroxide). The initial mobile phase composition was 70% A/30% B. For the fluorescence detection, the parameters for the detector (RF-20Axs, Shimadzu) were Excitation (Ex): 320 nm; Emission (Em):420 nm. The HRMS analysis was carried out using a Quadrupole Time of Flight mass spectrometer (Sciex X500B QTOF) operating in Independent Data Acquisition (IDA) mode. The acquired datafiles were converted into mzML files using MSConvert from ProteoWizard, and then GRITS Toolbox 1.2 Morning Blend software (UGA) was utilized for glycan database searching and subsequent annotation of identified N-glycans. The N-glycans were identified using both precursor monoisotopic masses (m/z) and product ion m/z. Experimental product ions and fragmentation patterns were confirmed in-silico using the GlycoWorkbench 2 Application.

To determine the relative quantitation of N-linked glycans from ATB200, data acquired from the HPLC-FLD-QTOF MS/MS experiment was processed as follows. All of the N-glycan peaks in the FLD chromatogram were integrated, and each peak was assigned a percentage of the total area of all peaks in the FLD chromatogram. The fluorescent signal, expressed as a peak area, is a quantitative measure of the amount of each N-glycan in the sample (FIG. 33A). However, in most cases, multiple N-glycan species were contained in the same FLD peak. Therefore, the mass spectrometer data was also required to obtain relative quantitation of each N-glycan species (Table 5). The ion intensity signal for each N-glycan was "extracted" from the data to create a chromatographic peak called an extracted ion chromatogram (XIC). The XIC aligned with the FLD chromatographic peak and was specific to only one N-glycan species. The XIC peak created from the ion intensity signal was then integrated and this peak area is a relative quantitative measure of the amount of glycan present. Both the FLD peak areas and mass spectrometer XIC peak areas were used to enable relative quantitation of all the N-linked glycan species of ATB200 reported herein.

The results of this LC-MS/MS analysis are provided in Table 5 below. The symbol nomenclature for glycan representation is in accordance with Wopereis W, et al. 2006. Abnormal glycosylation with hypersialylated O-glycans in patients with Sialuria. Biochimica et Biophysica Acta. 1762: 598-607; Gornik O, et al. 2007. Changes of serum glycans during sepsis and acute pancreatitis. Glycobiology. 17:1321-1332 DOI 10.1093/glycob/cwm106; Kattla J J, et al. 2011. Biologic protein glycosylation. In: Murray Moo-Young (ed.), Comprehensive Biotechnology, Second Edition, 3:467-486; Tharmalingam-Jaikaran T, et al. N-glycan profiling of bovine follicular fluid at key dominant follicle developmental stages. 2014. Reproduction. 148:569-580; Clerc F, et al. Human plasma protein N-glycosylation. 2015. Glycoconj J. DOI 10.1007/s10719-015-9626-2; and Blackler R J, et al. 2016. Single-chain antibody-fragment M6P-1 possesses a mannose 6-phosphate monosaccharide-specific binding pocket that distinguishes N-glycan phosphorylation in a branch-specific manner. Glycobiology. 26-2:181-192.

an average M6P content of about 1.4 mol M6P/mol ATB200, accounting for an average mono-M6P content of about 0.25 mol mono-M6P/mol ATB200 and an average bis-M6P content of about 0.56 mol bis-M6P/mol ATB200; the second potential N-glycosylation site of ATB200 has an average M6P content of about 0.5 mol M6P/mol ATB200, with the primary phosphorylated N-glycan species being mono-M6P N-glycans; the third potential N-glycosylation site of ATB200 has an average sialic acid content of about 1 mol sialic acid/mol ATB200; the fourth potential N-glycosylation site of ATB200 has an average M6P content of about 1.4 mol M6P/mol ATB200, accounting for an average mono-M6P content of about 0.35 mol mono-M6P/mol ATB200 and an average bis-M6P content of about 0.52 mol bis-M6P/mol ATB200; the fifth potential N-glycosylation site of ATB200 has an average sialic acid content of about 0.86 mol sialic acid/mol ATB200; the sixth potential N-glycosylation site of ATB200 has an average sialic acid content of about 4.2 mol sialic acid/mol ATB200; and the seventh potential N-glycosylation site of ATB200 has an average sialic acid content of about 0.86 mol sialic acid/pol ATB200.

Also according to this 2-AA and LC-MS/MS analytical technique, an average of about 65% of the N-glycans at the first potential N-glycosylation site of ATB200 are high mannose N-glycans, about 89% of the N-glycans at the second potential N-glycosylation site of ATB200 are high mannose N-glycans, over half of the N-glycans at the third

TABLE 5

Type and Prevalence of Oligosaccharides identified on ATB200 based on 2-AA glycan mapping and LC-MS/MS identification

| High Mannose N-Glycans | % Total | Complex N-Glycans | % Total | Complex N-Glycans | % Total | Complex N-Glycans | % Total |
|---|---|---|---|---|---|---|---|
| 2P-M7 | 11.39 | FA2G2S1 | 3.89 | A3G3S1 + 1Ac | 0.65 | FA2G2S1 + 1AC | 0.29 |
| P-M7 | 7.97 | FA2G2S2 | 3.42 | A3G2S2 + 1Ac | 0.64 | A4G3 | 0.29 |
| M6 | 6.89 | A2G2S2 | 3.32 | A1G1S1 | 0.63 | A4G4 + 3KDN | 0.29 |
| P-M6 | 3.42 | FA2G2 | 2.77 | A4G3S1 | 0.61 | A4G4S3 | 0.28 |
| M5 | 2.06 | FA4G4S3 | 2.26 | FA3G3 | 0.61 | FA5G4 | 0.24 |
| P-M5 | 1.67 | A2G2S1 | 2.25 | A1G1 | 0.6 | A4G3S2 | 0.21 |
| 2P-M8 | 1.27 | FA3G3S1 | 2.12 | FA2G2S2 + 1Ac | 0.57 | FA1 | 0.21 |
| P-M8 | 1.17 | A3G3S2 | 1.8 | A3G2S1 | 0.57 | FA4G4 | 0.21 |
| BP-M6 | 0.9 | FA2G1 | 1.66 | A3G2S1 | 0.56 | A3G1 | 0.21 |
| M7 | 0.81 | A2G2 | 1.46 | A2G2S2 + 1Ac | 0.5 | FA4G3S2 | 0.21 |
| BP-M7 | 0.69 | FA3G3S1 | 1.42 | FA3G2 | 0.45 | FA3G2S2 | 0.21 |
| M4 | 0.14 | A4G4S1 | 1.28 | A3G3 + 3KDN | 0.45 | A1 | 0.2 |
| BP2-M5 | 0.04 | FA3G3S2 | 1.25 | A4G3S1 | 0.45 | A4G2 | 0.19 |
| BP2-M6 | 0.01 | FA4G4(1LN)S3 | 1.1 | A2G1S1 | 0.41 | FA4G3 | 0.19 |
| Hybrid N-Glycans | % Total | FA4G4S1 | 1.08 | A3G2 | 0.4 | FA3 | 0.18 |
| FA1P-M6 | 2.16 | A3G3 | 1.08 | FA4G4S1 + LN | 0.4 | A1G1S1 | 0.18 |
| M5A1G1S1 | 1.56 | FA4G4S4 | 1.07 | FA3G2S1 | 0.39 | A4G1S1 | 0.16 |
| FP-M6A1G1S1 | 0.42 | FA3G3S3 | 1.04 | FA2 | 0.38 | FA1G1 | 0.15 |
| A1M5 | 0.36 | FA4G4S2 | 0.94 | FA4G4S2 + LN | 0.38 | FA3G1 | 0.14 |
| A1G1M5 | 0.32 | A2G1 | 0.94 | A3G2S2 | 0.37 | FA5G4S2 | 0.12 |
| P-M6A1G1S1 | 0.17 | FA2G1S1 | 0.94 | A2 | 0.34 | A3G1S1 | 0.11 |
| Summary | Total | A4G4 | 0.91 | FA4G4(2LN)S3 | 0.33 | A3 | 0.11 |
| High Mannose N-Glycans | 38% | FA1G1S1 | 0.91 | FA2G2Sg1 | 0.32 | FA3G3S3 + 1Ac | 0.1 |
| Hybrid N-Glycans | 5% | FA2G2S2 + 2Ac | 0.76 | FA4G4(1LN)S4 | 0.31 | A2G2S1 + 1Ac | 0.09 |
| Complex N-Glycans | 57% | A4G4S2 | 0.69 | A3G3S3 | 0.29 | FA3G1S1 | 0.06 |

Based on this 2-AA and LC-MS/MS analysis, and as further summarized in FIG. 33C, the ATB200 tested has an average M6P content of 3-5 mol per mol of ATB200 (accounting for both mono-M6P and bis-M6P) and sialic acid content of 4-7 mol per mol of ATB200.

As shown in FIGS. 32A-32H and summarized in FIG. 33B, the first potential N-glycosylation site of ATB200 has potential N-glycosylation site of ATB200 are sialylated (with nearly 20% fully sialylated) and about 85% of the N-glycans at the third potential N-glycosylation site of ATB200 are complex N-glycans, about 84% of the N-glycans at the fourth potential N-glycosylation site of ATB200 are high mannose N-glycans, about 70% of the N-glycans at the fifth potential N-glycosylation site of ATB200 are sialylated (with about 26% fully sialylated) and about 100% of the N-glycans at the fifth potential N-glycosylation site of ATB200 are complex N-glycans, about 85% of the N-glycans at the sixth potential N-glycosylation site of ATB200 are sialylated (with nearly 27% fully sialylated) and about 98% of the N-glycans at the sixth potential N-glycosylation site of ATB200 are complex N-glycans, and about 87% of the N-glycans at the seventh potential N-glycosylation site of ATB200 are sialylated (with nearly 8% fully sialylated) and about 100% of the N-glycans at the seventh potential N-glycosylation site of ATB200 are complex N-glycans.

Example 4: Analytical Comparison of ATB200 and Myozyme®/Lumizyme®

Figure 7:
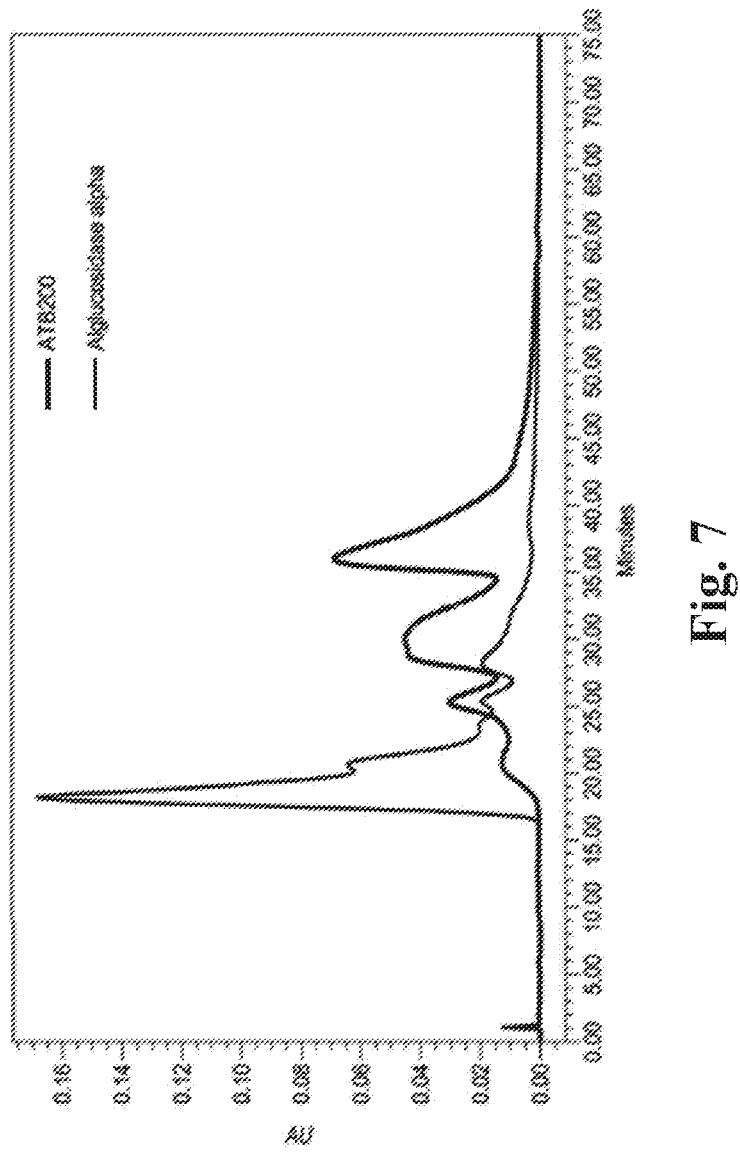
FIG. 7 is a graph showing Polywax elution profiles of Lumizyme® (alglucosidase alfa, thinner line, eluting to the left) and ATB200 (thicker line, eluting to the right).

Purified ATB200 and Lumizyme® N-glycans were evaluated by MALDI-TOF to determine the individual N-glycan structures found on each ERT. Lumizyme® was obtained from a commercial source. As shown in FIG. 7, ATB200 exhibited four prominent peaks eluting to the right of Lumizyme®. This confirms that ATB200 was phosphorylated to a greater extent than Lumizyme® since this evaluation is by terminal charge rather than CIMPR affinity. As summarized in FIG. 8, ATB200 samples were found to contain lower amounts of non-phosphorylated high-mannose type N-glycans than Lumizyme®.

Figure 9A:
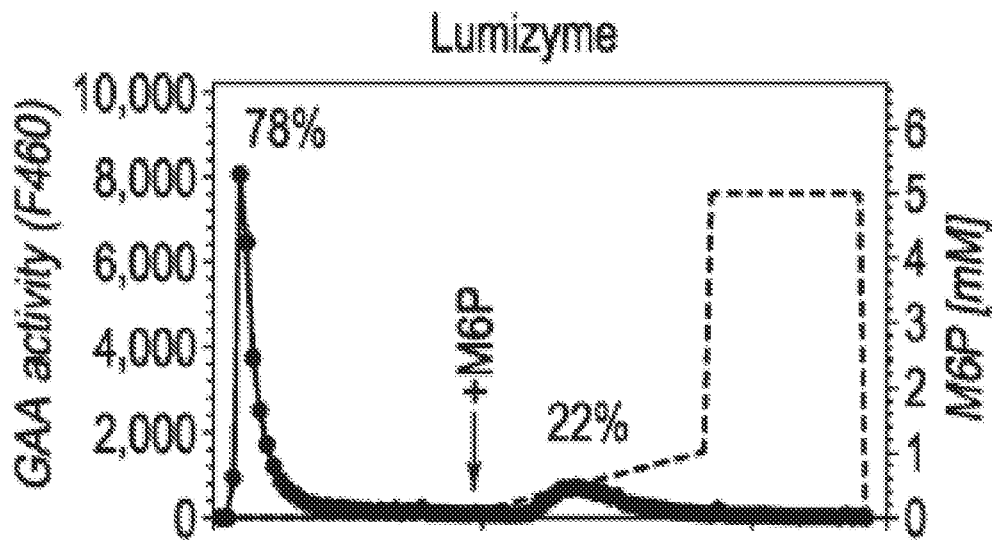
FIGS. 9A and 9B are graphs showing the results of CIMPR affinity chromatography of Lumizyme® and Myozyme®, respectively.
Figure 9B:
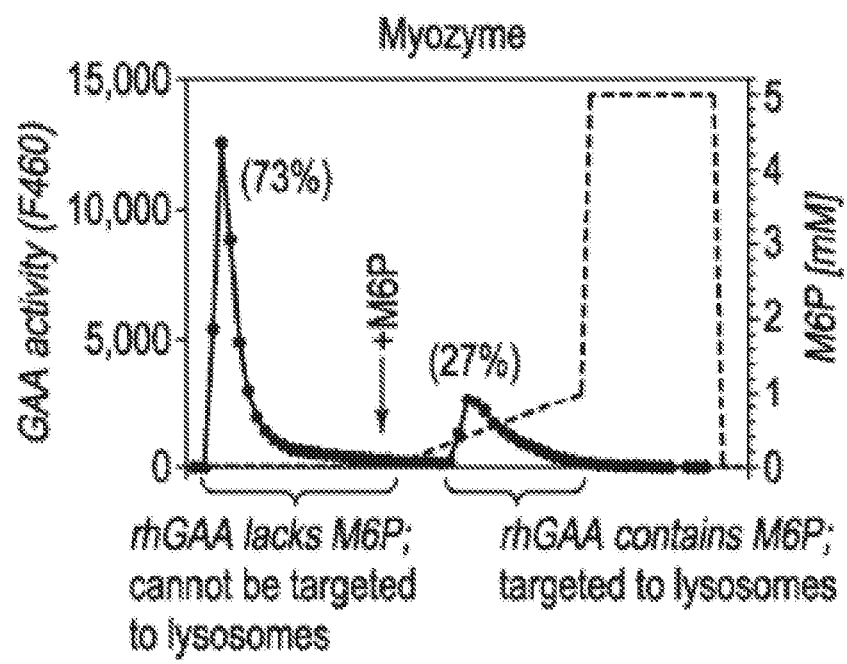

To evaluate the ability of the conventional rhGAAs in Myozyme® and Lumizyme® to interact with the CIMPR, the two conventional rhGAA preparations were injected onto a CIMPR affinity column (which binds rhGAA having M6P groups) and the flow through collected. The bound material was eluted with a free M6 gradient. Fractions were collected in 96-well plate and GAA activity assayed by 4MU-α-glucosidase substrate. The relative amounts of unbound (flow through) and bound (M6P eluted) rhGAA were determined based on GAA activity and reported as the fraction of total enzyme. FIGS. 9A and 9B show the binding profile of rhGAAs in Myozyme® and Lumizyme®: 73% of the rhGAA in Myozyme®[1] (FIG. 9B) and 78% of the rhGAA in Lumizyme® (FIG. 9A) did not bind to the CIMPR. Indeed, only 27% of the rhGAA in Myozyme® and 22% of the rhGAA in Lumizyme® contained M6P that can be productive to target it to the CIMPR on muscle cells. In contrast, as shown in FIG. 5, under the same condition, more than 70% of the rhGAA in ATB200 was found to bind to the CIMPR.

Figures 10A, 10B:
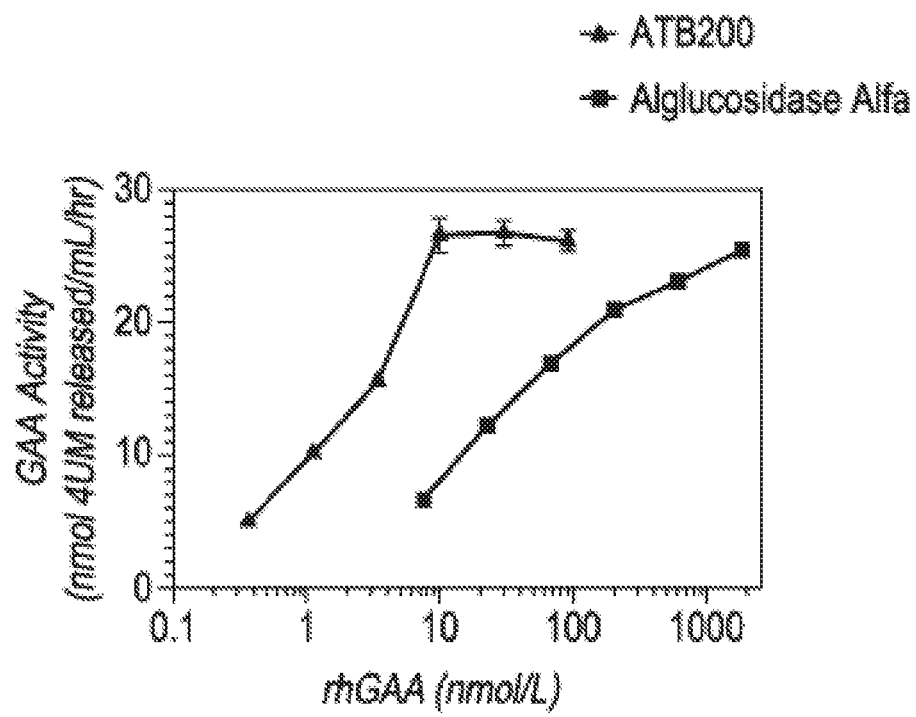
FIG. 10A is a graph comparing the CIMPR binding affinity of ATB200 rhGAA (left trace) with that of Lumizyme® (right trace).
FIG. 10B is a table comparing the bis-M6P content of Lumizyme® and ATB200 rhGAA.

In addition to having a greater percentage of rhGAA that can bind to the CIMPR, it is important to understand the quality of that interaction. Lumizyme® and ATB200 receptor binding was determined using a CIMPR plate binding assay. Briefly, CIMPR-coated plates were used to capture GAA. Varying concentrations of rhGAA were applied to the immobilized receptor and unbound rhGAA was washed off. The amount of remaining rhGAA was determined by GAA activity. As shown in FIG. 10A, ATB200 bound to CIMPR significantly better than Lumizyme® FIG. 10B shows the relative content of bis-M6P N-glycans in Lumizyme® (a conventional rhGAA product) and ATB200 according to the invention. For Lumizyme®, there is on average only 10% of molecules having a bis-phosphorylated N-glycan. In contrast, on average every rhGAA molecule in ATB200 has at least one bis-phosphorylated N-glycan.

Overall, the higher content of M6P N-glycans in ATB200 than in Lumizyme® indicates that the higher portion of rhGAA molecules in ATB200 can target muscle cells. As shown above, the high percentage of mono-phosphorylated and bis-phosphorylated structures determined by MALDI agree with the CIMPR profiles which illustrated significantly greater binding of ATB200 to the CIMPR receptor. N-glycan analysis via MALDI-TOF mass spectrometry confirmed that on average each ATB200 molecule contains at least one natural bis-M6P N-glycan structure. This higher bis-M6P N-glycan content on ATB200 directly correlated with high-affinity binding to CIMPR in M6P receptor plate binding assays (Ku about 2-4 nM).

The relative cellular uptake of ATB200 and Lumizyme® rhGAA were compared using normal and Pompe fibroblast cell lines. Comparisons involved 5-100 nM of ATB200 according to the invention with 10-500 nM conventional rhGAA product Lumizyme® After 16-hr incubation, external rhGAA was inactivated with TRIS base and cells were washed 3-times with PBS prior to harvest. Internalized GAA measured by 4MU-α-Glucoside hydrolysis and was graphed relative to total cellular protein and the results appear in FIGS. 11A-11C.

ATB200 was also shown to be efficiently internalized into cells. As depicted in FIGS. 11A-11B, ATB200 is internalized into both normal and Pompe fibroblast cells and is internalized to a greater degree than the conventional rhGAA product Lumizyme®. ATB200 saturates cellular receptors at about 20 nM, while about 250 nM of Lumizyme® is needed to saturate cellular receptors. The uptake efficiency constant ($K_{uptake}$) extrapolated from these results is 2-3 nm for ATB200 and 56 nM for Lumizyme®, as shown by FIG. 11C. These results suggest that ATB200 is a well-targeted treatment for Pompe disease.

Example 5: ATB200 and Pharmacological Chaperone

Figure 12:
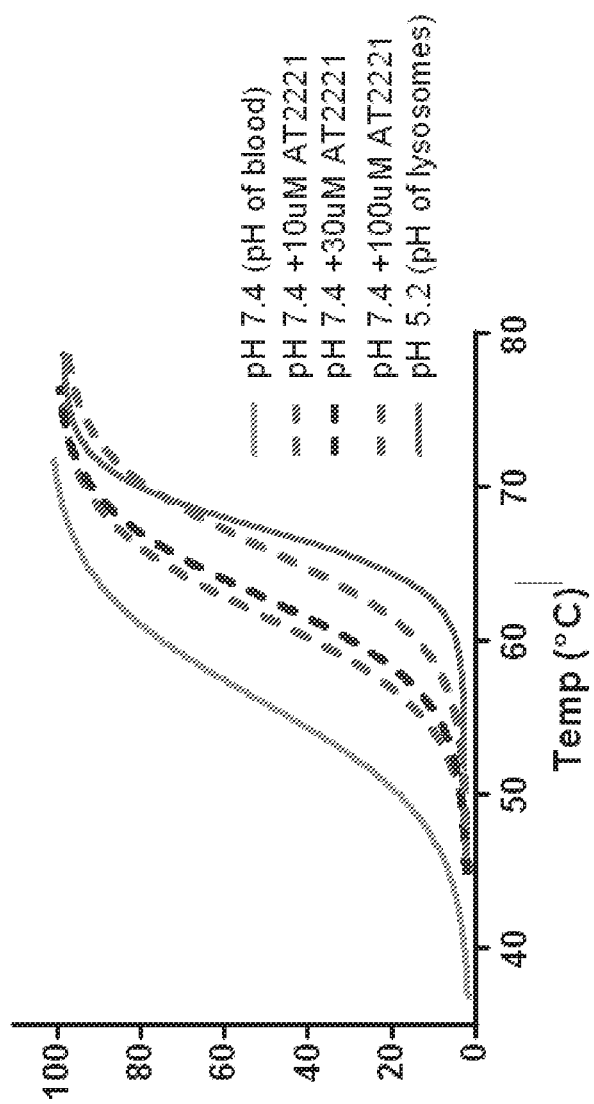
FIG. 12 depicts the stability of ATB200 in acidic or neutral pH buffers evaluated in a thermostability assay using SYPRO Orange, as the fluorescence of the dye increases when proteins denature.

The stability of ATB200 in acidic or neutral pH buffers was evaluated in a thermostability assay using SYPRO Orange, as the fluorescence of the dye increases when proteins denature. As shown in FIG. 12, the addition of AT2221 stabilized ATB200 at pH 7.4 in a concentration-dependent manner, comparable to the stability of ATB200 at pH 5.2, a condition that mimics the acidic environment of the lysosome. As summarized in Table 6, the addition of AT2221 increased the melting temperature ($T_m$) of ATB200 by nearly 10° C.

TABLE 6

Stability of ATB200 In Combination with AT2221

| Test Condition | Tm (° C.) |
| --- | --- |
| pH 7.4 | 56.2 |
| pH 7.4 + 10 µM AT2221 | 61.6 |
| pH 7.4 + 30 µM AT2221 | 62.9 |
| pH 7.4 + 100 µM AT2221 | 66.0 |
| pH 5.2 | 67.3 |

Example 6: Co-Administration of ATB200 and AT2221 in Gaa KO Mice

The therapeutic effects of ATB200 and AT2221 were evaluated and compared against those of Alglucosidase alfa in Gaa KO mice. For the study, male Gaa KO (3- to 4-month old) and age-matched wild-type (WT) mice were used. Alglucosidase alfa was administered via bolus tail vein intravenous (IV) injection. In the co-administration regimen, AT2221 was administered via oral gavage (PO) 30 minutes prior to the IV injection of ATB200. Treatment was given biweekly. Treated mice were sacrificed after 14 days from the last administration and various tissues were collected for further analysis. Table 7 summarizes the study design:

TABLE 7

Co-administration Study Design

| Genotype | Treatment | Drug Dosage per Administration (bi-weekly) | Number of Administration |
|---|---|---|---|
| Gaa KO | Vehicle | N/A | 6 |
| Gaa KO | Alglucosidase alfa | 20 mg/kg | 6 |
| Gaa KO | ATB200/AT2221 | 20 mg/kg (ATB200) 10 mg/kg (AT2221) | 6 |
| WT (Sve 129) | Not Treated | N/A | N/A |

Figure 13:
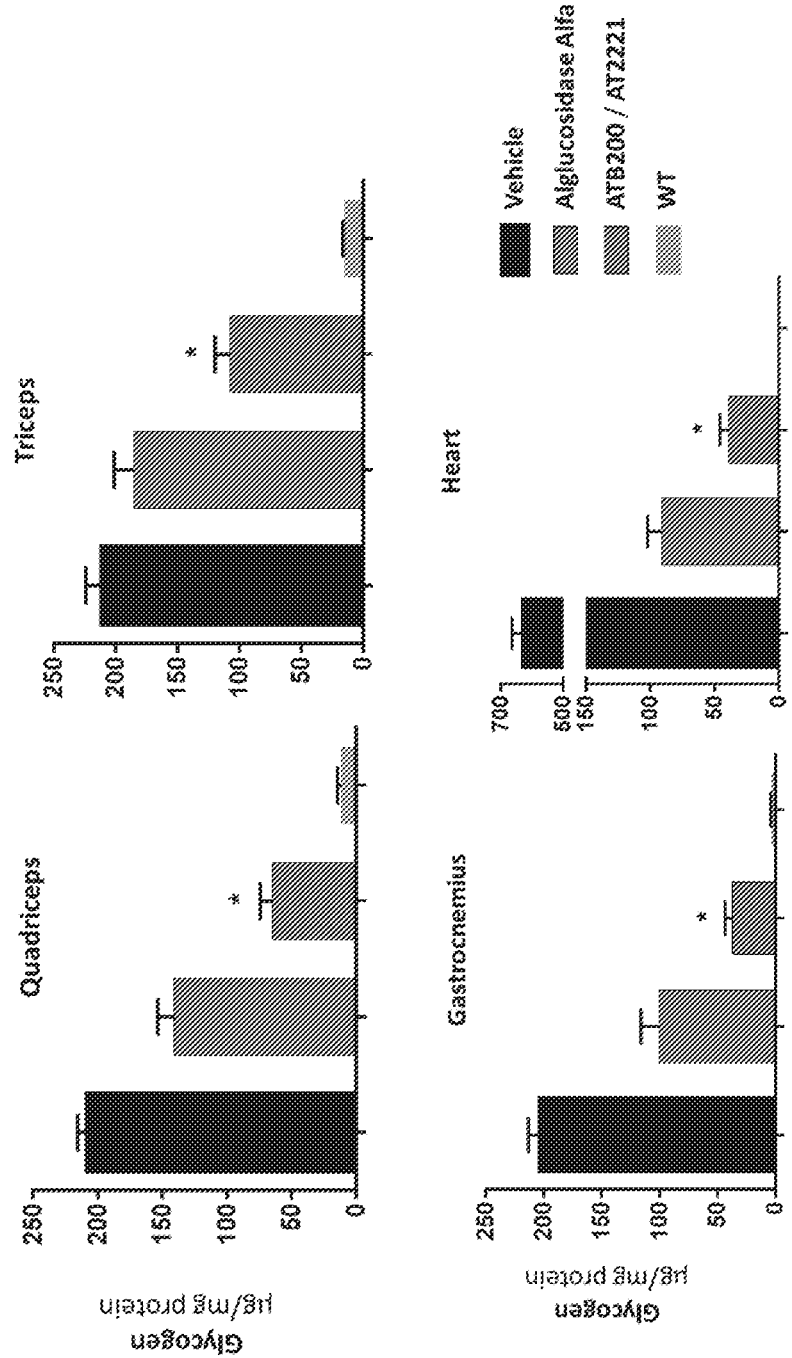
FIG. 13 shows tissue glycogen content of WT mice or Gaa KO mice treated with a vehicle, alglucosidase alfa, or ATB200/AT2221, determined using amyloglucosidase digestion. Bars represent Mean±SEM of 7 mice/group. * $p<0.05$ compared to alglucosidase alfa in multiple comparison using Dunnett's method under one-way ANOVA analysis.

Tissue glycogen content in tissues samples was determined using amyloglucosidase digestion, as discussed above. As shown in FIG. 13, a combination of 20 mg/kg ATB200 and 10 mg/kg AT2221 significantly decreased the glycogen content in four different tissues (quadriceps, triceps, gastrocnemius, and heart) as compared to the same dosage of alglucosidase alfa.

Figure 14:
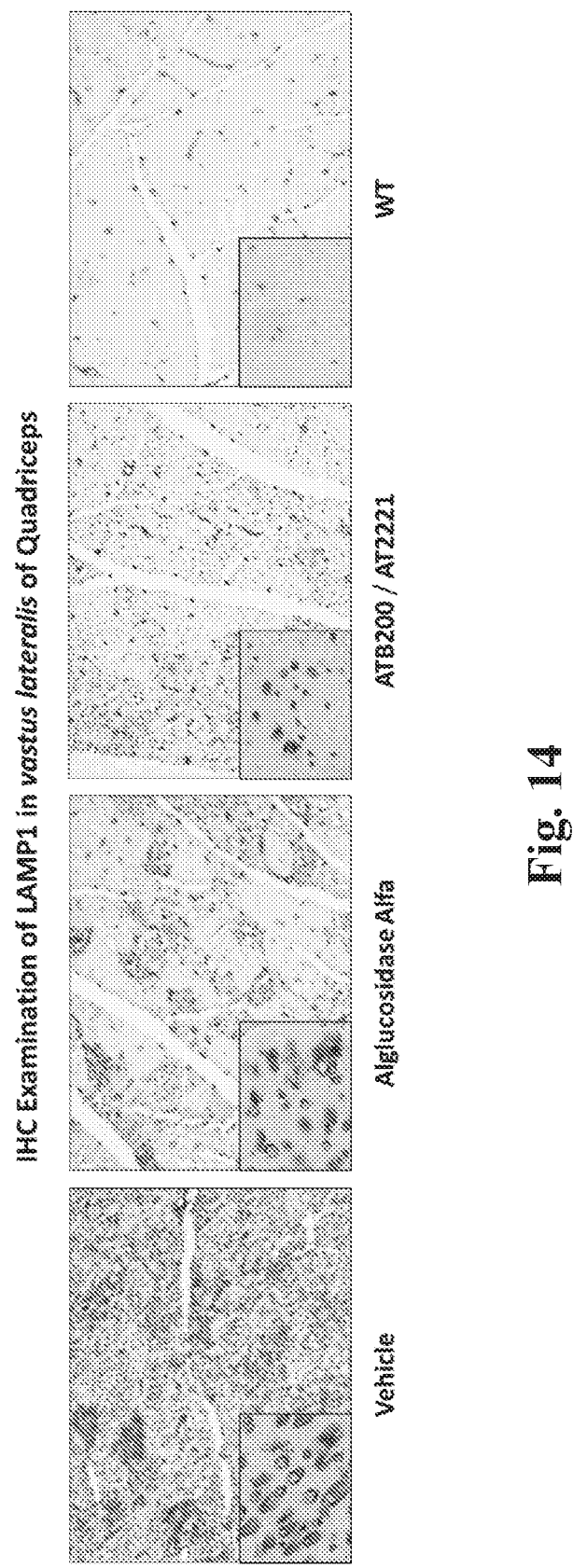
FIG. 14 depicts LAMP1-positive vesicles in muscle fibers of Gaa KO mice treated with a vehicle, alglucosidase alfa, or ATB200/AT2221 or WT mice. Images were taken from vastus lateralis and were representative of 7 mice per group. Magnification=200× (1,000× in insets).

Tissue samples were also analyzed for biomarker changes following the methods discussed in: Khanna R, et al. (2012), "The pharmacological chaperone AT2220 increases recombinant human acid α-glucosidase uptake and glycogen reduction in a mouse model of Pompe disease," Plos One 7(7): e40776; and Khanna. R et al. (2014), "The Pharmacological Chaperone AT2220 Increases the Specific Activity and Lysosomal Delivery of Mutant Acid α-Glucosidase, and Promotes Glycogen Reduction in a Transgenic Mouse Model of Pompe Disease," PLoS ONE 9(7): e102092. As shown in FIG. 14, a profound increase in and enlargement of LAMP1-positive vesicles was seen in muscle fibers of Gaa KO animals compared to WT, indicative of lysosomal proliferation. Co-administration of ATB200/AT2221 led to more fibers with normalized LAMP1 level, while the remaining LAMP1-positive vesicles also reduced in size (insets).

Figure 15A:
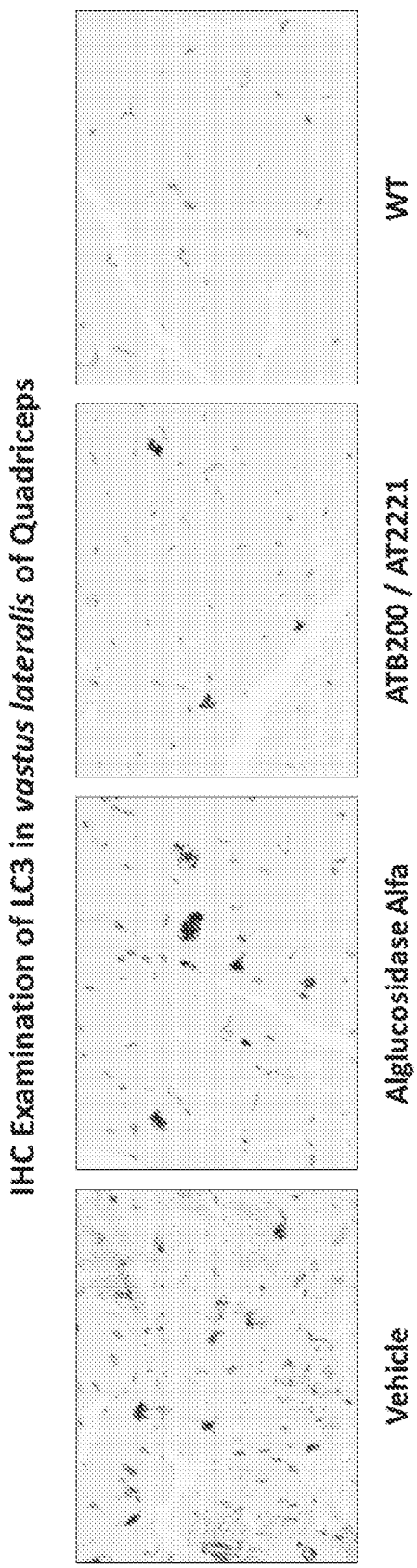
FIG. 15A shows LC3-positive aggregates in muscle fibers of Gaa KO mice treated with a vehicle, alglucosidase alfa, or ATB200/AT2221 or WT mice. Images were taken from vastus lateralis and were representative of 7 mice per group. Magnification=400×.
Figure 15B:
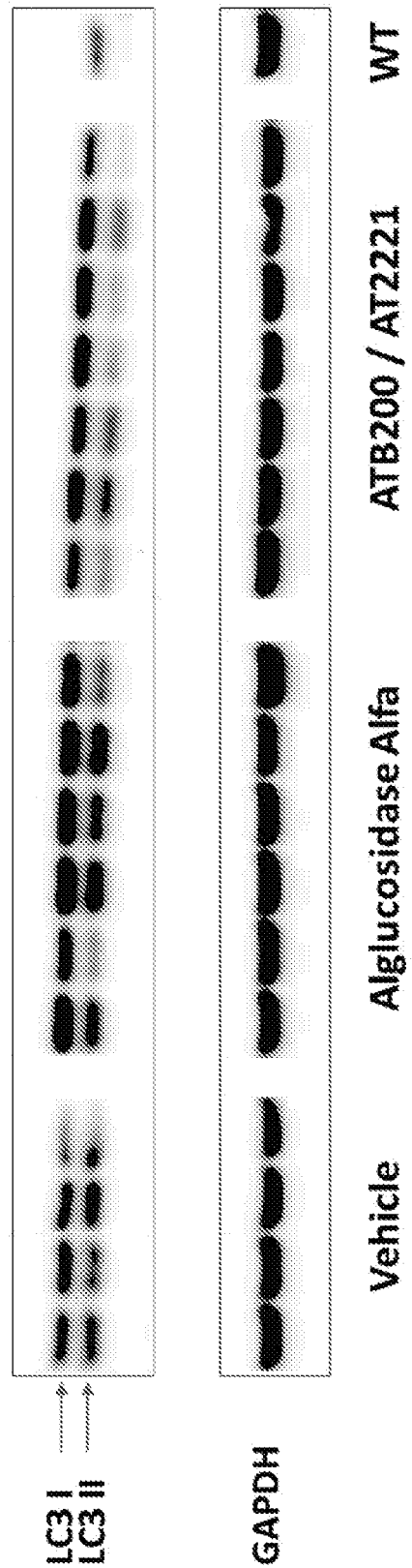
FIG. 15B shows a western blot analysis of LC3 II protein. A total of 30 mg protein was loaded in each lane.

Similarly, intense LC3-positive aggregates in the muscle fibers of untreated Gaa KO mice signify the presence of autophagic zones and autophagy build-up. LC3-positive aggregates (ted) were preferentially reduced in mice treated with ATB200/AT2221 co-administration as compared to mice treated with alglucosidase alfa (FIG. 15A). A similar observation was made when the expression of LC3 was assessed using western blot. As shown in FIG. 15B, the majority of animals treated with ATB200/AT2221 showed a significant decrease in levels of LC3 IL the lipidated form that is associated with autophagosomes, suggesting an improved autophagy flux. In comparison, the effect of alglucosidase alfa on autophagy was modest.

Figure 16:
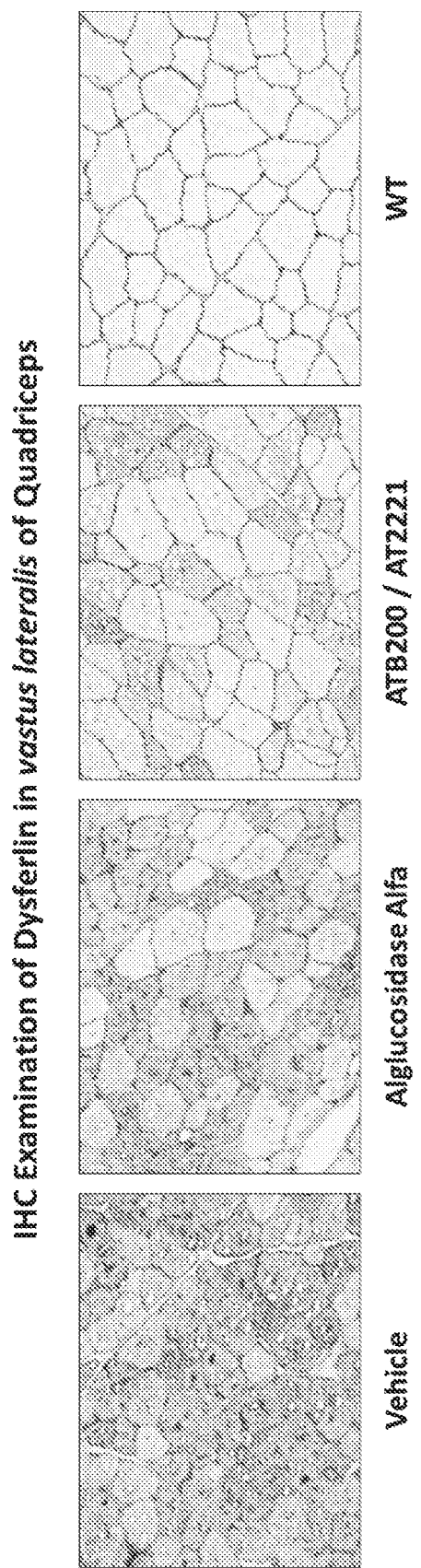
FIG. 16 shows Dysferlin expression in muscle fibers of Gaa KO mice treated with a vehicle, alglucosidase alfa, or ATB200/AT2221 or WT mice. Images were taken from vastus lateralis and were representative of 7 mice per group. Magnification=200×.

Dysferlin, a protein involved in membrane repair and whose deficiency/mistrafficking is associated with a number of muscular dystrophies, w as also assessed. As shown in FIG. 16, dysferlin (brown) was heavily accumulated in the sarcoplasm of Gaa KO mice. Compared to alglucosidase alfa, ATB200/AT2221 was able to restore dysferlin to the sarcolemma in a greater number of muscle fibers.

These data are consistent with improvements at the cellular level demonstrated in human Pompe disease patients treated with ATB200 and miglustat, (e.g., the patients exhibit reduced levels of biomarkers of glycogen accumulation and muscle injury), leading not only to effective treatment of Pompe disease but also a reversal in disease progression. Clinical data in human Pompe disease patients are summarized in Examples 8-13, below.

Example 7: Single Fiber Analysis

Figure 17:
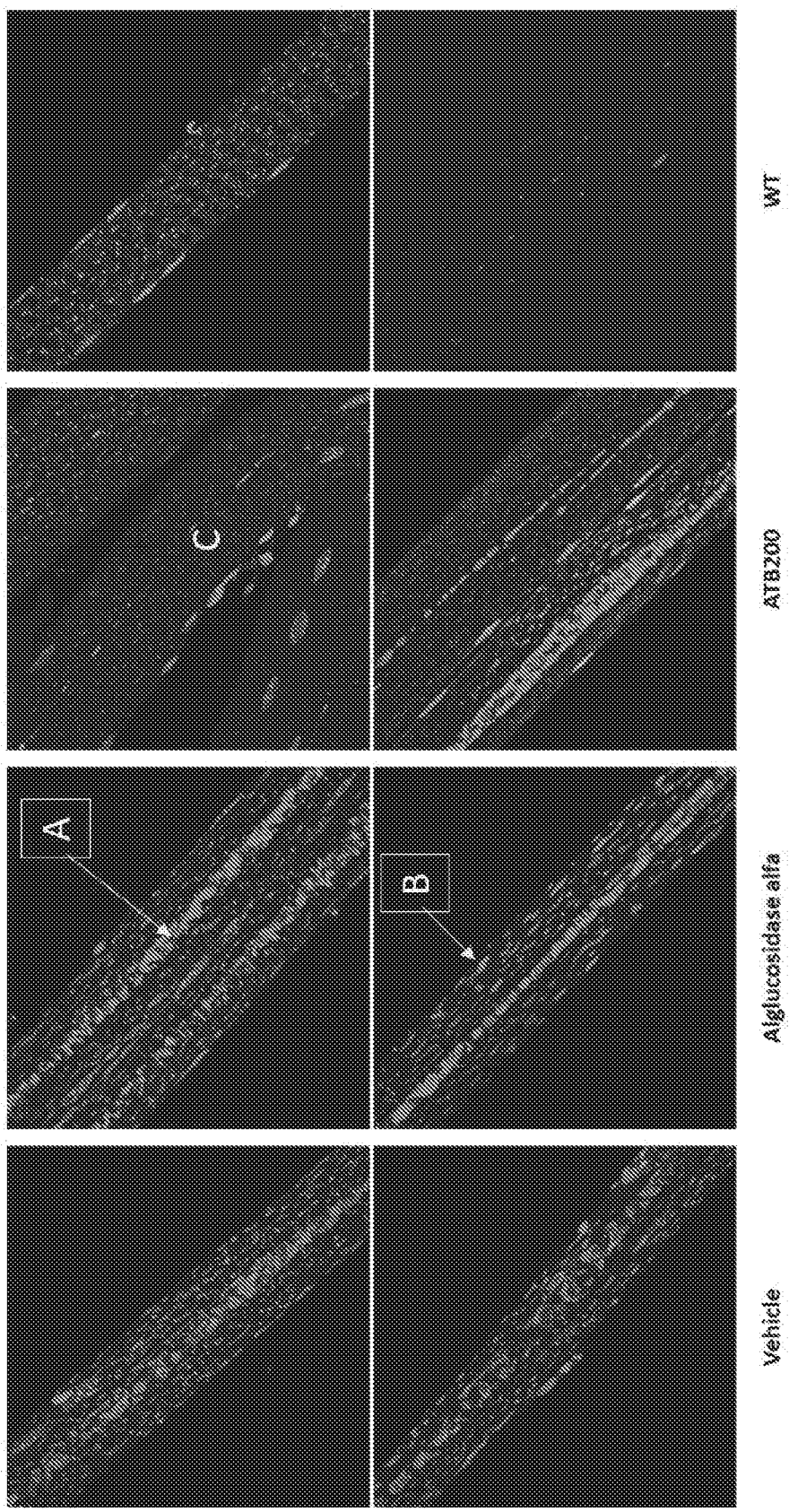
FIG. 17 depicts co-immunofluorescent staining of LAMP1 (green) (see for example, "B") and LC3 (red) (see, for example, "A") in single fibers isolated from the white gastrocnemius of Gaa KO mice treated with a vehicle, alglucosidase alfa, or ATB200. "C" depicts clearance of autophagic debris and absence of enlarged lysosomes. A minimum of 30 fibers were examined from each animal.

As shown in FIG. 17, majority of the vehicle-treated mice showed grossly enlarged lysosomes (green) (see, for example "B") and the presence of massive autophagic buildup (red) (see, for example "A"). Myozyme®-treated mice did not show any significant difference as compared to vehicle-treated mice. In contrast, most fibers isolated from mice treated with ATB200 showed dramatically decreased lysosome size (see, for example, "C"). Furthermore, the area with autophagic buildup was also reduced to various degrees (see, for example, "C"). As a result, a significant portion of muscle fibers analyzed (36-60%) from ATB200-treated mice appeared normal or near-normal. Table 8 below summarizes the single fiber analysis shown in FIG. 17.

TABLE 8

Single Fiber Analysis

| Treatment | Animal Analyzed | Total Number of Fibers Analyzed (n) | Lysosome Enlargement | Fibers with Autophagy Buildup | Fibers with Normal or Near-normal Appearance |
|---|---|---|---|---|---|
| WT | 2 | 65 | – | — | 100% |
| Vehicle | 2 | 65 | + | >90% | <10% |
| Alglucosidase alfa | 4 | 150 | + | >90% | <10% |
| ATB200 | 5 | 188 | Dramatic size decrease in most fibers | 40-64%* | 36-60% |

*This included fibers with varying degree of reduction in autophagic buildup. Overall, the extent of the buildup was smaller in ATB200-treated group compared to Vehicle- or alglucosidase alfa-treated group.

Figure 18:
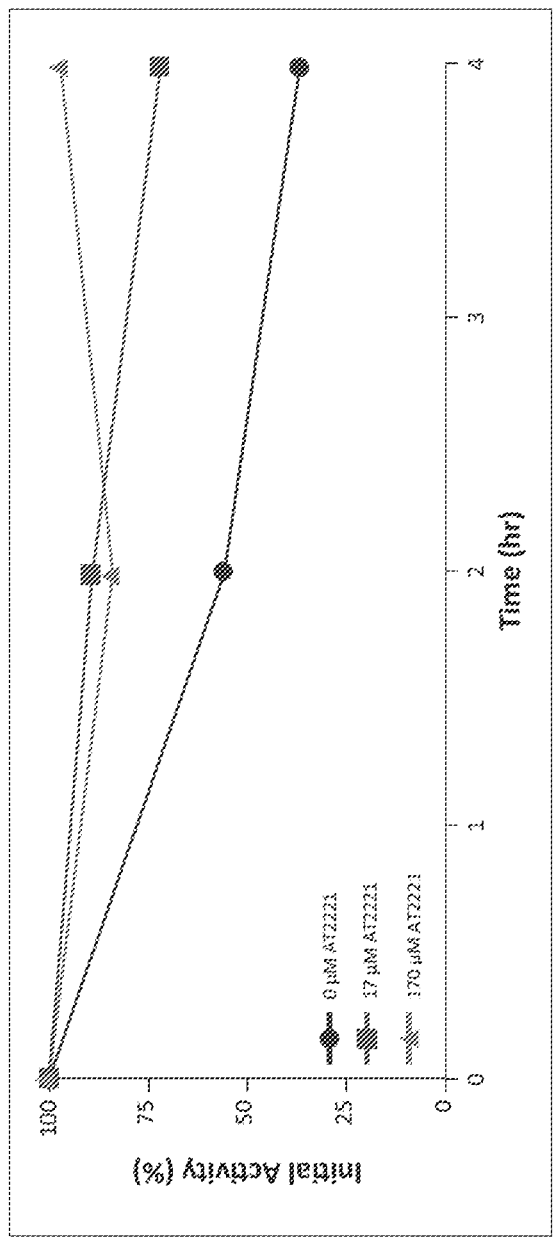
FIG. 18 depicts stabilization of ATB200 by AT2221 at 17 µM, and 170 µM AT2221, respectively, as compared to ATB200 alone.

Overall, the data indicate that ATB200, with its higher M6P content, both alone and further stabilized by the pharmacological chaperone AT2221 at the neutral pH of blood, is more efficient in tissue targeting and lysosomal trafficking compared to alglucosidase alfa when administered to Gaa KO mice, consistent with the stabilization of ATB200 by AT2221 as depicted in FIG. 18. As a result, administration of ATB200 and co-administration of ATB200/AT2221 was more effective than alglucosidase alfa in correcting some of the disease-relevant pathologies, such as glycogen accumulation, lysosomal proliferation, and formation of autophagic zones. Due to these positive therapeutic effects, administration of ATB200 and ATB200/AT2221 co-administration is shown to improve the chance of muscle fiber recovery from damage and even to reverse damage by clearing glycogen that had accumulated in the cell due to lack of optimal GAA activity. As with Example 6, these data are also consistent with improvements at the cellular level demonstrated in human Pompe disease patients that lead to both effective treatment of Pompe disease and reversal in disease progression following administration of ATB200 and miglustat. Clinical data in human Pompe disease patients are summarized in Examples 8-13, below.

Figure 19A:
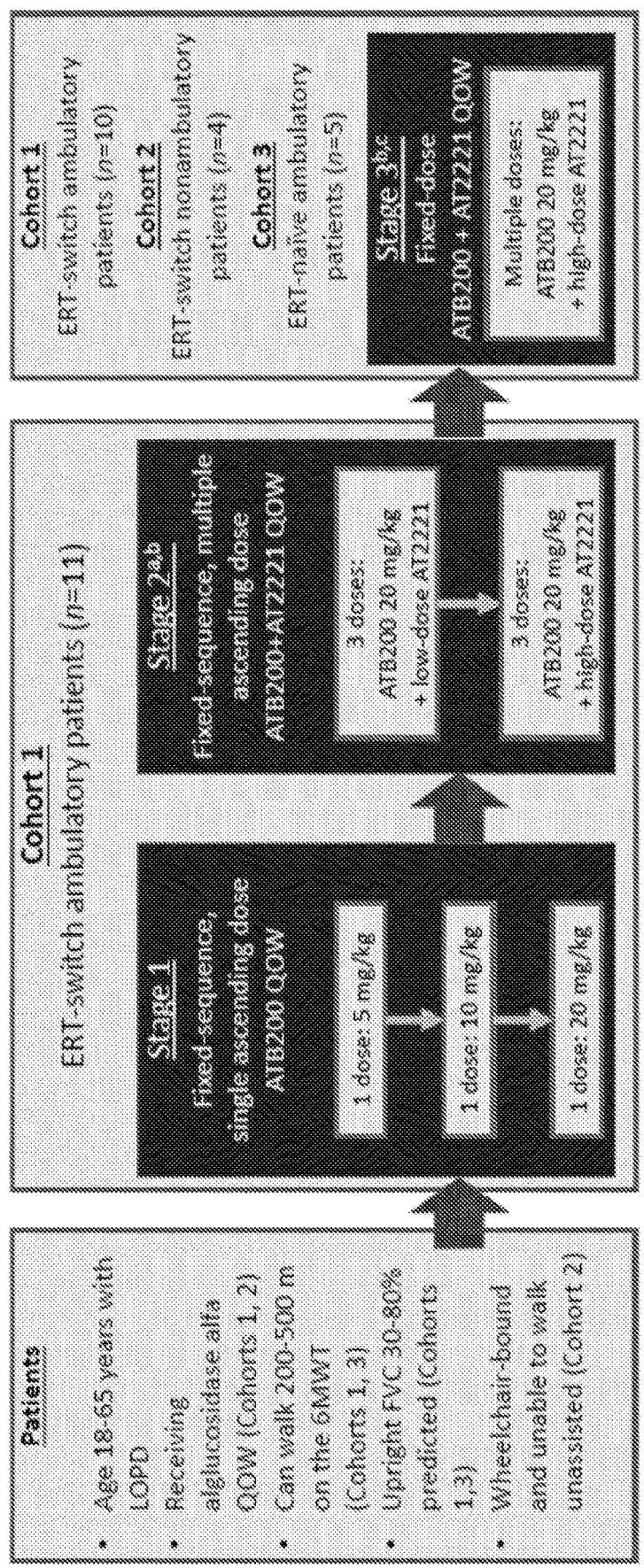
FIGS. 19A and 19B show the ATB200-02 study design. Low dose=130 mg. High dose=260 mg.
Figure 19B:
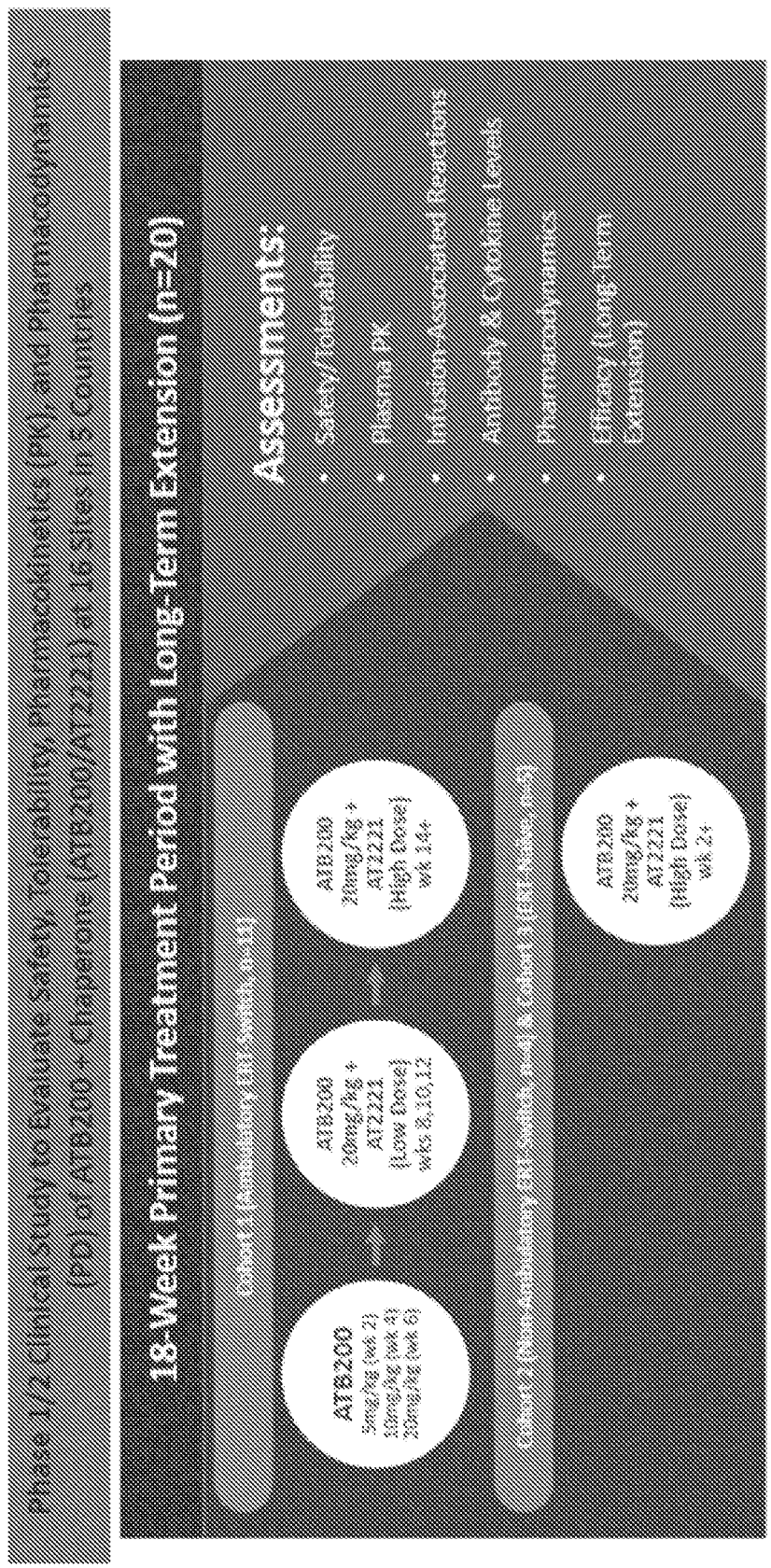

Example 8: The ATB200-02 Trial: An In-Human Study of ATB200/AT2221 in Patients with Pompe Disease Preclinical studies were conducted in Gaa knockout mice to evaluate the pharmacokinetics (PK) and efficiency of glycogen reduction at varying ATB200 enzyme replacement therapy (ERT) and AT2221 chaperone doses. These data were used to estimate the comparable AT2221 chaperone doses in humans. Study ATB200-02 (NCT02675465) was then designed as an open-label fixed-sequence, ascending dose, first-in-human, phase 1/2 study to evaluate the safety, tolerability, PK, pharmacodynamics (PD), and efficacy of ATB200 co-administered with AT2221 in patients with Pompe disease. FIGS. 19A-19B present the ATB200-02 study design. Ambulatory patients who have previously received enzyme replacement therapy with alglucosidase alfa are referred to as ambulatory ERT-switch (or ERT-switch ambulatory) patients or Cohort 1 patients. Nonambulatory patients who have previously received enzyme replacement therapy with alglucosidase alfa are referred to as nonambulatory ERT-switch (or ERT-switch nonambulatory) patients or Cohort 2 patients. Ambulatory patients who have not previously received enzyme replacement therapy with alglucosidase alfa are referred to as ERT-naïve (or ERT-naïve ambulatory) patients or Cohort 3 patients.

Sixteen clinical sites in five countries participated in the ATB200-02 study. The study employed the following key inclusion criteria: males and females aged 18-65 years who were diagnosed with Pompe disease based on documented deficiency of GAA enzyme activity or by GAA phenotyping, and who had received enzyme replacement therapy with alglucosidase alfa for 2-6 years (or ≥2 years for Cohort 2) prior to trial initiation (Cohort 1). Eligible subjects were those currently receiving alglucosidase alfa at a frequency of every other week and having completed the last 2 infusions without a drug-related adverse event (AE) resulting in dose interruption (Cohorts 1 and 2). Subjects had to be able to walk between 200 and 500 meters on the 6-Minute Walk Test (6MWT) (Cohorts 1 and 3), have an upright forced vital capacity (FVC) of 30-80% of predicted normal value (Cohorts 1 and 3), or be wheelchair-bound and unable to walk unassisted (Cohort 2). Protocols for the 6MWT and FVC test can be found, for example, in Lachman and Schoser, *Journal of Rare Diseases*, 2013, 8:160, and in Bittner and Singh, The 6 Minute Walk Test, *Cardiology Advisor*, 2013. FIG. 19C provides the baseline characteristics for 20 subjects. Safety, tolerability, and biomarkers were assessed for Cohorts 1, 2 and 3. The following functional assessments were assessed for Cohorts 1 and 3: 6MWT, other motor function tests (time tests and gait-stair-gower-chair (GSGC)), manual muscle test, and pulmonary function (FVC, maximal inspiratory pressure (MIP)/maximal expiratory pressure (MEP)). Protocols for the time tests and GSGC tests can be found, for example in Lachman and Schoser, *Journal of Rare Diseases*, 2013, 8:160. For Cohort 2, the functional assessments included muscle strength tests.

Example 9: Interim PK Results from the ATB200-02 Trial

A summary of pharmacokinetics data for AT2221 is provided in FIG. 20. Total GAA protein concentrations in plasma for ATB200 at 5 mg/kg, 10 mg/kg, and 20 mg/kg were determined by validated LC-MS/MS quantification of rhGAA-specific "signature" peptide(s) T09 (primary) and T50 (confirmatory) for 11 Cohort 1 patients who completed Stages 1 and 2, as well as for five Cohort 2 patients who completed the PK study in Stage 3. For Stage 1, blood samples for plasma total GAA protein concentration were collected prior to the start of ATB200 infusion and at 1, 2, 3, 3.5, 4, 4.5, 5, 6, 8, 10, 12, and 24 hour(s) after the start of infusion. For Stage 2 and Stage 3, blood samples for plasma total GAA protein concentration were collected prior to the start of infusion and at 1, 2, 3, 3.5, 4, 4.5, 5, 6, 8, 10, 12, and 24 hour(s) after the start of infusion.

AT2221 PK analyses were also performed for 11 Cohort 1 patients who completed Stages 1 and 2, as well as for five Cohort 2 patients who completed the PK study in Stage 3. Blood samples for plasma AT2221 concentrations were taken just prior to AT2221 oral administration (time 0) and at 1, 1.5, 2, 2.5, 3, 4, 5, 6, 9, 11, and 25 hour(s) after AT2221 oral administration. Plasma AT2221 was determined by a validated LC-MS/MS assay.

Figure 22A:
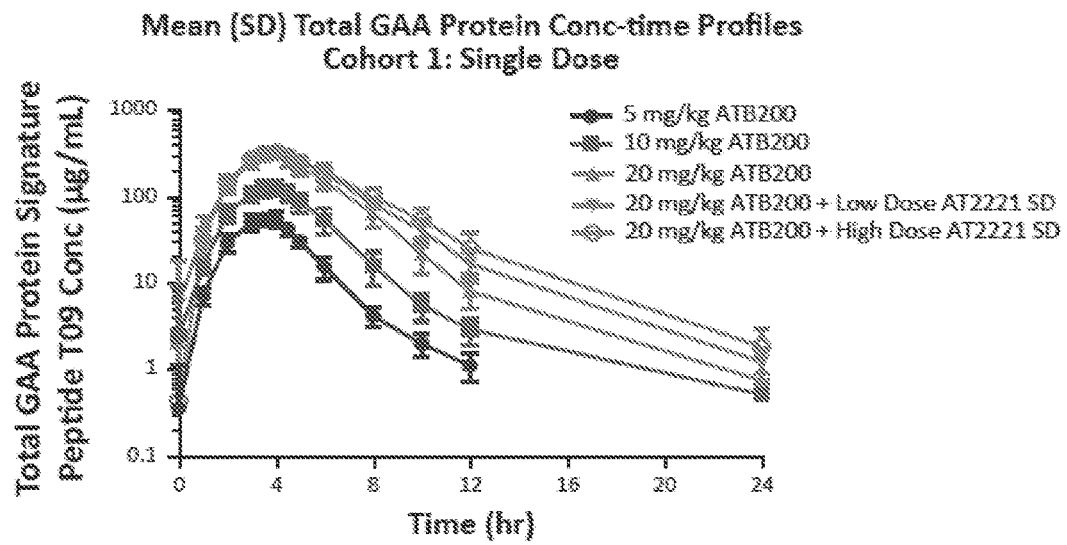
FIGS. 22A, 22B, 22C, 22D, 22E, and 22F depict total GAA protein by cohort. Low dose=130 mg. High dose=260 mg.
Figure 22B:
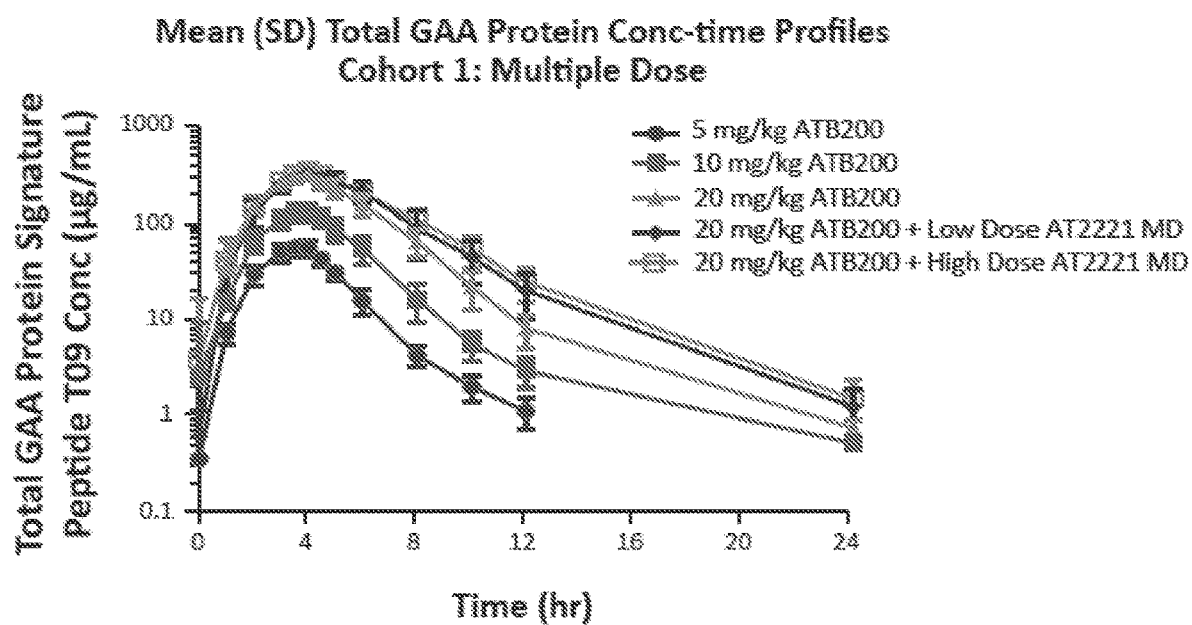
Figure 22C:
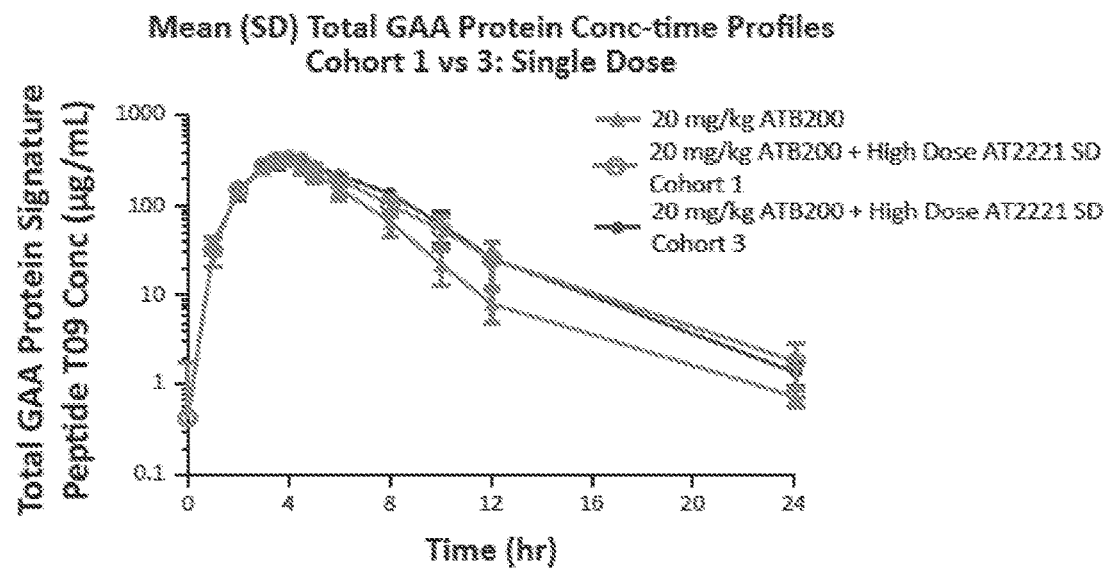
Figure 22D:
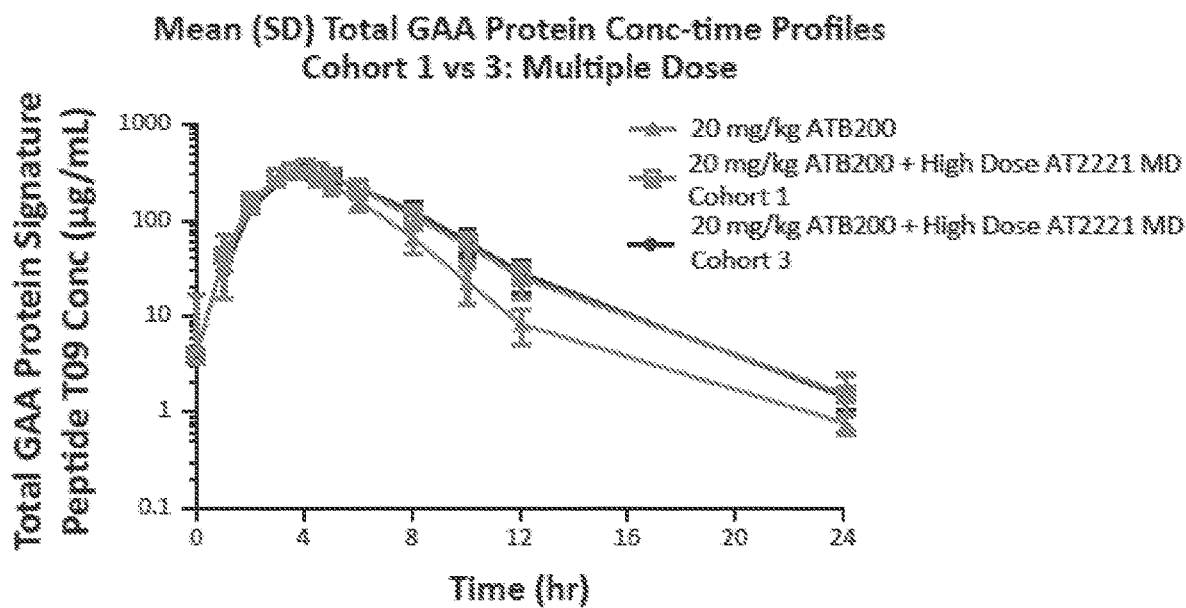
Figure 22E:
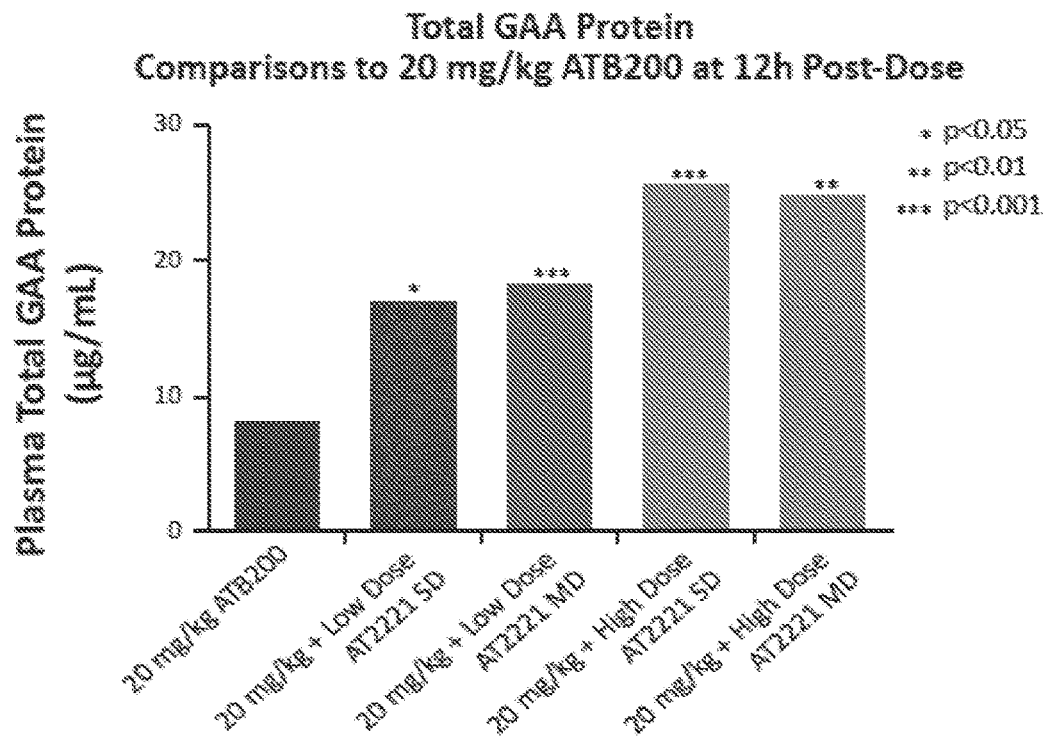
Figure 22F:
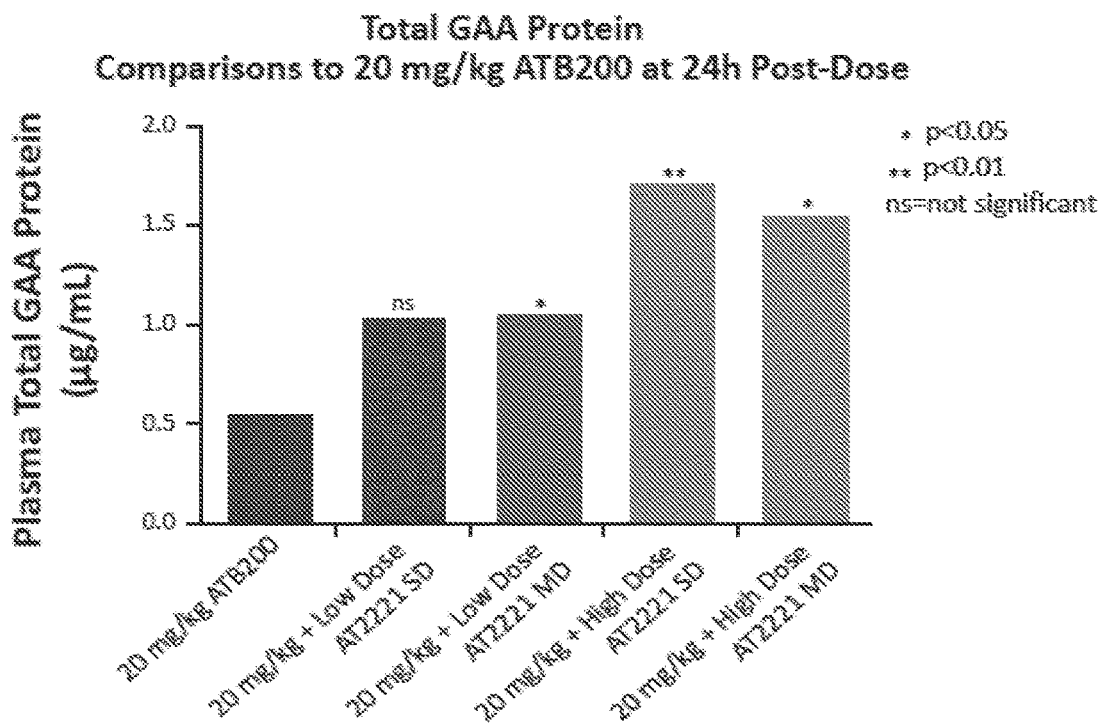

As shown in FIG. 21, levels of ATB200 increased in a slightly greater-than-dose proportional manner when administered alone. Co-administration of ATB200 at 20 mg/kg with a single high dose (260 mg) of AT2221 increased the total GAA protein exposure area under the curve (AUC) by approximately 17% compared to ATB200 at 20 mg/kg administered alone (FIG. 21, FIG. 22C). Co-administration of ATB200 at 20 mg/kg with multiple high doses (260 mg) of AT2221 increased the total GAA protein exposure area under the curve (AUC) by approximately 29%, compared to ATB200 at 20 mg/kg administered alone (FIG. 21, FIG. 22D). Increases in the distribution half-life and partial AUC-24h were observed on the log scale, during the terminal elimination phase (FIG. 21, FIG. 22A, FIG. 22B). As shown in FIG. 21, the distribution half-life (α-phase) increased by 40%, consistent with the stabilizing effect of high-dose AT2221 on ATB200 in plasma. The increase in the distribution half-life was accompanied by an increase in partial AUC from time to maximum plasma concentration to 24 hours post-dose by 42.2% (FIG. 21, FIG. 22B). Further evidence of ATB200 stabilization by AT2221 was observed in 12- and 24-hour post-dose comparisons of low- and high-dose AT2221 vs ATB200 alone (FIGS. 22E and 22F). There was no statistically significant difference in plasma total GAA protein exposure between ERT-naive (Cohort 3) and ERT-switch patients (Cohort 1) (FIG. 23). The PK disposition of signature peptide T50 did not differ from that of signature peptide T09 (AUC ratio: 1.00).

Example 10: Interim Efficacy Results from the ATB200-02 Trial

As shown in FIGS. 24A and 24B, 6MWT improved for ambulatory ERT-switch patients and ERT-naïve patients at month 6 with continued benefit observed to month 12.

6MWT increased in 7/10, 8/10, and 8/8 ERT-switch patients at months 6, 9, and 12, respectively. 6MWT increased in 5/5, 5/5, and 2/2 ERT-naïve patients at Months 6, 9, and 12, respectively.

As shown in FIG. 24C, FIG. 26A, and FIG. 26C, improvements in motor function tests and manual muscle strength, along with 6MWT, were consistent with an overall improvement in muscle function for both ERT-switch and ERT-naïve patients over 12 months.

As shown in FIG. 25, and FIG. 26B, consistent and substantial increases were observed in upper extremity strength in all nonambulatory ERT-switch patients at month 6 and month 9.

As shown in FIG. 27, FVC was stable or increased in 5/9, 6/9, and 3/7 ERT-switch patients at months 6, 9, and 12 respectively and FVC was stable or increased in 5/5, 5/5, and 2/2 ERT-naïve patients at months 6, 9, and 12, respectively. Also as shown in FIG. 27, maximal inspiratory pressure (MIP) was stable and maximal expiratory pressure (MEP) increased in ERT-switch ambulatory patients, while MIP increased and MEP was stable in ERT-naïve patients.

The Fatigue Severity Scale ("FSS") is a self-assessment questionnaire consisting of nine questions, each scored on a scale of 1 to 7. The total score ranges from 9 to 63, with higher values representing higher level of fatigue due to the disease condition. The normative value in the healthy population is approximately 21 (Grace J et al. Parkinsonism Relat Disord. 2007:13:443-445). As shown in FIG. 28, all cohorts were significantly impacted by fatigue at baseline, and all cohorts demonstrated an improvement in their FSS after receiving ATB200/AT2221.

Example 11: Interim Results from the ATB200-02 Trial: Markers of Muscle Injury

The following muscle damage markers were assessed: creatine kinase (CK) enzyme, alanine aminotransferase (ALT), and aspartate aminotransferase (AST). Results available after nine months of the clinical trial are reported in FIGS. 29A-29C (data from a maximum of 58 weeks, 24 weeks, and 36 weeks for Cohorts 1, 2, and 3, respectively; lower n values reflect that some data were either unable to be analyzed or were not yet analyzed). Mean reductions from baseline observed at these respective time points were approximately 30-35% for the ambulatory ERT-switch patients (n=9), 5-20% for the nonambulatory ERT-switch patients (n=4), and 40-55% for the ERT-naïve patients (n=5). Results for CK enzyme available after twelve months of the clinical trial are reported in FIG. 29D (data from a maximum of 12 months for Cohorts 1, 2, and 3; lower n values reflect that some data were either unable to be analyzed or were not yet analyzed).

Urine hexose tetrasaccharide (Hex4) was assessed as a marker of glycogen accumulation. Results for Hex4 available after twelve months of the clinical trial are reported in FIG. 29D (data from a maximum of 12 months for Cohorts 1, 2, and 3; lower n values reflect that some data were either unable to be analyzed or were not yet analyzed).

Example 12: Interim Safety Results from the ATB200-02 Trial

The longest duration of treatment was over 20 months. Adverse events (AEs) were generally mild and transient, with a very low rate of infusion-associated reactions (less than 1%) after over 400 total infusions across all three Cohorts. These incidences were controlled by standard premedication.

The most common AEs reported as treatment-related at up to 72 weeks were nausea (3/20), tremor (3/20), headache (3/20), fatigue (3/20), diarrhea (2/20), muscle spasm (2/20), and joint swelling (2/20).

The most common AEs reported as treatment-related at up to 20+ months were abdominal pain (including upper and lower abdominal pain) (8/20), diarrhea (8/20), nasopharyngitis (6/20), nausea (5/20), headache (5/20), and upper respiratory tract infection (5/20) (FIG. 30). One serious AE was reported, which was unrelated to the study drug (hospitalization for lower respiratory tract infection). No patients discontinued the study due to an AE.

There were three incidents of infusion-associated reactions (IARs) in 550+ infusions, which were controlled by standard premedication. One IAR event (skin discoloration) occurred in a nonambulatory ERT-switch patient (Cohort 2). Two IAR events (localized pruritus, erythema, and burning sensation) occurred in an ERT-naïve patient (Cohort 3) (FIG. 30).

Example 13: Summary and Conclusions of Interim Results from the ATB200-02 Trial

As summarized in FIG. 31, there is concordance in the interim data from the ATB200-02 trial showing significant and unexpected parallel improvements in markers of muscle injury and substrate accumulation, muscle function tests (timed tests and endurance), manual muscle strength, and stabilization and/or improvement in respiratory function tests across the different cohorts. Muscle function improved in 16/18 and 10/10 patients at months 6 and 9, respectively. Increases in 6MWT distance were consistent and durable in ERT-switch ambulatory and ERT-naïve patients out to month 12, as were the improvements in other motor function tests in ERT-switch ambulatory and ERT-naïve patients. Qualitative and quantitative measures showed increases in upper extremity strength in nonambulatory ERT-switch patients at months 6 and 9. FVC, MIP, and MEP were generally stable in ERT-switch patients and increased in ERT-naïve patients. An improvement in fatigue score was observed in all cohorts. Biomarker levels (e.g., levels of CK and Hex4) decreased in all cohorts and ATB200/AT2221 was generally well tolerated.

Thus, the multi-dimensional impact of the therapy suggests that the combination regimen of ATB200/AT2221 has the potential to be an important treatment option for patients with Pompe disease. These clinical results support the results from the single fiber analysis studies described in Example 7, which demonstrate that the treatment is effective at clearing pathology from muscle fibers. Further study of the clinical trial is ongoing.

We claim:

1. A method of reducing urine hexose tetrasaccharide in an ERT-switch patient having Pompe disease in need thereof, the method comprising:
intravenously administering to the patient a population of recombinant human acid α-glucosidase (rhGAA) molecules from Chinese hamster ovary (CHO) cells at a dose of 20 mg/kg; and
concurrently or sequentially orally administering miglustat or a pharmaceutically acceptable salt thereof at a dose of 260 mg,
wherein the rhGAA molecules comprise seven potential N-glycosylation sites;
wherein the rhGAA molecules on average comprise 3-4 mannose-6-phosphate (M6P) residues; and
wherein the rhGAA molecules on average comprise at least 0.5 mol bis-mannose-6-phosphate (bis-M6P) per mol of rhGAA at the first potential N-glycosylation site as determined using liquid chromatography-tandem mass spectrometry (LC-MS/MS),
and wherein, compared to baseline, the patient's levels of urine hexose tetrasaccharide after six months of treatment are reduced by at least 35%.

2. The method of claim 1, wherein the population of rhGAA molecules is administered bimonthly, monthly, biweekly, weekly, twice weekly, or daily.

3. The method of claim 1, wherein the miglustat or pharmaceutically acceptable salt thereof is administered prior to administration of the rhGAA.

4. The method of claim 1, wherein the rhGAA molecules comprise an amino acid sequence having at least 95% sequence identity to SEQ ID NO: 1 or SEQ ID NO: 5.

5. The method of claim 1, wherein at least 30% of the rhGAA molecules comprise one or more N-glycan units bearing one mannose-6-phosphate residue (mono-M6P) or bis-M6P, as determined using LC-MS/MS.

6. The method of claim 1, wherein the rhGAA molecules comprise on average from 0.5 mol to 7.0 mol of mono-M6P or bis-M6P per mol of rhGAA, as determined using LC-MS/MS.

7. The method of claim 1, wherein the rhGAA molecules comprise on average at least 2.5 mol M6P per mol of rhGAA and at least 4 mol sialic acid per mol of rhGAA, as determined using LC-MS/MS.

8. The method of claim 1, wherein, per mol of rhGAA, the rhGAA molecules comprise on average:
(a) 0.4 to 0.6 mol mono-M6P at the second potential N-glycosylation site;
(b) 0.4 to 0.6 mol bis-M6P at the fourth potential N-glycosylation site; and
(c) 0.3 to 0.4 mol mono-M6P at the fourth potential N-glycosylation site;
wherein (a)-(c) are determined using LC-MS/MS.

9. The method of claim 8, wherein, per mol of rhGAA, the rhGAA molecules comprise on average:
(a) 0.9 to 1.2 mol sialic acid at the third potential N-glycosylation site;
(b) 0.8 to 0.9 mol sialic acid at the fifth potential N-glycosylation site; and
(c) 1.5 to 4.2 mol sialic acid at the sixth potential N-glycosylation site;
wherein (a)-(c) are determined using LC-MS/MS, and
wherein, per mol of rhGAA, the rhGAA molecules further comprise 4 mol to 7.3 mol sialic acid.

10. The method of claim 1, wherein the population of rhGAA molecules is formulated in a pharmaceutical composition.

11. The method of claim 10, wherein the pharmaceutical composition further comprises at least one buffer selected from the group consisting of a citrate, a phosphate, and a combination thereof, and at least one excipient selected from the group consisting of mannitol, polysorbate 80, and a combination thereof; wherein the pharmaceutical composition has a pH of 5.0 to 7.0.

12. The method of claim 11, wherein, in the pharmaceutical composition, the population of rhGAA molecules is present at a concentration of 5-50 mg/mL, the at least one buffer is a sodium citrate buffer present at a concentration of 10-100 mM, the at least one excipient is mannitol present at a concentration of 10-50 mg/mL and polysorbate 80 present at a concentration of 0.1-1 mg/mL, and the pharmaceutical composition further comprises water and optionally comprises an acidifying agent and/or alkalizing agent; wherein the pharmaceutical composition has a pH of 6.0.

13. The method of claim 1, wherein, compared to baseline, the patient's pulmonary function, as measured by an upright forced vital capacity (FVC) test, is improved after six months of treatment.

14. The method of claim 1, wherein, after six months of treatment, the patient is ambulatory and, compared to baseline, the patient's creatine kinase levels are reduced by at least 15%; or the patient is nonambulatory and, compared to baseline, the patient's creatine kinase levels are reduced by at least 20%.

15. A method of improving pulmonary function in an ERT-switch patient having Pompe disease in need thereof, the patient having an upright forced vital capacity (FVC) of 30-80% of predicted normal value, the method comprising:
intravenously administering to the patient a population of recombinant human acid α-glucosidase (rhGAA) molecules from Chinese hamster ovary (CHO) cells at a dose of 20 mg/kg; and concurrently or sequentially orally administering miglustat or a pharmaceutically acceptable salt thereof at a dose of 260 mg, wherein the rhGAA molecules comprise seven potential N-glycosylation sites;

wherein the rhGAA molecules on average comprise 3-4 mannose-6-phosphate (M6P) residues; and wherein the rhGAA molecules on average comprise at least 0.5 mol bis-mannose-6-phosphate (bis-M6P) per mol of rhGAA at the first potential N-glycosylation site as determined using liquid chromatography-tandem mass spectrometry (LC-MS/MS).

16. The method of claim 15, wherein the improvement of pulmonary function is measured by an upright forced vital capacity (FVC) test after six months of treatment and the patient exhibits an improvement in FVC of at least 4%.

17. A method of reducing creatine kinase levels in an ERT-switch patient having Pompe disease in need thereof, the method comprising:

intravenously administering to the patient a population of recombinant human acid a-glucosidase (rhGAA) molecules from Chinese hamster ovary (CHO) cells at a dose of 20 mg/kg; and concurrently or sequentially orally administering miglustat or a pharmaceutically acceptable salt thereof at a dose of 260 mg, wherein the rhGAA molecules comprise seven potential N-glycosylation sites;

wherein the rhGAA molecules on average comprise 3-4 mannose-6-phosphate (M6P) residues; and wherein the rhGAA molecules on average comprise at least 0.5 mol bis-mannose-6-phosphate (bis-M6P) per mol of rhGAA at the first potential N-glycosylation site as determined using liquid chromatography-tandem mass spectrometry (LC-MS/MS) and wherein after six months of treatment, if the patient is ambulatory, compared to baseline, the patient's creatine kinase levels are reduced by at least 15%; or if the patient is nonambulatory, compared to baseline, the patient's creatine kinase levels are reduced by at least 20%.

18. The method of claim 1, wherein the patient has an upright forced vital capacity (FVC) of 30-80% of predicted normal value.

19. The method of claim 17, wherein the patient has an upright forced vital capacity (FVC) of 30-80% of predicted normal value.

* * * * *

SEQUENCE LISTING

<160> NUMBER OF SEQ ID NOS: 5

<210> SEQ ID NO 1

<211> LENGTH: 952
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
```

```
                370                 375                 380
Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
            565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
            770                 775                 780

Ser Leu Pro Pro Pro Ala Ala Pro Arg Glu Pro Ala Ile His Ser
785                 790                 795                 800
```

```
Glu Gly Gln Trp Val Thr Leu Pro Ala Pro Leu Asp Thr Ile Asn Val
            805                 810                 815
His Leu Arg Ala Gly Tyr Ile Ile Pro Leu Gln Gly Pro Gly Leu Thr
        820                 825                 830
Thr Thr Glu Ser Arg Gln Gln Pro Met Ala Leu Ala Val Ala Leu Thr
    835                 840                 845
Lys Gly Gly Glu Ala Arg Gly Glu Leu Phe Trp Asp Asp Gly Glu Ser
850                 855                 860
Leu Glu Val Leu Glu Arg Gly Ala Tyr Thr Gln Val Ile Phe Leu Ala
865                 870                 875                 880
Arg Asn Asn Thr Ile Val Asn Glu Leu Val Arg Val Thr Ser Glu Gly
            885                 890                 895
Ala Gly Leu Gln Leu Gln Lys Val Thr Val Leu Gly Val Ala Thr Ala
        900                 905                 910
Pro Gln Gln Val Leu Ser Asn Gly Val Pro Val Ser Asn Phe Thr Tyr
    915                 920                 925
Ser Pro Asp Thr Lys Val Leu Asp Ile Cys Val Ser Leu Leu Met Gly
930                 935                 940
Glu Gln Phe Leu Val Ser Trp Cys
945                 950

<210> SEQ ID NO 2
<211> LENGTH: 3624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cagttgggaa agctgaggtt gtcgccgggg ccgcgggtgg aggtcgggga tgaggcagca      60
ggtaggacag tgacctcggt gacgcgaagg accccggcca cctctaggtt ctcctcgtcc     120
gcccgttgtt cagcgaggga ggctctgggc ctgccgcagc tgacggggaa actgaggcac     180
ggagcgggcc tgtaggagct gtccaggcca tctccaacca tgggagtgag cacccgccc      240 tgctcccacc ggctcctggc cgtctgcgcc ctcgtgtcct tggcaaccgc tgcactcctg     300
gggcacatcc tactccatga tttcctgctg gttccccgag agctgagtgg ctcctcccca     360
gtcctggagg agactcaccc agctcaccag cagggagcca gcagaccagg gccccgggat     420
gcccaggcac accccggccg tcccagagca gtgcccacac agtgcgacgt ccccccccaac    480 agccgcttcg attgcgcccc tgacaaggcc atcacccagg aacagtgcga ggcccgcggc     540
tgctgctaca tccctgcaaa gcaggggctg caggagcccc agatggggca gcctggtgc      600 ttcttcccac ccagctaccc cagctacaag ctggagaacc tgagctcctc tgaaatgggc     660
tacacggcca ccctgacccg taccaccccc acctccttcc ccaaggacat cctgacccctg    720 cggctggacg tgatgatgga gactgagaac cgcctccact tcacgatcaa agatccagct     780
aacaggcgct acgaggtgcc cttggagacc ccgcgtgtcc acagccgggc accgtcccca    840
ctctacagcg tggagttctc cgaggagccc ttcggggtga tcgtgcaccg gcagctggac     900
ggccgcgtgc tgctgaacac gacggtggcg cccctgttct ttgcggacca gttccttcag    960
ctgtccacct cgctgccctc gcagtatatc acaggcctcg ccgagcacct cagtcccctg    1020
atgctcagca ccagctggac caggatcacc ctgtggaacc gggaccttgc gcccacgcc     1080 ggtgcgaacc tctacgggtc tcaccctttc tacctggcgc tggaggacgg cgggtcggca    1140
```

```
cacggggtgt tcctgctaaa cagcaatgcc atggatgtgg tcctgcagcc gagccctgcc    1200
cttagctgga ggtcgacagg tgggatcctg atgtctaca tcttcctggg cccagagccc    1260
aagagcgtgg tgcagcagta cctggacgtt gtgggatacc cgttcatgcc gccatactgg    1320
ggcctgggct tccacctgtg ccgctggggc tactcctcca ccgctatcac ccgccaggtg    1380
gtggagaaca tgaccagggc ccacttcccc ctggacgtcc aatggaacga cctggactac    1440
atggactccc ggagggactt cacgttcaac aaggatggct ccgggactt cccggccatg    1500 gtgcaggagc tgcaccaggg cggccggcgc tacatgatga tcgtggatcc tgccatcagc    1560
agctcgggcc ctgccgggag ctacaggccc tacgacgagg tctgcggag gggggttttc    1620 atcaccaacg agaccggcca gccgctgatt gggaaggtat ggcccgggtc cactgccttc    1680
cccgacttca ccaaccccac agccctggcc tggtgggagg acatggtggc tgagttccat    1740
gaccaggtgc ccttcgacgg catgtggatt gacatgaacg agccttccaa cttcatcaga    1800
ggctctgagg acggctgccc caacaatgag ctggagaacc cacccctacgt gcctggggtg    1860 gttgggggga ccctccaggc ggccaccatc tgtgcctcca gccaccagtt tctctccaca    1920
cactacaacc tgcacaacct ctacggcctg accgaagcca tcgcctccca cagggcgctg    1980
gtgaaggctc gggggacacg cccatttgtg atctcccgct cgacctttgc tggccacggc    2040
cgatacgccg gccactggac gggggacgtg tggagctcct gggagcagct cgcctcctcc    2100
gtgccagaaa tcctgcagtt taacctgctg ggggtgcctc tggtcggggc cgacgtctgc    2160
ggcttcctgg gcaacacctc agaggagctg tgtgtgcgct ggacccagct gggggccttc    2220 tacccctca tgcggaacca caacagcctg ctcagtctgc cccaggagcc gtacagcttc    2280
agcgagccgg cccagcaggc catgaggaag gccctcaccc tgcgctacgc actcctcccc    2340
cacctctaca cactgttcca ccaggcccac gtcgcggggg agaccgtggc ccggcccctc    2400
ttcctggagt tccccaagga ctctagcacc tggactgtgg accaccagct cctgtggggg    2460
gaggccctgc tcatcacccc agtgctccag gccgggaagg ccgaagtgac tggctacttc    2520
cccttgggca catggtacga cctgcagacg gtgccaatag aggcccttgg cagcctccca    2580
cccccacctg cagctccccg tgagccagcc atccacagcg agggcagtg ggtgacgctg    2640 ccggccccc tggacaccat caacgtccac ctccgggctg gtacatcat ccccctgcag    2700 ggccctggcc tcaaccac agagtccgc cagcagccca tggccctggc tgtggccctg    2760
accaagggtg agaggcccg aggggagctg ttctgggacg atggagagag cctggaagtg    2820
ctggagcgag gggcctacac acaggtcatc ttcctggcca ggaataacac gatcgtgaat    2880
gagctggtac gtgtgaccag tgagggagct ggcctgcagc tgcagaaggt gactgtcctg    2940
ggcgtggcca cggcgcccca gcaggtcctc tccaacggtg tccctgtctc caacttcacc    3000
tacagccccg acaccaaggt cctggacatc tgtgtctcgc tgttgatggg agagcagttt    3060
ctcgtcagct ggtgttagcc gggcggagtg tgttagtctc tccagaggga ggctggttcc    3120
ccagggaagc agagcctgtg tgcgggcagc agctgtgtgc gggcctgggg gttgcatgtg    3180
tcacctggag ctgggcacta accattccaa gccgccgcat cgcttgtttc cacctcctgg    3240
gccggggctc tggcccccaa cgtgtctagg agagcttctt ccctagatcg cactgtgggc    3300
cggggcctgg agggctgctc tgtgttaata agattgtaag gtttgccctc ctcacctgtt    3360
gccggcatgc gggtagtatt agccaccccc ctccatctgt tcccagcacc ggagaagggg    3420
gtgctcaggt ggaggtgtgg ggtatgcacc tgagctcctg cttcgcgcct gctgctctgc    3480
```

```
cccaacgcga  ccgcttcccg  gctgcccaga  gggctggatg  cctgccggtc  cccgagcaag    3540
cctgggaact  caggaaaatt  cacaggactt  gggagattct  aaatcttaag  tgcaattatt    3600
ttaataaaag  gggcatttgg  aatc                                              3624
```

<210> SEQ ID NO 3
<211> LENGTH: 952
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335
```

-continued

```
Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
            370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
            405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
        450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
            565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
            740                 745                 750
```

```
Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
        770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
        900                 905                 910

Pro Gln Gln Val Leu Ser Asn Gly Val Pro Val Ser Asn Phe Thr Tyr
    915                 920                 925

Ser Pro Asp Thr Lys Val Leu Asp Ile Cys Val Ser Leu Leu Met Gly
        930                 935                 940

Glu Gln Phe Leu Val Ser Trp Cys
945                 950

<210> SEQ ID NO 4
<211> LENGTH: 952
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160
```

```
Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575
```

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 5
<211> LENGTH: 896
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Gln Gln Gly Ala Ser Arg Pro Gly Pro Arg Asp Ala Gln Ala His Pro
1               5                   10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60

Gln Met Gly Gln Pro Trp Cys Phe Phe Pro Pro Ser Tyr Pro Ser Tyr
65                  70                  75                  80

Lys Leu Glu Asn Leu Ser Ser Ser Glu Met Gly Tyr Thr Ala Thr Leu
                85                  90                  95

Thr Arg Thr Thr Pro Thr Phe Phe Pro Lys Asp Ile Leu Thr Leu Arg
            100                 105                 110

Leu Asp Val Met Met Glu Thr Glu Asn Arg Leu His Phe Thr Ile Lys
        115                 120                 125

Asp Pro Ala Asn Arg Arg Tyr Glu Val Pro Leu Glu Thr Pro Arg Val
    130                 135                 140

His Ser Arg Ala Pro Ser Pro Leu Tyr Ser Val Glu Phe Ser Glu Glu
145                 150                 155                 160

Pro Phe Gly Val Ile Val His Arg Gln Leu Asp Gly Arg Val Leu Leu
                165                 170                 175

Asn Thr Thr Val Ala Pro Leu Phe Phe Ala Asp Gln Phe Leu Gln Leu
            180                 185                 190

Ser Thr Ser Leu Pro Ser Gln Tyr Ile Thr Gly Leu Ala Glu His Leu
        195                 200                 205

Ser Pro Leu Met Leu Ser Thr Ser Trp Thr Arg Ile Thr Leu Trp Asn
    210                 215                 220

Arg Asp Leu Ala Pro Thr Pro Gly Ala Asn Leu Tyr Gly Ser His Pro
225                 230                 235                 240

Phe Tyr Leu Ala Leu Glu Asp Gly Gly Ser Ala His Gly Val Phe Leu
                245                 250                 255

Leu Asn Ser Asn Ala Met Asp Val Val Leu Gln Pro Ser Pro Ala Leu
            260                 265                 270

Ser Trp Arg Ser Thr Gly Gly Ile Leu Asp Val Tyr Ile Phe Leu Gly
        275                 280                 285

Pro Glu Pro Lys Ser Val Val Gln Gln Tyr Leu Asp Val Val Gly Tyr
    290                 295                 300

Pro Phe Met Pro Pro Tyr Trp Gly Leu Gly Phe His Leu Cys Arg Trp
305                 310                 315                 320

Gly Tyr Ser Ser Thr Ala Ile Thr Arg Gln Val Val Glu Asn Met Thr
                325                 330                 335

Arg Ala His Phe Pro Leu Asp Val Gln Trp Asn Asp Leu Asp Tyr Met
            340                 345                 350

Asp Ser Arg Arg Asp Phe Thr Phe Asn Lys Asp Gly Phe Arg Asp Phe
        355                 360                 365

Pro Ala Met Val Gln Glu Leu His Gln Gly Gly Arg Arg Tyr Met Met
    370                 375                 380

Ile Val Asp Pro Ala Ile Ser Ser Ser Gly Pro Ala Gly Ser Tyr Arg
385                 390                 395                 400
```

-continued

```
Pro Tyr Asp Glu Gly Leu Arg Arg Gly Val Phe Ile Thr Asn Glu Thr
            405                 410                 415
Gly Gln Pro Leu Ile Gly Lys Val Trp Pro Gly Ser Thr Ala Phe Pro
        420                 425                 430
Asp Phe Thr Asn Pro Thr Ala Leu Ala Trp Trp Glu Asp Met Val Ala
        435                 440                 445
Glu Phe His Asp Gln Val Pro Phe Asp Gly Met Trp Ile Asp Met Asn
    450                 455                 460
Glu Pro Ser Asn Phe Ile Arg Gly Ser Glu Asp Gly Cys Pro Asn Asn
465                 470                 475                 480
Glu Leu Glu Asn Pro Pro Tyr Val Pro Gly Val Val Gly Gly Thr Leu
                485                 490                 495
Gln Ala Ala Thr Ile Cys Ala Ser Ser His Gln Phe Leu Ser Thr His
            500                 505                 510
Tyr Asn Leu His Asn Leu Tyr Gly Leu Thr Glu Ala Ile Ala Ser His
        515                 520                 525
Arg Ala Leu Val Lys Ala Arg Gly Thr Arg Pro Phe Val Ile Ser Arg
    530                 535                 540
Ser Thr Phe Ala Gly His Gly Arg Tyr Ala Gly His Trp Thr Gly Asp
545                 550                 555                 560
Val Trp Ser Ser Trp Glu Gln Leu Ala Ser Ser Val Pro Glu Ile Leu
                565                 570                 575
Gln Phe Asn Leu Leu Gly Val Pro Leu Val Gly Ala Asp Val Cys Gly
            580                 585                 590
Phe Leu Gly Asn Thr Ser Glu Glu Leu Cys Val Arg Trp Thr Gln Leu
        595                 600                 605
Gly Ala Phe Tyr Pro Phe Met Arg Asn His Asn Ser Leu Leu Ser Leu
    610                 615                 620
Pro Gln Glu Pro Tyr Ser Phe Ser Glu Pro Ala Gln Gln Ala Met Arg
625                 630                 635                 640
Lys Ala Leu Thr Leu Arg Tyr Ala Leu Leu Pro His Leu Tyr Thr Leu
                645                 650                 655
Phe His Gln Ala His Val Ala Gly Glu Thr Val Ala Arg Pro Leu Phe
            660                 665                 670
Leu Glu Phe Pro Lys Asp Ser Ser Thr Trp Thr Val Asp His Gln Leu
        675                 680                 685
Leu Trp Gly Glu Ala Leu Leu Ile Thr Pro Val Leu Gln Ala Gly Lys
    690                 695                 700
Ala Glu Val Thr Gly Tyr Phe Pro Leu Gly Thr Trp Tyr Asp Leu Gln
705                 710                 715                 720
Thr Val Pro Ile Glu Ala Leu Gly Ser Leu Pro Pro Pro Ala Ala
                725                 730                 735
Pro Arg Glu Pro Ala Ile His Ser Glu Gly Gln Trp Val Thr Leu Pro
            740                 745                 750
Ala Pro Leu Asp Thr Ile Asn Val His Leu Arg Ala Gly Tyr Ile Ile
        755                 760                 765
Pro Leu Gln Gly Pro Gly Leu Thr Thr Thr Glu Ser Arg Gln Gln Pro
    770                 775                 780
Met Ala Leu Ala Val Ala Leu Thr Lys Gly Gly Glu Ala Arg Gly Glu
785                 790                 795                 800
Leu Phe Trp Asp Asp Gly Glu Ser Leu Glu Val Leu Glu Arg Gly Ala
                805                 810                 815
Tyr Thr Gln Val Ile Phe Leu Ala Arg Asn Asn Thr Ile Val Asn Glu
```

```
                820             825                 830
Leu Val Arg Val Thr Ser Glu Gly Ala Gly Leu Gln Leu Gln Lys Val
            835                 840                 845

Thr Val Leu Gly Val Ala Thr Ala Pro Gln Gln Val Leu Ser Asn Gly
        850                 855                 860

Val Pro Val Ser Asn Phe Thr Tyr Ser Pro Asp Thr Lys Val Leu Asp
865             870                 875                     880

Ile Cys Val Ser Leu Leu Met Gly Glu Gln Phe Leu Val Ser Trp Cys
                885                 890                 895
```